(12) United States Patent
Yen et al.

(10) Patent No.: US 12,337,319 B2
(45) Date of Patent: Jun. 24, 2025

(54) MICROFLUIDIC CHIP FOR ACOUSTIC SEPARATION OF BIOLOGICAL OBJECTS

(71) Applicant: Applied Cells Inc., Santa Clara, CA (US)

(72) Inventors: Bing K. Yen, Cupertino, CA (US); Yuchen Zhou, San Jose, CA (US)

(73) Assignee: Applied Cells Inc.

( * ) Notice: Subject to any disclaimer, the term of this patent is extended or adjusted under 35 U.S.C. 154(b) by 740 days.

(21) Appl. No.: 17/528,493

(22) Filed: Nov. 17, 2021

(65) Prior Publication Data

US 2022/0072548 A1     Mar. 10, 2022

Related U.S. Application Data

(63) Continuation-in-part of application No. 16/565,164, filed on Sep. 9, 2019, now Pat. No. 11,541,391, which
(Continued)

(51) Int. Cl.
*B01L 3/00*       (2006.01)
*A61K 38/27*     (2006.01)
(Continued)

(52) U.S. Cl.
CPC ........ *B01L 3/502753* (2013.01); *A61K 38/27* (2013.01); *B01D 21/283* (2013.01);
(Continued)

(58) Field of Classification Search
CPC ......... B01L 3/502753; B01L 3/502715; B01L 3/50273; B01L 3/502761; B01L 2200/027;
(Continued)

(56) References Cited

U.S. PATENT DOCUMENTS 4,759,775 A    7/1988   Peterson et al.
5,902,489 A    5/1999   Yasuda et al.
(Continued)

FOREIGN PATENT DOCUMENTS

WO     2009132151     10/2009

OTHER PUBLICATIONS

Nam et al., Separation of platelets from whole blood using standing surface acoustic waves in a microchannel, Lab on a chip, 2011, 11, 3361-3364 (Year: 2011).*
(Continued)

*Primary Examiner* — Luan V Van
*Assistant Examiner* — Shizhi Qian
(74) *Attorney, Agent, or Firm* — Bing K. Yen

(57) ABSTRACT

A microfluidic device for sorting biological objects includes a microfluidic chip including a planar substrate having first and second planar surfaces, the planar substrate including first and second networks of channels recessed respectively from the first and second planar surfaces and fluidically connected by way of at least a through-hole in the planar substrate; a first lid attached to the first planar surface of the planar substrate and substantially covering the first network of channels; and a second lid attached to the second planar surface of the planar substrate and substantially covering the second network of channels; and one or more piezoelectric transducers attached to the first lid and/or the second lid and configured to generate first and second acoustic standing waves in a first linear channel of the first network of channels and a second linear channel of the second network of channels, respectively.

20 Claims, 16 Drawing Sheets

Related U.S. Application Data is a continuation of application No. 15/911,116, filed on Mar. 3, 2018, now Pat. No. 10,449,553, which is a continuation of application No. 15/911,115, filed on Mar. 3, 2018, now Pat. No. 12,145,151.

(51) Int. Cl.

| | | |
|---|---|---|
| *B01D 21/28* | (2006.01) | |
| *B01D 35/06* | (2006.01) | |
| *B01F 31/86* | (2022.01) | |
| *B03C 1/005* | (2006.01) | |
| *B03C 1/033* | (2006.01) | |
| *B03C 1/23* | (2006.01) | |
| *B03C 1/28* | (2006.01) | |
| *B03C 1/30* | (2006.01) | |
| *C12Q 1/6806* | (2018.01) | |
| *G01N 1/40* | (2006.01) | |
| *G01N 15/00* | (2024.01) | |
| *G01N 27/74* | (2006.01) | |
| *G01N 33/49* | (2006.01) | |
| *G01N 33/543* | (2006.01) | |
| *G01N 35/00* | (2006.01) | |

(52) U.S. Cl.
CPC .............. *B01D 35/06* (2013.01); *B01F 31/86* (2022.01); *B01L 3/502715* (2013.01); *B01L 3/50273* (2013.01); *B01L 3/502761* (2013.01); *B03C 1/005* (2013.01); *B03C 1/0332* (2013.01); *B03C 1/23* (2013.01); *B03C 1/288* (2013.01); *B03C 1/30* (2013.01); *C12Q 1/6806* (2013.01); *G01N 1/4077* (2013.01); *G01N 15/00* (2013.01); *G01N 27/745* (2013.01); *G01N 33/491* (2013.01); *G01N 33/54326* (2013.01); *G01N 33/54333* (2013.01); *G01N 35/0098* (2013.01); *B01L 2200/027* (2013.01); *B01L 2200/0647* (2013.01); *B01L 2200/0652* (2013.01); *B01L 2200/0668* (2013.01); *B01L 2300/021* (2013.01); *B01L 2300/0861* (2013.01); *B01L 2300/0864* (2013.01); *B01L 2400/043* (2013.01); *B01L 2400/0436* (2013.01); *B01L 2400/0439* (2013.01); *B01L 2400/0457* (2013.01); *B01L 2400/0487* (2013.01); *B01L 2400/0496* (2013.01); *B03C 2201/18* (2013.01); *B03C 2201/20* (2013.01); *B03C 2201/26* (2013.01); *G01N 2035/00554* (2013.01)

(58) Field of Classification Search
CPC ..... B01L 2200/0647; B01L 2200/0652; B01L 2200/0668; B01L 2200/0636; B01L 2300/021; B01L 2300/0861; B01L 2300/0864; B01L 2300/0874; B01L 2300/0887; B01L 2400/043; B01L 2400/0436; B01L 2400/0439; B01L 2400/0457; B01L 2400/0487; B01L 2400/0496; A61K 38/27; C12Q 1/6806; B01D 21/283; B01D 35/06; B01D 2221/10; B01F 31/86; B03C 1/005; B03C 1/0332; B03C 1/23; B03C 1/288; B03C 1/30; B03C 2201/18; B03C 2201/20; B03C 2201/26; G01N 1/4077; G01N 15/00; G01N 27/745; G01N 33/491; G01N 33/54326; G01N 33/54333; G01N 35/0098; G01N 2035/00554; G01N 2001/4094

See application file for complete search history.

(56) References Cited

U.S. PATENT DOCUMENTS

| | | | |
|---|---|---|---|
| 5,972,721 A | 10/1999 | Bruno et al. | |
| 6,216,538 B1 | 4/2001 | Yasuda et al. | |
| 6,254,830 B1 | 7/2001 | Pivarnik et al. | |
| 6,648,015 B1 * | 11/2003 | Chow | G01N 27/44791 137/833 |
| 6,929,750 B2 | 8/2005 | Laurell et al. | |
| 7,348,185 B2 | 3/2008 | Yamamichi | |
| 7,474,184 B1 | 1/2009 | Humphries et al. | |
| 7,781,202 B2 | 8/2010 | Yamamichi | |
| 8,273,302 B2 | 9/2012 | Takahashi et al. | |
| 8,309,408 B2 | 11/2012 | Ward et al. | |
| 8,573,060 B2 | 11/2013 | Huang et al. | |
| 8,636,906 B2 | 1/2014 | Stein | |
| 8,956,536 B2 | 2/2015 | Yu et al. | |
| 8,986,944 B2 | 3/2015 | Yamanishi et al. | |
| 9,095,494 B2 | 8/2015 | Warner et al. | |
| 9,109,197 B2 | 8/2015 | Yasuda et al. | |
| 9,217,131 B2 | 12/2015 | Lamish et al. | |
| 9,272,234 B2 | 3/2016 | Lipkens et al. | |
| 9,476,855 B2 | 10/2016 | Ward et al. | |
| 9,510,998 B2 | 12/2016 | Warner et al. | |
| 9,513,205 B2 | 12/2016 | Yu et al. | |
| 9,551,643 B2 | 1/2017 | Warner et al. | |
| 9,656,263 B2 | 5/2017 | Laurell et al. | |
| 9,725,690 B2 | 8/2017 | Presz et al. | |
| 9,745,569 B2 | 8/2017 | Lipkens et al. | |
| 9,796,956 B2 | 10/2017 | Lipkens et al. | |
| 9,835,540 B2 | 12/2017 | Yu et al. | |
| 9,885,642 B2 | 2/2018 | Yu | |
| 10,045,913 B2 | 8/2018 | Warner et al. | |
| 10,052,431 B2 | 8/2018 | Dreschel et al. | |
| 10,173,220 B2 | 1/2019 | Middlebrook et al. | |
| 10,444,125 B2 | 10/2019 | Yu | |
| 10,677,695 B2 | 6/2020 | Koyata et al. | |
| 10,710,006 B2 | 7/2020 | Lipkens et al. | |
| 10,724,029 B2 | 7/2020 | Lipkens et al. | |
| 11,900,370 B2 | 2/2024 | Livingston et al. | |
| 2004/0069708 A1 | 4/2004 | Laurell et al. | |
| 2005/0106064 A1 | 5/2005 | Laurell et al. | |
| 2006/0094051 A1 | 5/2006 | Lee et al. | |
| 2006/0240572 A1 | 10/2006 | Carron et al. | |
| 2007/0182517 A1 | 8/2007 | Humphries et al. | |
| 2008/0160630 A1 | 7/2008 | Liu et al. | |
| 2008/0217259 A1 * | 9/2008 | Siversson | B01D 21/283 210/542 |
| 2008/0302732 A1 | 12/2008 | Soh et al. | |
| 2009/0052273 A1 | 2/2009 | Sarvazyan | |
| 2009/0065359 A1 | 3/2009 | Zhou | |
| 2010/0317093 A1 | 12/2010 | Turewicz et al. | |
| 2011/0033922 A1 | 2/2011 | Landers et al. | |
| 2012/0100546 A1 | 4/2012 | Lowery et al. | |
| 2012/0122731 A1 | 5/2012 | Soh et al. | |
| 2012/0295302 A1 | 11/2012 | Lamish et al. | |
| 2013/0265054 A1 | 10/2013 | Lowery et al. | |
| 2013/0330739 A1 | 12/2013 | Yu | |
| 2014/0120570 A1 | 5/2014 | Yu et al. | |
| 2014/0231315 A1 | 8/2014 | Laurell et al. | |
| 2015/0010939 A1 | 1/2015 | Warner et al. | |
| 2015/0177111 A1 | 6/2015 | Warmer et al. | |
| 2015/0253226 A1 | 9/2015 | Augustsson et al. | |
| 2015/0308971 A1 | 10/2015 | Bisgaard et al. | |
| 2016/0252445 A1 | 9/2016 | Yu et al. | |
| 2018/0313816 A1 * | 11/2018 | Fiering | G01N 33/491 |
| 2018/0348097 A1 | 12/2018 | Abbott et al. | |
| 2019/0270084 A1 | 9/2019 | Zhou | |
| 2019/0292565 A1 * | 9/2019 | Tandon | B01L 3/502761 |
| 2019/0307946 A1 * | 10/2019 | Fiering | B03B 1/04 |
| 2022/0193663 A1 * | 6/2022 | Yang | B06B 1/0688 |
| 2022/0389380 A1 * | 12/2022 | Fiering | C12M 47/04 |

(56) References Cited

OTHER PUBLICATIONS

Petersson et al., Separation of lipids from blood utilizing ultrasonic standing waves in microfludic channels, Analyst, 2004, 938-943, vol. 129.
Jonsson et al., Particle separation using ultrasound can radically reduce embolic load to brain after cardiac surgery, The Annals of Thoracic Surgery, 2004, 1572-1578, vol. 78.
Petrov et al., Electrically controlled integrated optical filter, Technical Physics Letters, 2004, 120-122, vol. 30.
Xia et al., Combined microfluidic-micromagnetic separation of living cells in continuous flow, Biomedical Microdevices, 2006, 299-308, vol. 8.
Radisic et al., Micro- and nanotechnology in cell separation, International Journal of Nanomedicine, 2006, 3-14, vol. 1.
Pamme et al., Continuous sorting of magnetic cells via on-chip free-flow magnetophoresis, Lab on a Chip, 2006, 974-980, vol. 6.
Laurell et al., Chip integrated strategies for acoustic separation and manipulation of cells and particles, Chemical Society Reviews, 2007, 492-506, vol. 36.
Riethdorf et al., Detection of circulating tumor cells in peripheral blood of patients with metastatic breast cancer: A validation study of the CellSearch system, Clinical Cancer Research, 2007, 920-928, vol. 13.
June, Carl H., Adoptive T cell therapy for cancer in the clinic, The Journal of Clinical Investigation, 2007, 1466-1476, vol. 117.
Pamme, Nicole, Continuous flow separations in microfluidic devices, Lab on a Chip, 2007, 1644-1659, vol. 7.
Riley et al., Human T regulatory cell therapy: Take a billion or so and call me in the morning, Immunity, 2009, 656-665, vol. 30.
Tsutsui et al., Cell separation by non-inertial force fields in microfluidic systems, Mechanics Research Communications, 2009, 92-103, vol. 36.
Lenshof, Andreas, Acoustic standing wave manipulation of particles and cells in microfluidic chips, Doctoral Thesis, 2009, Lund University, Lund, Sweden.
Yu et al., Circulating tumor cells: approaches to isolation and characterization, The Journal of Cell Biology, 2018, 373-382, vol. 192.
Utz et al., Microfluidic waves, Lab on a Chip, 2011, 3846-3854, vol. 11.
Dykes et al., Efficient removal of platelets from peripheral blood progenitor cell products using a novel micro-chip based acoustophoretic platform, PLOS One, 2011, e23074, vol. 6.
Augustsson et al., Microfluidic label-free enrichment of prostate cancer cells in blood based on acoustophoresis, Analytical Chemistry, 2012, 7954-7962, vol. 84.
Kandilov et al., The national market for medicare clinical laboratory testing: implications for payment reform, Medicare & Medicaid Research Review, 2012, e1-e21, vol. 2.
Barnkob et al., Acoustic radiation- and streaming-induced microparticle velocities determined by micro-PIV in an ultrasound symmetry plane, Physical Review E, 2012, 056307, vol. 86.
Tajudin et al., Integrated acoustic immunoaffinity-capture (IAI) platform for detection of PSA from whole blood samples, Lab on a Chip, 2013, 1790-1796, vol. 13.
Burguillos et al., Microchannel acoustophoresis does not impact survival or function of microglia, leukocytes or tumor cells, PLOS One, 2013, e64233, vol. 8.
Singh et al., Manufacture of clinical-grade CD 19-specific T cells stably expressing chimeric antigen receptor using sleeping beauty system and artificial antigen presenting cells, PLOS One, 2013, e64138, vol. 8.
Lenshof et al., Efficient purification of CD4+ lymphocytes from peripheral blood progenitor cell products using affinity bead acoustophoresis, Cytometry Part A, 2014, 933-941, vol. 85A.
Ilie et al., "Sentinel" circulating tumor cells allow early diagnosis of lung cancer in patients with chronic obstructive pulmonary disease, PLOS One, 2014, e111597, vol. 9.
Matsueda et al., Immunotherapy in gastric cancer, World Journal of Gastroenterology, 2014, 1657-1666, vol. 20.
Grenvall et al., Concurrent isolation of lymphocytes and granulocytes using prefocused free flow acoustophoresis, Analytical Chemistry, 2015, 5596-5604, vol. 87.
Jakobsson et al., Thousand-fold volumetric concentration of live cells with a recirculating acoustofluidic device, Analytical Chemistry, 2015, 8497-8502, vol. 87.
Fong et al., A microfluidic platform for precision small-volume sample processing and its use to size separate biological particles with an acoustic microdevice, Journal of Visualized Experiments, 2015, e53051, vol. 105.
Shields et al., Microfluidic cell sorting: a review of the advances in the separation of cells from debulking to rare cell isolation, Lab on a Chip, 2015, 1230-1249, vol. 15.
Temiz et al., Lab-on-a-chip devices: how to close and plug the lab?, Microelectronic Engineering, 2015, 156-175, vol. 132.
Hahn et al., A numerically efficient damping model for acoustic resonances in microfluidic cavities, Physics of Fluids, 2015, 062005, vol. 27.
Poruk et al., Circulating tumor cell phenotype predicts recurrence and survival in pancreatic adenocarcinoma, Annals of Surgery, 2016, 1073-1081, vol. 264.
Jansson et al., Prognostic impact of circulating tumor cell apoptosis and clusters in serial blood samples from patients with metastatic breast cancer in a prospective observational cohort, BMC Cancer, 2016, 433, vol. 16.
Banys-Paluchowski et al., Circulating tumor cells in breast cancer—current status and perspectives, Critical Reviews in Oncology/Hematology, 2016, 22-29, vol. 97.
Urbansky et al., Affinity-bead-mediated enrichment of CD8+ lymphocytes from peripheral blood progenitor cell products using acoustophoresis, Micromachines, 2016, 101, vol. 7.
Chen et al., Cancer statistics in China, 2015, CA: A Cancer Journal for Clinicians, 2016, 115-132, vol. 66.
Magnusson et al., Clinical-scale cell-surface-marker independent acoustic microfluidic enrichment of tumor cells from blood, Analytical Chemistry, 2017, 11954-11961, vol. 89.
Boffa et al., Cellular expression of PD-L1 in the peripheral blood of lung cancer patients is associated with worse survival, Cancer Epidemiology, Biomarkers & Prevention, 2017, 1139-1145, vol. 26.
Cui, Mingyang, Particle enrichment in longitudinal standing bulk acoustic wave microfluidics, Master Thesis, 2017, Washington University, St. Louis, Missouri.
Eyer et al., Single-cell deep phenotyping of IgG-secreting cells for high-resolution immune monitoring, Nature Biotechnology, 2017, 977-982, vol. 35.
Fachin et al., Monolithic chip for high-throughput blood cell depletion to sort rare circulating tumor cells, Scientific Reports, 2017, 10936, vol. 7.
Cushing et al., Reducing WBC background in cancer cell separation products by negative acoustic contrast particle immuno-acoustophoresis, Analytica Chimica Acta, 2018, 256-264, vol. 1000.
Vormittag et al., A guide to manufacturing CAR T cell therapies, Current Opinion in Biotechnology, 2018, 164-181, vol. 53.
Yu et al., An integrated enrichment system to facilitate isolation and molecular characterization of single cancer cells from whole blood, Cytometry Part A, 2018, 1226-1233, vol. 93A.
Leipold et al., Comparison of CyTOF assays across sites: Results of a six-center pilot study, Journal of Immunological Methods, 2018, 37-43, vol. 453.
Abdlaty et al., Hyperspectral imaging: comparison of acousto-optic and liquid crystal tunable filters, Proceedings of SPIE, Medical Imaging 2018: Physics of Medical Imaging, 105732P, vol. 10573.
Bhagwat et al., An integrated flow cytometry-based platform for isolation and molecular characterization of circulating tumor single cells and clusters, Scientific Reports, 2018, 5035, vol. 8.
Kulasinghe et al., Capture of circulating tumor cell clusters using straight microfluidic chips, Cancers, 2019, 89, vol. 11.
Das et al., Naive T cell deficits at diagnosis and after chemotherapy impair cell therapy potential in pediatric cancers, Cancer Discovery, 2019, 492-499, vol. 9.
Chen et al., Next-generation sequencing in liquid biopsy: cancer screening and early detection, Human Genomics, 2019, 34, vol. 13.

(56) References Cited

OTHER PUBLICATIONS

Nilsson et al., Acoustic control of suspended particles in micro fluidic chips, Lab on a Chip, 2004, 131-135, vol. 4.

Petersson et al., Free flow acoustophoresis: microfluidic-based mode of particle and cell separation, Analytical Chemistry, 2007, 5117-5123, vol. 79.

Adams et al., Integrated acoustic and magnetic separation in microfluidic channels, Applied Physics Letters, 2009, 254103, vol. 95.

Adams et al., Tunable acoustophoretic band-pass particle sorter, Applied Physics Letters, 2010, 064103, vol. 97.

Guldiken et al., Sheathless size-based acoustic particle separation, Sensors, 2012, 905-922, vol. 12.

Glynne-Jones et al., Acoustofluidic 23: acoustic manipulation combined with other force fields, Lab on a Chip, 2013, 1003-1010, vol. 13.

Sajeesh et al., Particle separation and sorting in microfluidic devices: a review, Microfluidic Nanofluidic, 2014, 1-52, vol. 17.

Watarai, Hitoshi, Continuous separation principles using external microaction forces, Annual Review of Analytical Chemistry, 2013, 353-378, vol. 6.

Van Assche et al., Gradient acoustic focusing of submicron particles for separation of bacteria from blood lysate, Scientific reports, 2020, 3670, vol. 10.

Antfolk et al., Label-free single-cell separation and imaging of cancer cells using an integrated microfluidic system, 2017, 46507, vol. 7.

Racila et al., Detection and characterization of carcinoma cells in the blood, Medical Sciences, 1998, 4589-4594, vol. 95.

Benez et al., Detection of circulating melanoma cells by immunomagnetic cell sorting, Journal of Clinical Laboratory Analysis, 1999, 229-233, vol. 13.

Iinuma et al., Detection of tumor cells in blood using CD45 magnetic cell separation followed by nested mutant allele-specific amplification of p53 and K-ras genes in patients with colorectal cancer, International Journal of Cancer, 2000, 337-344, vol. 89.

Urbansky et al., Label-free separation of leukocyte subpopulations using high throughput multiplex acoustophoresis, Lab on a Chip, 2019, 1406, vol. 19.

Chemi et al., Pulmonary venous circulating tumor cell dissemination before tumor resection and disease relapse, Nature Medicine, 2019, 1534-1539, vol. 25.

Liu et al., Epithelial-type systemic breast carcinoma cells with a restricted mesenchymal transition are a major source of metastasis, Science Advances, 2019, eaav4275, vol. 5.

Xu et al., Correlation of pulmonary venous circulating tumor cells with clinicopathological parameters in patients with early-stage lung adenocarcinoma, Translational Cancer Research, 2019, 887-898, vol. 8.

Daieff, Marine, Acoustic techniques for microfluidic particle sorting, Elveflow Product Brochure, 2020.

Olm, Franziska, Label-free processing of stem cell preparations by acoustophoresis, Doctoral Thesis, Lund University, 2020, Lund, Sweden.

Goda, Keisuke, Intelligent image-activated cell sorting: a tutorial, Handout from International Society for Advancement of Cytometry Webinar on Jan. 8, 2020.

Second-generation micro actuator for better head-positioning accuracy, Hitachi Global Storage Technology Tech Brief, 2017.

Ott et al., An ongoing analysis of a phase IB study of the personal neoantigen vaccine NEO-PV-01 + Nivolumab in patients with metastatic melanoma, NSCLC and bladder cancer, Handout from ESMO Congress, Munich, 2018.

Yasutaka et al., Dual-stage actuator for HDD achieving high-accuracy positioning and wide-bandwidth servo control, Toshiba Review, 2011, vol. 66.

* cited by examiner

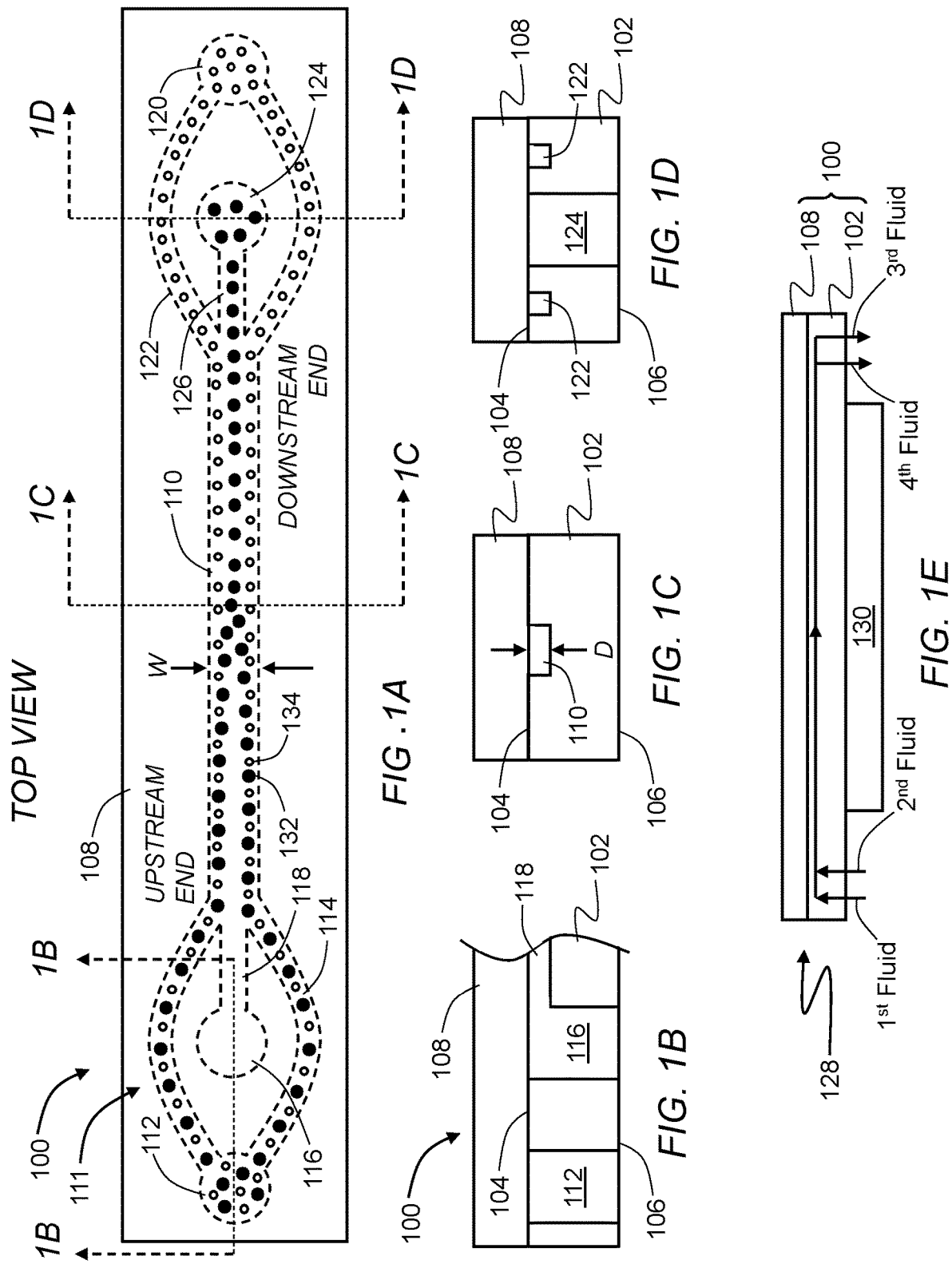

CROSS-SECTIONAL VIEWS
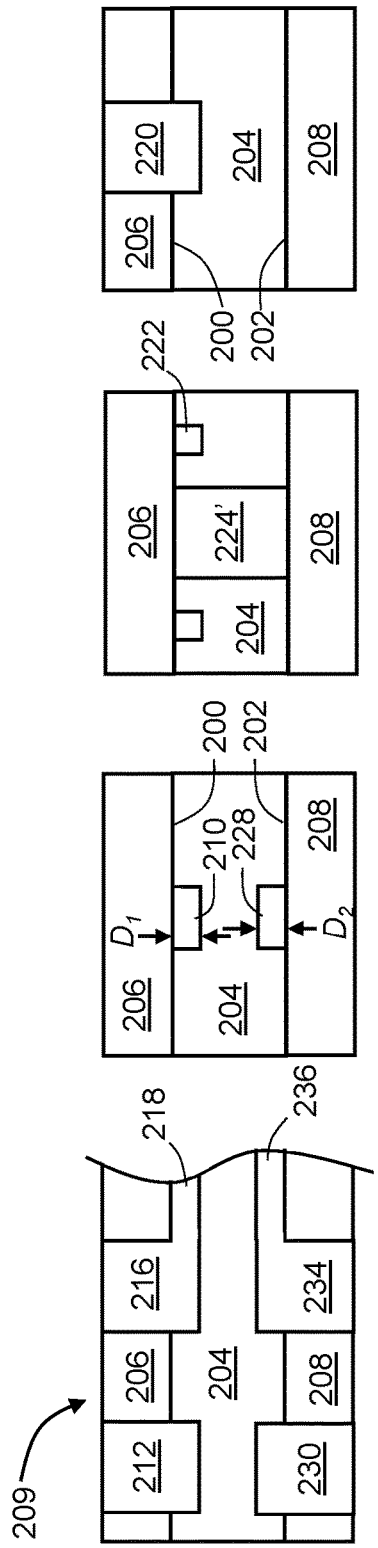
FIG. 2C
FIG. 2D
FIG. 2E
FIG. 2F
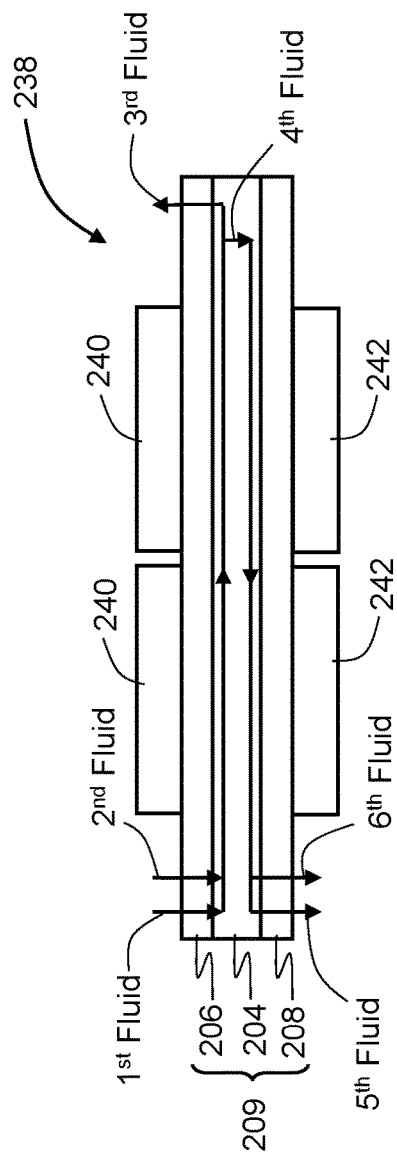
FIG. 2G

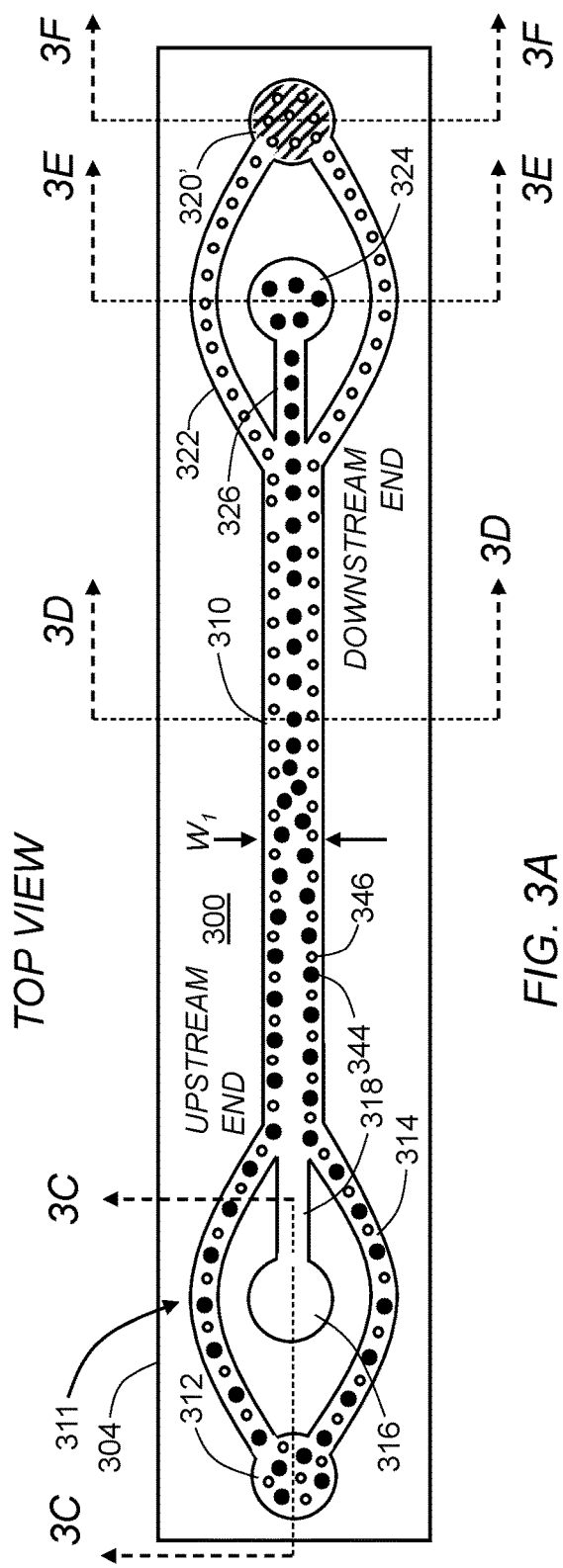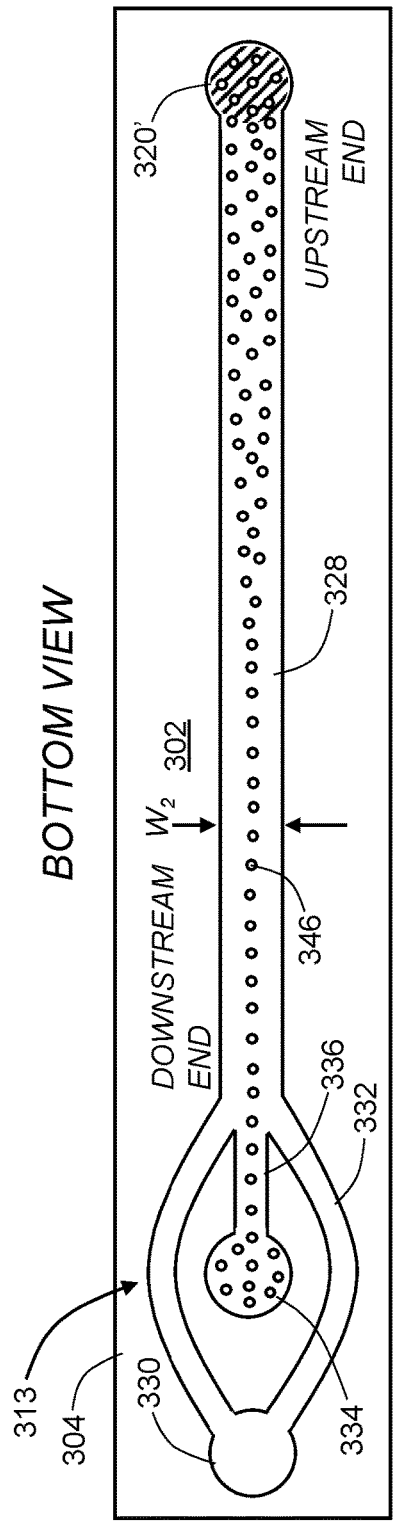
FIG. 3A
FIG. 3B

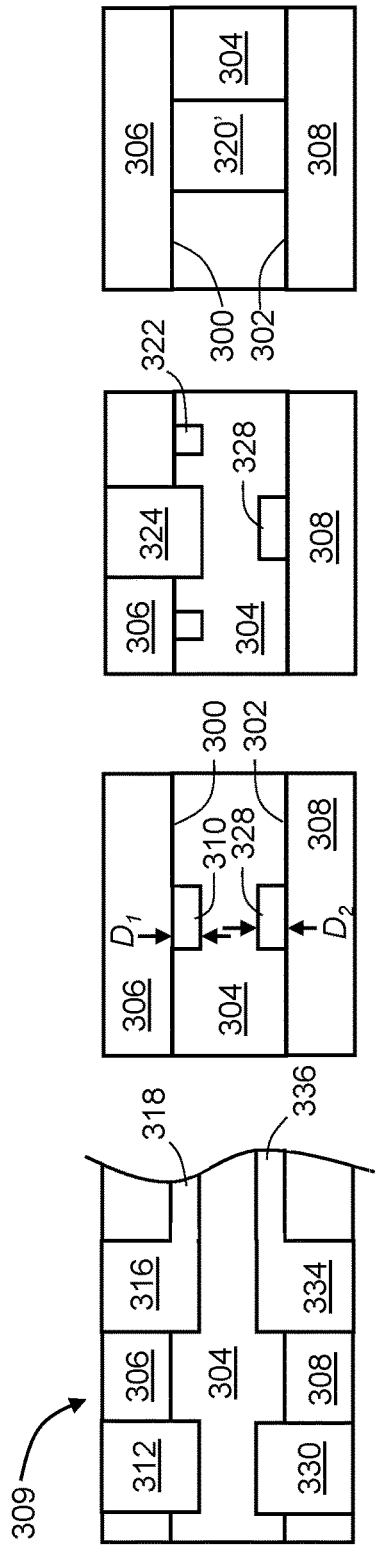

CROSS-SECTIONAL VIEWS
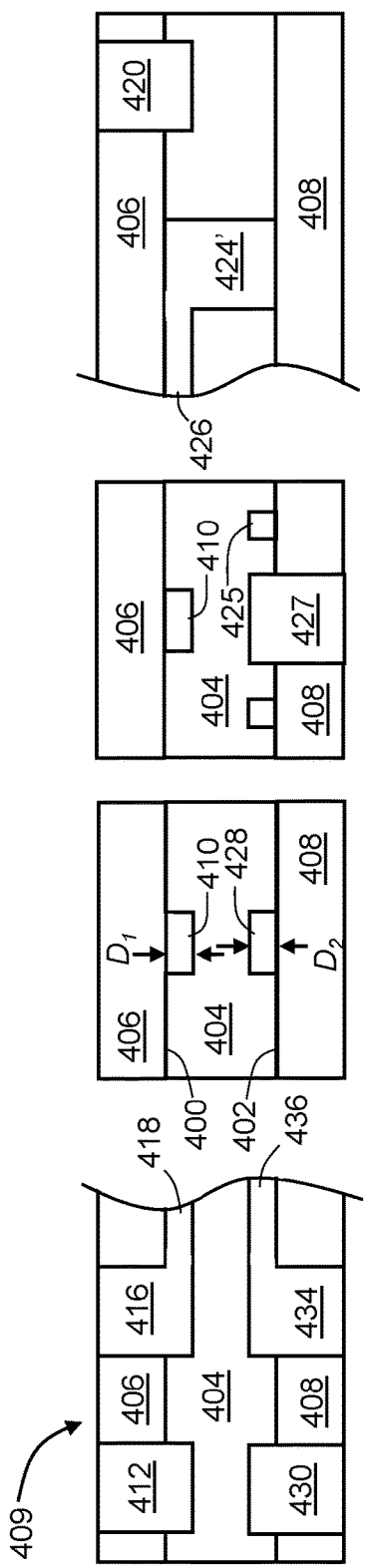
FIG. 4C
FIG. 4D
FIG. 4E
FIG. 4F
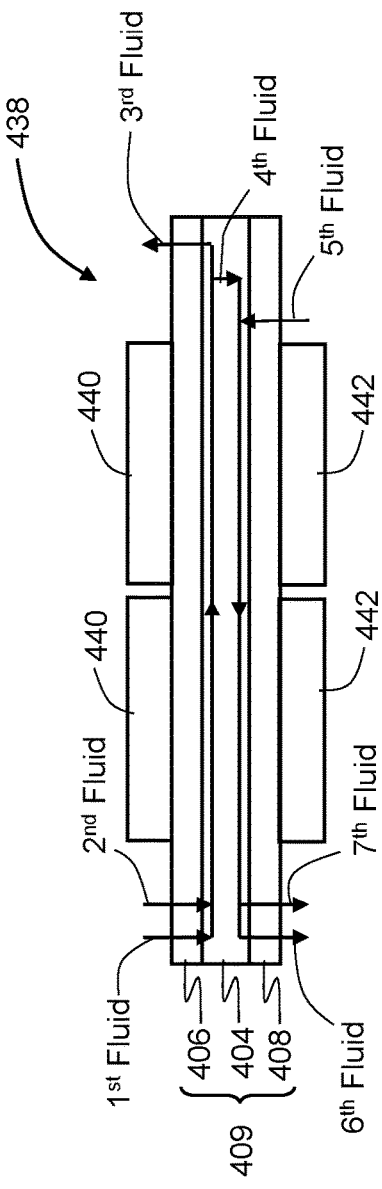
FIG. 4G

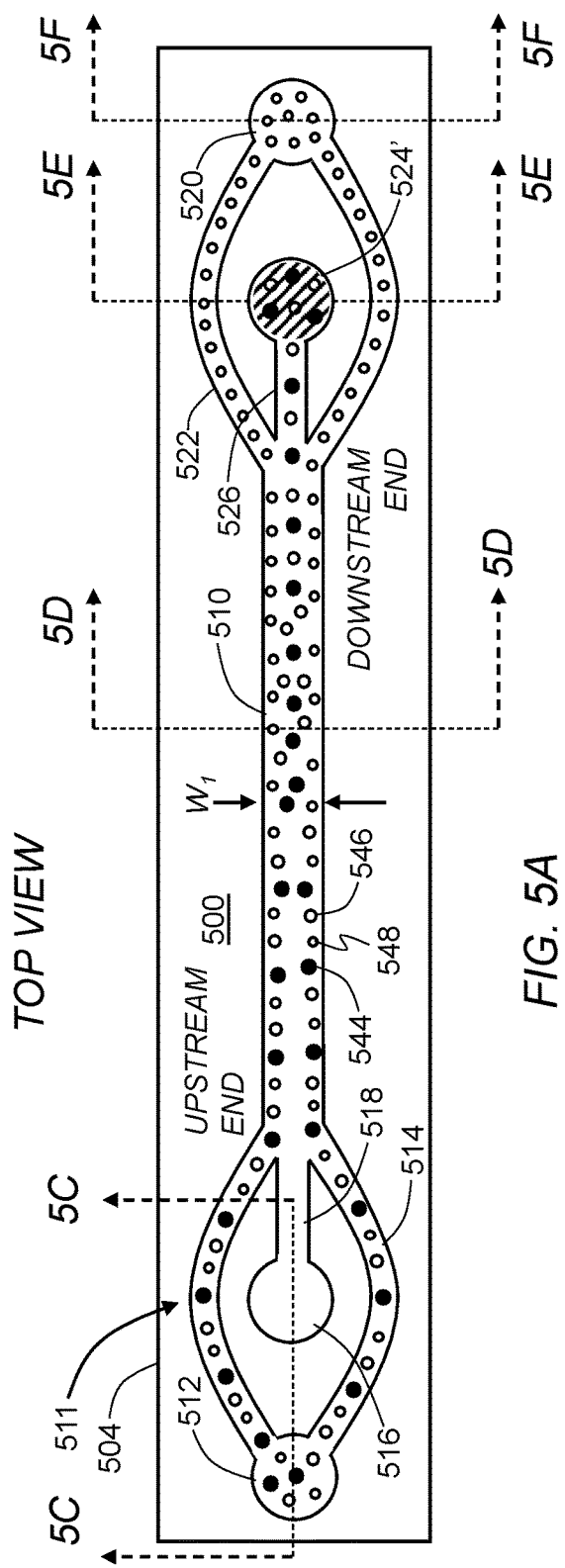
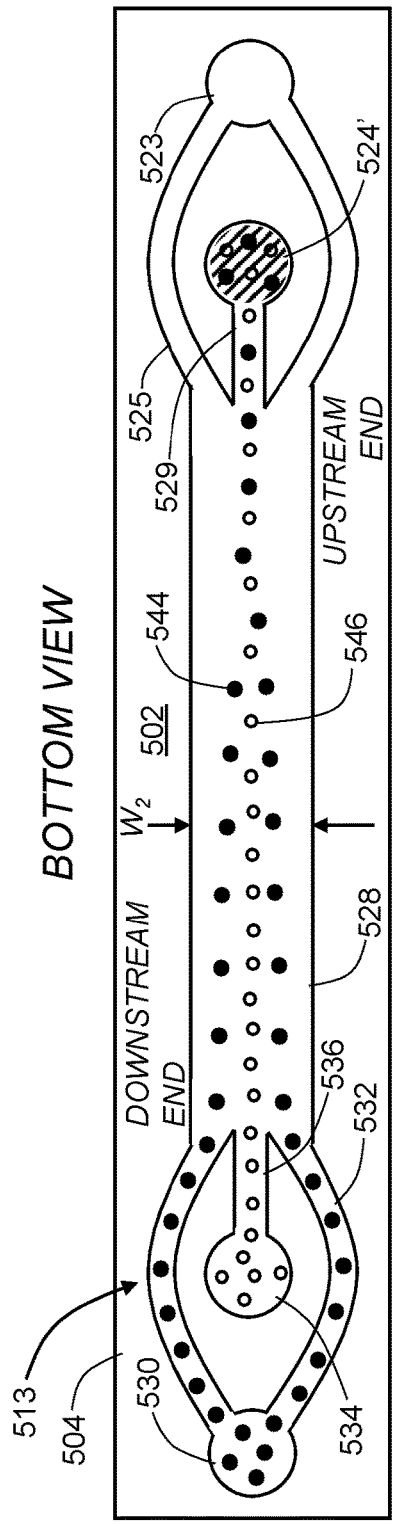
FIG. 5A
FIG. 5B

CROSS-SECTIONAL VIEWS
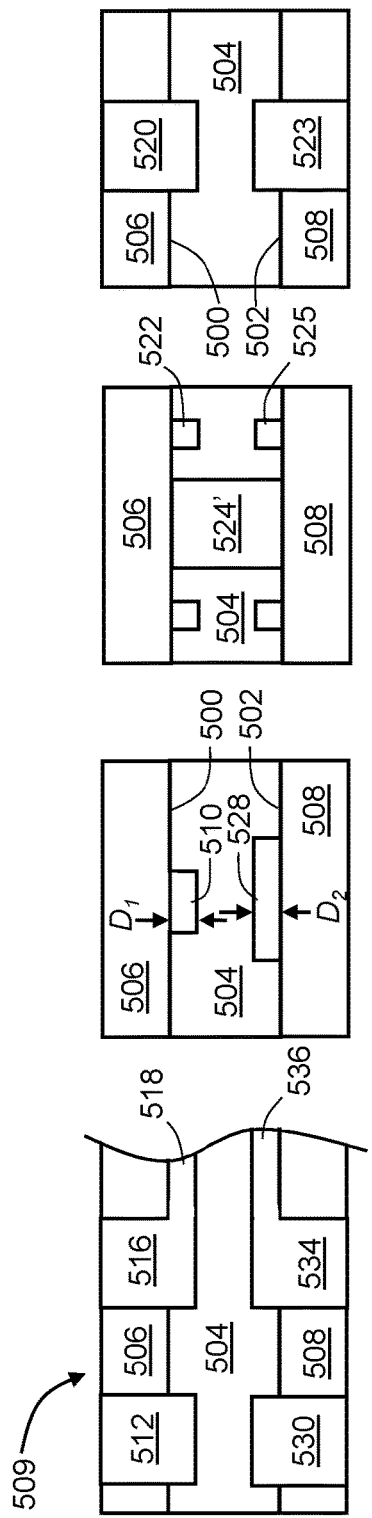
FIG. 5C
FIG. 5D
FIG. 5E
FIG. 5F
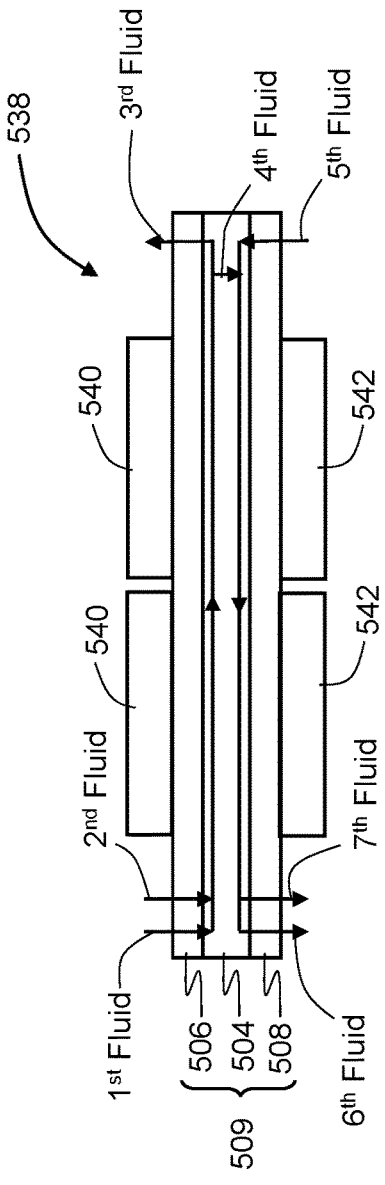
FIG. 5G

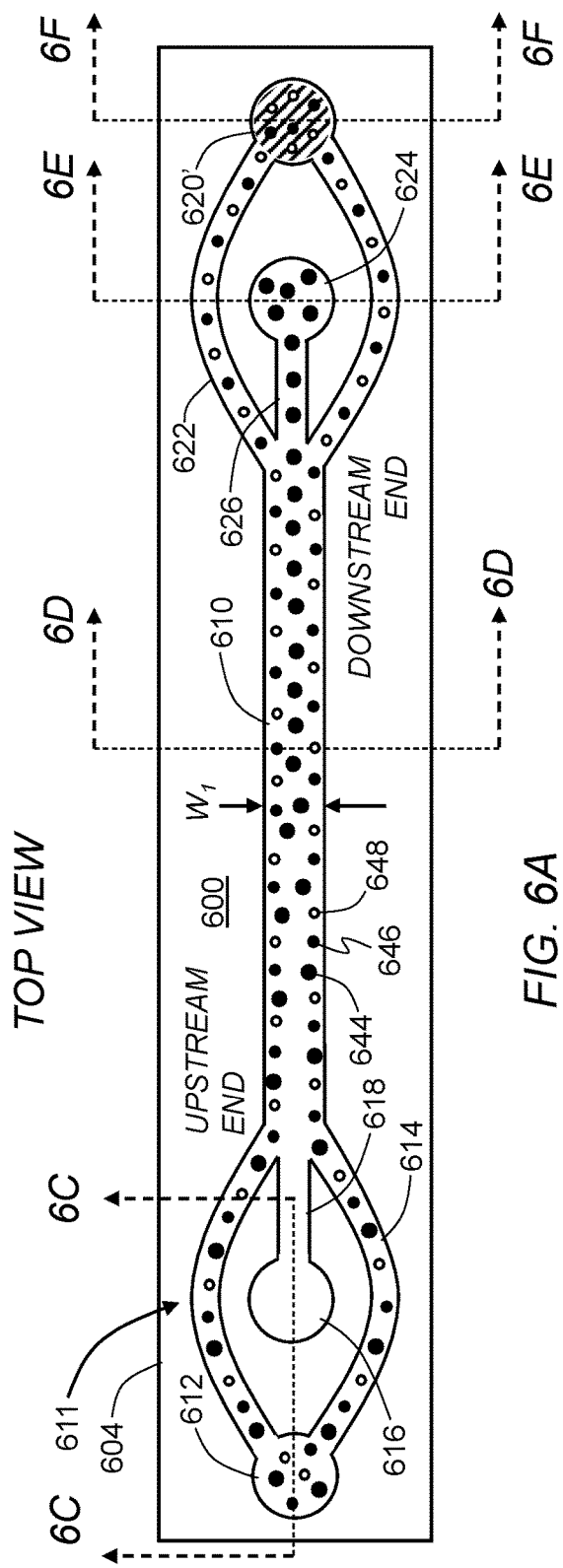
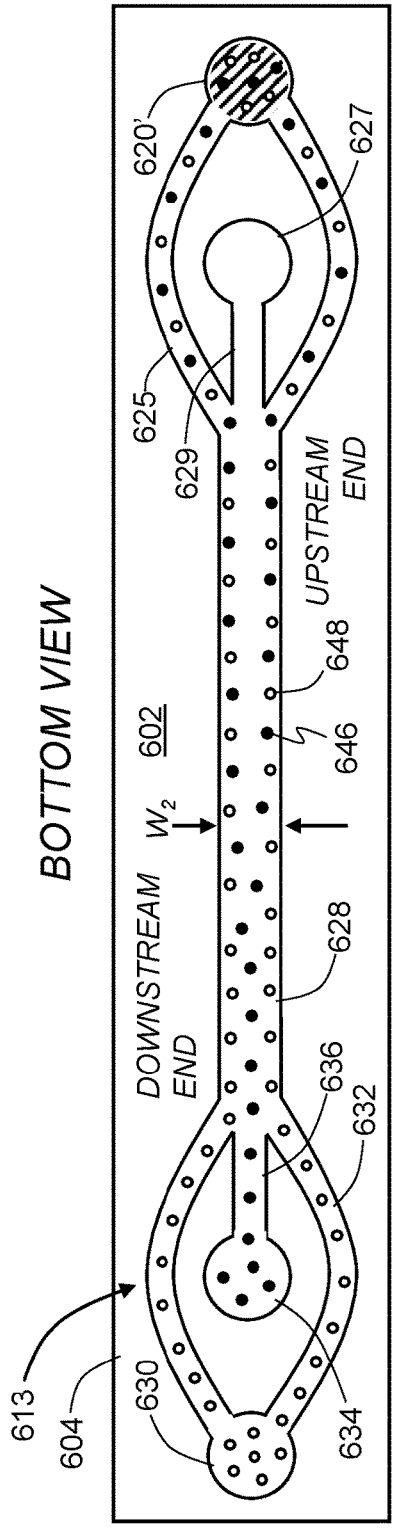
FIG. 6A
FIG. 6B

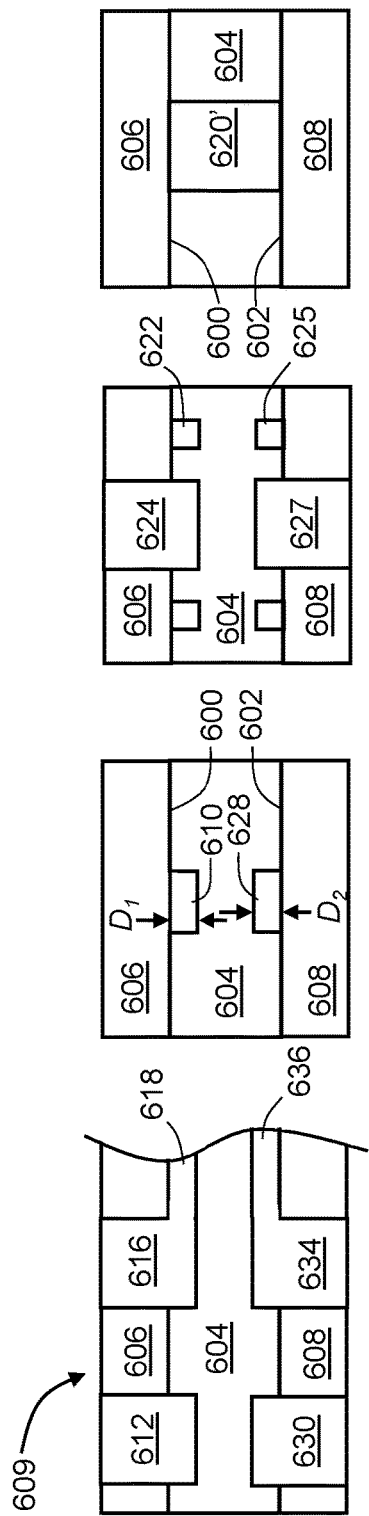
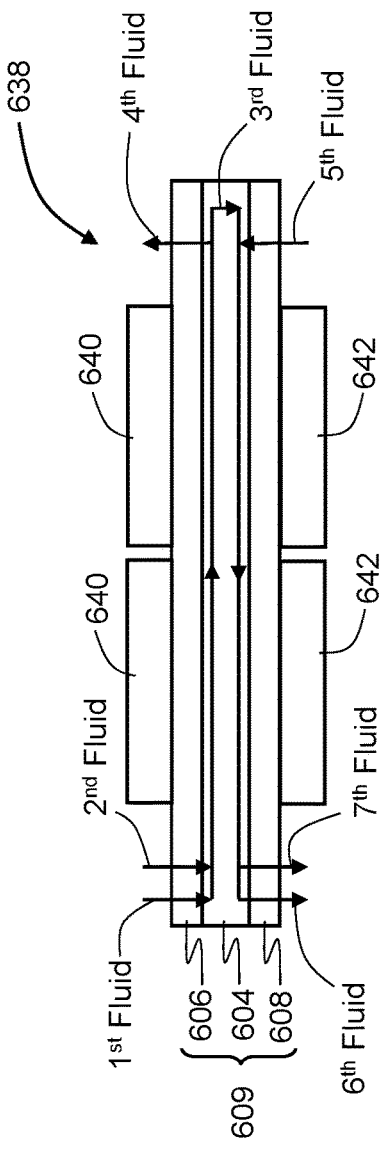
CROSS-SECTIONAL VIEWS
FIG. 6C
FIG. 6D
FIG. 6E
FIG. 6F
FIG. 6G

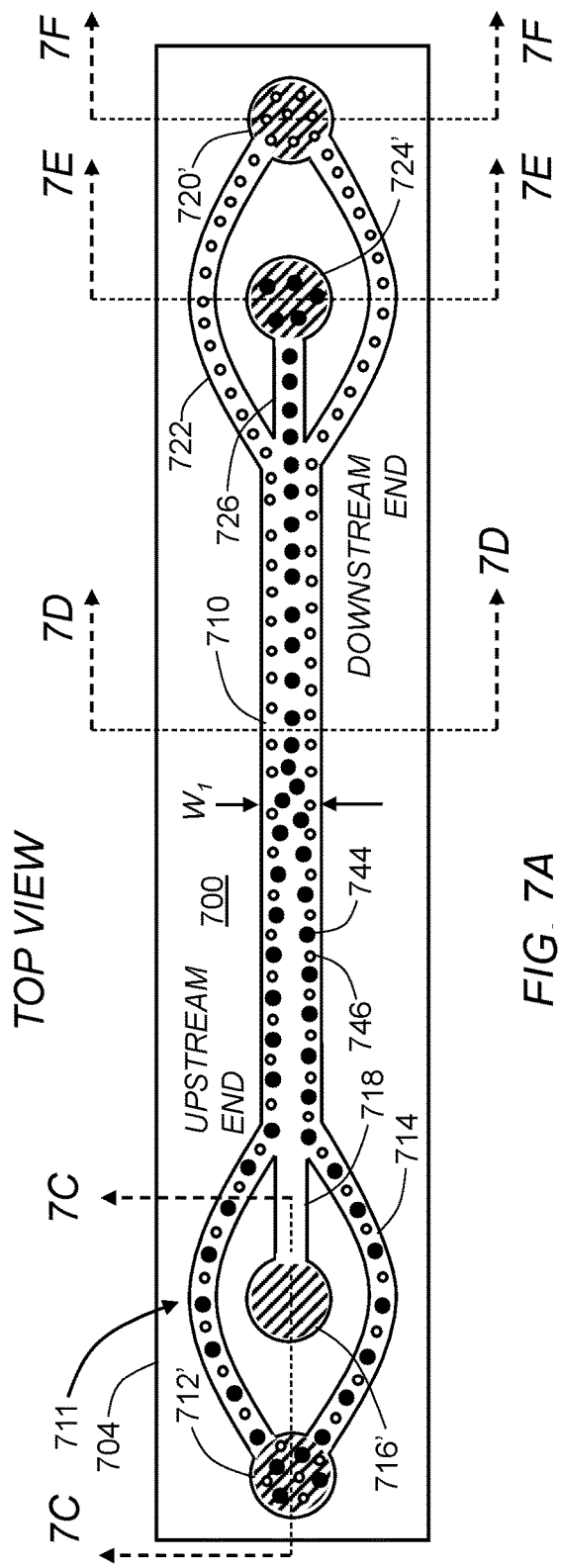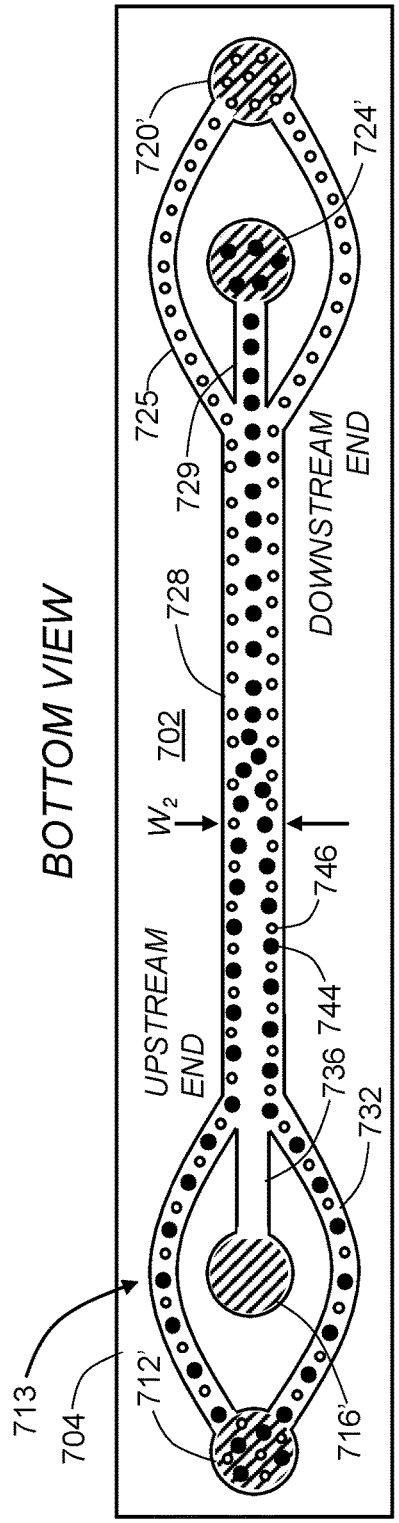
FIG. 7A
FIG. 7B

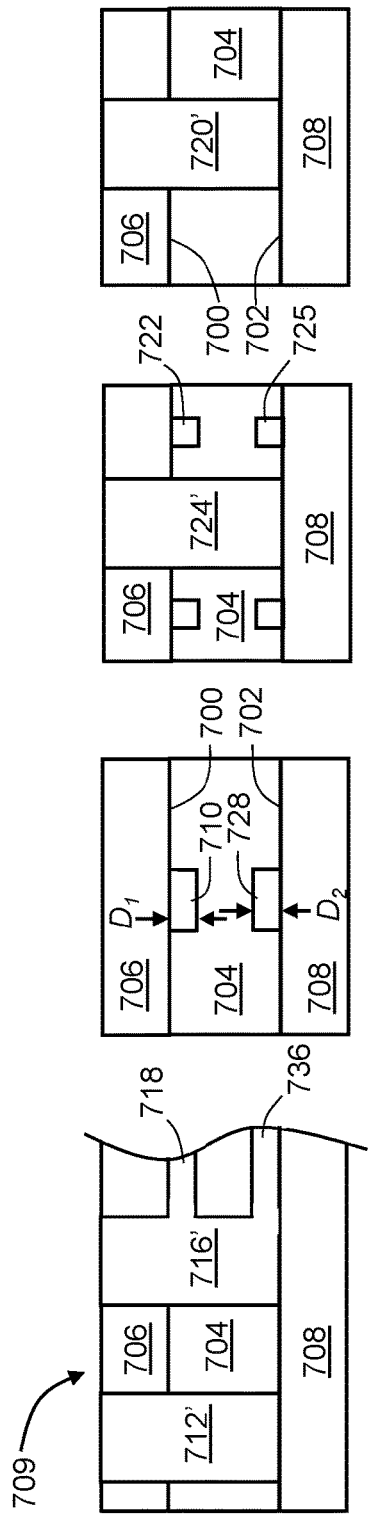

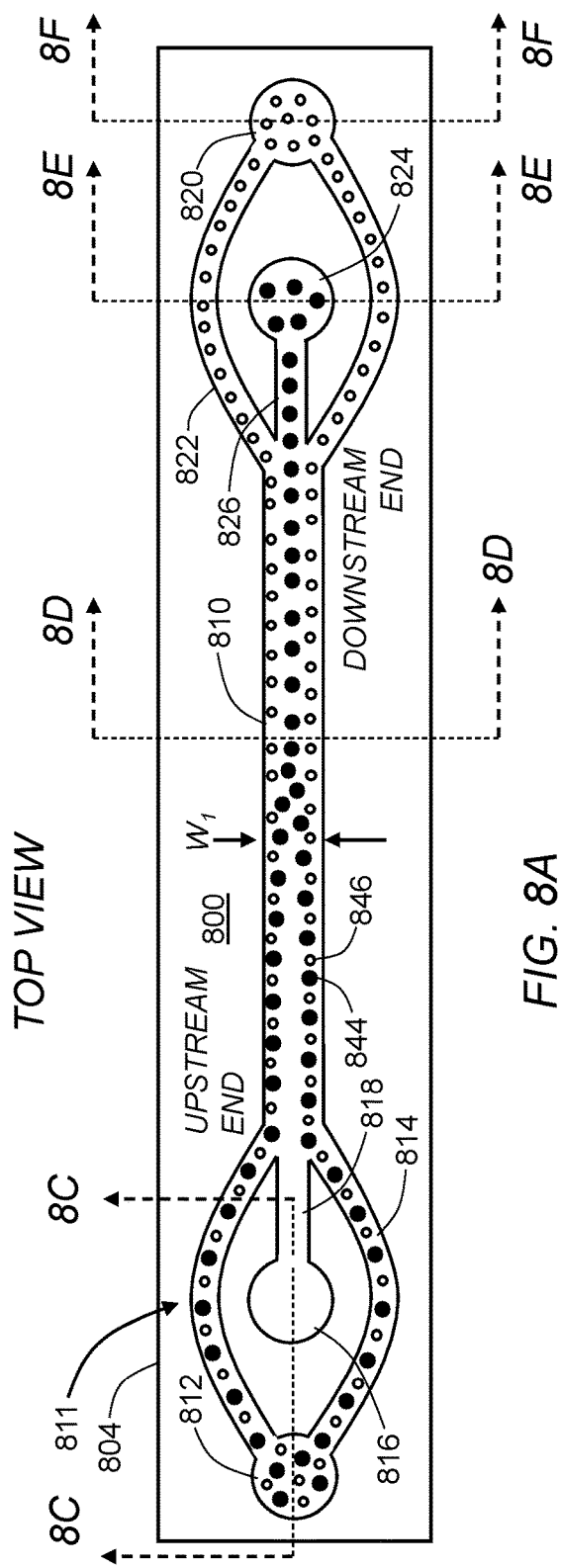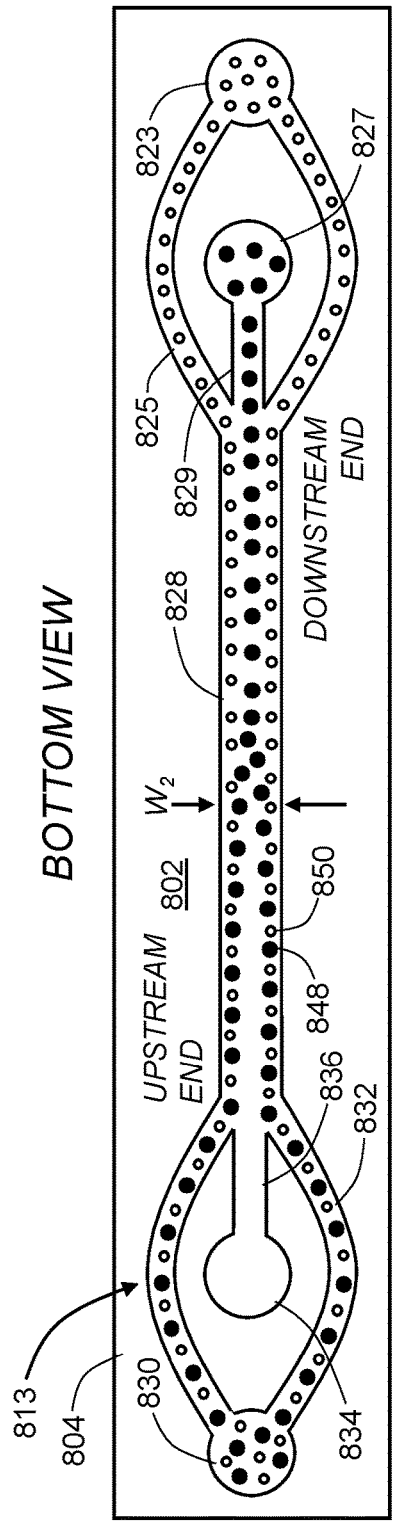

CROSS-SECTIONAL VIEWS
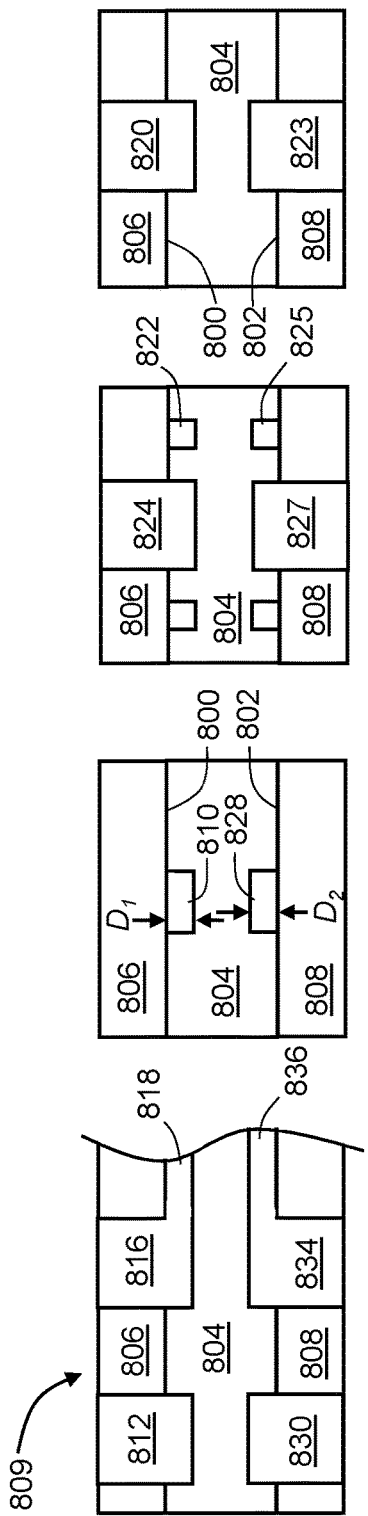
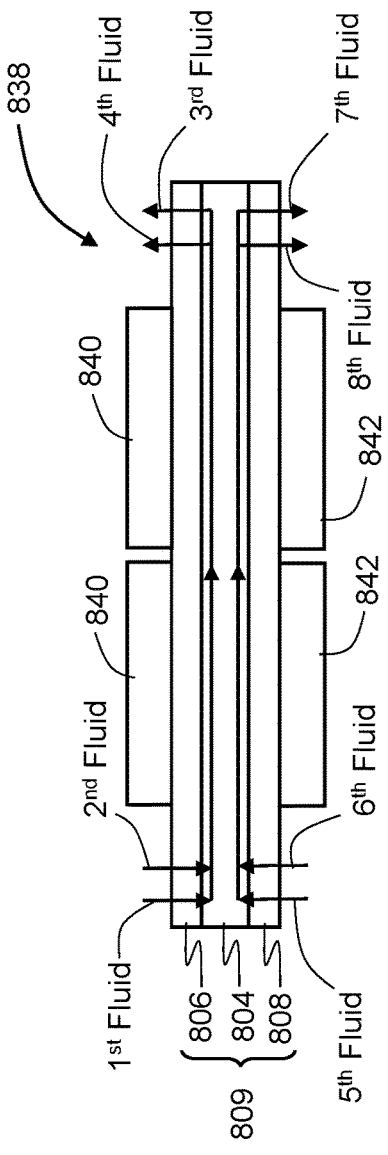

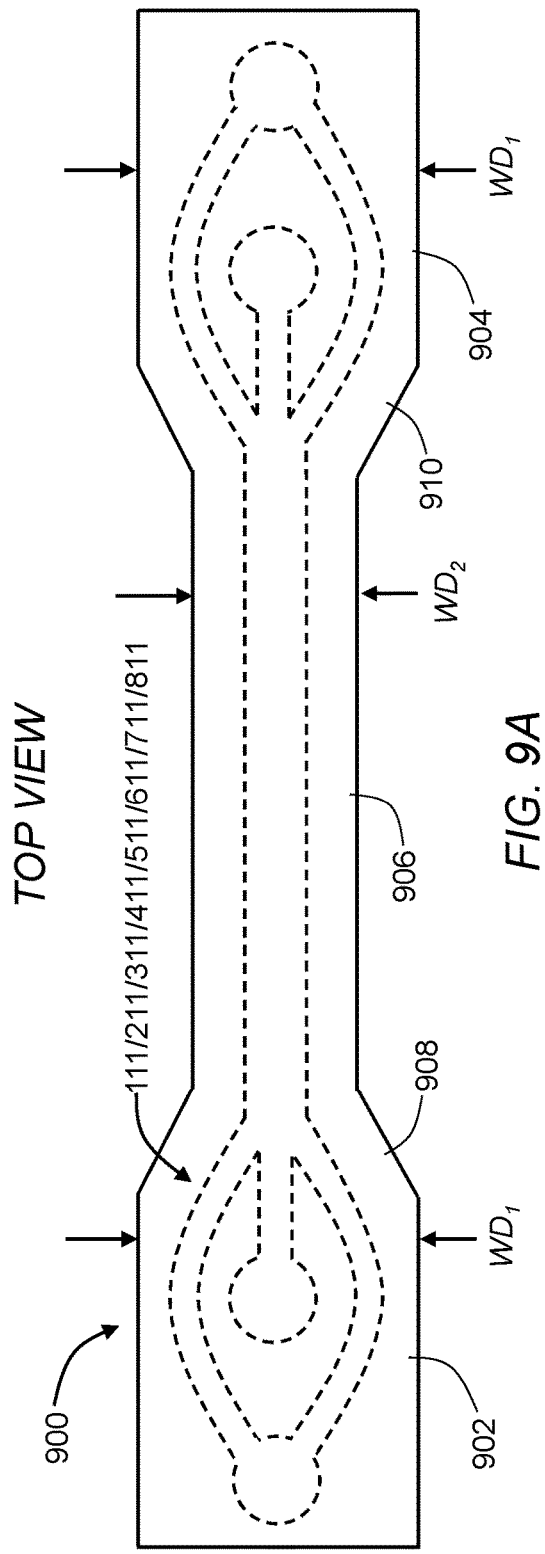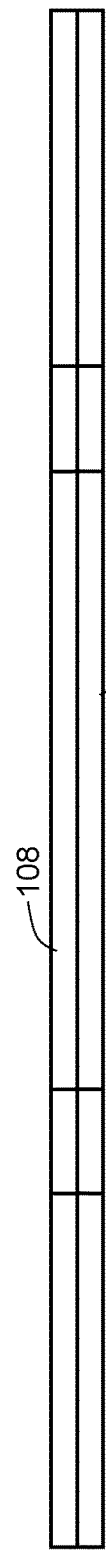

MICROFLUIDIC CHIP FOR ACOUSTIC SEPARATION OF BIOLOGICAL OBJECTS

BACKGROUND

The present invention relates to microfluidic devices, and more particularly, to microfluidic chips designed for acoustic separation of biological objects or particles.

Acoustic particle separation method for sorting or separating various biological objects from a fluid sample, such as blood, is of great interest in biological and biomedical applications. The method, which does not require labeling of biological objects, uses acoustic radiation pressure to separate particles or biological objects suspended in a fluid by size or acoustic contrast as they flow through the separation channel in a microfluidic device. The microfluidic device may include other auxiliary functionalities, such as pre-alignment and concentration of biological objects. U.S. Pat. No. 9,656,263 discloses a microfluidic device including a pre-alignment channel fluidically connected to a separation channel. Antfolk et al. (Acoustofluidic, label-free separation and simultaneous concentration of rare tumor cells from white blood cells, Analytical Chemistry 87, 9322-9328, (2015)) disclose a microfluidic device including a separation channel fluidically connected to a concentration channel for removing excess fluid from the sorted sample. Adams et al. (Tunable acoustophoretic band-pass particle sorter, Applied Physics Letters 97, 064103 (2010)) disclose a microfluidic device including two separation channels fluidically connected in series.

The network of channels for acoustic separation in a microfluidic device is typically etched into a silicon substrate and sealed with a glass lid. Therefore, the microfluidic device is normally in the form of an elongated chip, which is fragile compared with conventional semiconductor chips. The microfluidic chip may have a length-to-width aspect ratio of 10 to 20 and a length-to-thickness aspect ratio of 100 or less.

As understood by those skilled in the art, the performance of the separation channel, pre-alignment channel, and concentration channel correlates to the channel length. When multiple channels are integrated into a microfluidic chip, however, the length of each channel may be limited owing to the limitation on the overall length of the microfluidic chip.

For the foregoing reasons, there is a need for a microfluidic chip that includes multiple fluidic channels without compromising their performance.

SUMMARY

The present invention is directed to a device that satisfies this need. A microfluidic device having features of the present invention for sorting biological objects comprises a microfluidic chip including a planar substrate, which has a first planar surface and a second planar surface opposite the first planar surface, that includes first and second networks of channels recessed respectively from the first and second planar surfaces and fluidically connected in series or parallel by way of at least a through-hole in the planar substrate; a first lid attached to the first planar surface of the planar substrate and substantially covering the first network of channels; and a second lid attached to the second planar surface of the planar substrate and substantially covering the second network of channels; one or more first piezoelectric transducers attached to an exterior of the first lid and configured to generate a first acoustic standing wave having a first wavelength in a first linear channel of the first network of channels; and one or more second piezoelectric transducers attached to an exterior of the second lid and configured to generate a second acoustic standing wave having a second wavelength in a second linear channel of the second network of channels.

According to another aspect of the present invention, a microfluidic device having features of the present invention for sorting biological objects comprises a microfluidic chip including a planar substrate, which has a first planar surface and a second planar surface opposite the first planar surface, that includes first and second networks of channels recessed respectively from the first and second planar surfaces and fluidically connected in series or parallel by way of at least a through-hole in the planar substrate; a first lid attached to the first planar surface of the planar substrate and substantially covering the first network of channels; and a second lid attached to the second planar surface of the planar substrate and substantially covering the second network of channels; one or more first piezoelectric transducers attached to an exterior of the first lid and configured to generate a first acoustic standing wave having a first wavelength in a first linear channel of the first network of channels; and one or more second piezoelectric transducers attached to an exterior of the second lid and configured to generate a second acoustic standing wave having a second wavelength in a second linear channel of the second network of channels. The first network of channels includes the first linear channel having upstream and downstream ends and a first width; a first port opened to an exterior of the first lid; a first pair of side channels connecting the first port to the first linear channel at the upstream end thereof; a second port opened to the exterior of the first lid and fluidically connected to the first linear channel at the upstream end thereof; and a third port opened to the second planar surface by way of the through-hole and fluidically connected to the first linear channel at the downstream end thereof. The second network of channels includes a second linear channel having upstream and downstream ends and a second width; a fourth port opened to the first planar surface by way of the through-hole and fluidically connected to the second linear channel at the upstream end thereof; a fifth port opened to an exterior of the second lid; a second pair of side channels connecting the fifth port to the second linear channel at the downstream end thereof; and a sixth port opened to the exterior of the second lid and fluidically connected to the second linear channel at the downstream end thereof. The planar substrate, the first lid, and the second lid have a barbell shape that is characterized by two wide end sections and a narrow center section interposed therebetween.

According to still another aspect of the present invention, a microfluidic device having features of the present invention for sorting biological objects comprises a microfluidic chip including a planar substrate, which has a first planar surface and a second planar surface opposite the first planar surface, that includes first and second networks of channels recessed respectively from the first and second planar surfaces and fluidically connected in series or parallel by way of at least a through-hole in the planar substrate; a first lid attached to the first planar surface of the planar substrate and substantially covering the first network of channels; and a second lid attached to the second planar surface of the planar substrate and substantially covering the second network of channels; one or more first piezoelectric transducers attached to an exterior of the first lid and configured to generate a first acoustic standing wave having a first wavelength in a first linear channel of the first network of channels; and one or more second piezoelectric transducers attached to an exterior of the second lid and configured to generate a second acoustic standing wave having a second wavelength in a second linear channel of the second network of channels. The first network of channels includes the first linear channel having upstream and downstream ends and a first width; a first port opened to the second planar surface by way of a first through-hole in the planar substrate; a first pair of side channels connecting the first port to the first linear channel at the upstream end thereof; a second port opened to the second planar surface by way of a second through-hole in the planar substrate; a first center channel connecting the second port to the first linear channel at the upstream end thereof; a third port opened to the second planar surface by way of a third through-hole in the planar substrate; a second pair of side channels connecting the third port to the first linear channel at the downstream end thereof; and a fourth port opened to the second planar surface by way of a fourth through-hole in the planar substrate and fluidically connected to the first linear channel at the downstream end thereof. The second network of channels includes a second linear channel having upstream and downstream ends and a second width; a fifth port opened to the first planar surface by way of the first through-hole; a third pair of side channels connecting the fifth port to the second linear channel at the upstream end thereof; a sixth port opened to the first planar surface by way of the second through-hole; a second center channel connecting the sixth port to the second linear channel at the upstream end thereof; a seventh port opened to the first planar surface by way of the third through-hole; a fourth pair of side channels connecting the seventh port to the second linear channel at the downstream end thereof; and an eighth port opened to the first planar surface by way of the fourth through-hole and fluidically connected to the second linear channel at the downstream end thereof. Each of the first, second, third, and fourth through-holes is independently opened to an exterior of the first or second lid.

BRIEF DESCRIPTION OF THE DRAWINGS

These and other features, aspects, and advantages of the present invention will become better understood with regard to the following description, appended claims, and accompanying drawings where:

FIG. 1A is a top view of a microfluidic chip containing therein a network of channels;

FIGS. 1B-1D are cross-sectional views corresponding to the microfluidic chip of FIG. 1A;

FIG. 1E is a schematic diagram of a microfluidic device illustrating fluidic paths through the microfluidic chip shown in FIGS. 1A-1D;

FIGS. 2C-2F are cross-sectional views corresponding to the microfluidic chip incorporating the planar substrate shown in FIGS. 2A and 2B;

FIG. 2G is a schematic diagram of a microfluidic device illustrating fluidic paths through the microfluidic chip shown in FIGS. 2A-2F;

FIGS. 3A and 3B are, respectively, top and bottom views of a planar substrate for a microfluidic chip that contains therein first and second networks of channels in accordance with another embodiment of the present invention;

FIGS. 3C-3F are cross-sectional views corresponding to the microfluidic chip incorporating the planar substrate shown in FIGS. 3A and 3B;

FIG. 3G is a schematic diagram of a microfluidic device illustrating fluidic paths through the microfluidic chip shown in FIGS. 3A-3F;

FIGS. 4C-4F are cross-sectional views corresponding to the microfluidic chip incorporating the planar substrate shown in FIGS. 4A and 4B;

FIG. 4G is a schematic diagram of a microfluidic device illustrating fluidic paths through the microfluidic chip shown in FIGS. 4A-4F;

FIGS. 5A and 5B are, respectively, top and bottom views of a planar substrate for a microfluidic chip that contains therein first and second networks of channels in accordance with yet another embodiment of the present invention;

FIGS. 5C-5F are cross-sectional views corresponding to the microfluidic chip incorporating the planar substrate shown in FIGS. 5A and 5B;

FIG. 5G is a schematic diagram of a microfluidic device illustrating fluidic paths through the microfluidic chip shown in FIGS. 5A-5F;

FIGS. 6A and 6B are, respectively, top and bottom views of a planar substrate for a microfluidic chip that contains therein first and second networks of channels in accordance with still another embodiment of the present invention;

FIGS. 6C-6F are cross-sectional views corresponding to the microfluidic chip incorporating the planar substrate shown in FIGS. 6A and 6B;

FIG. 6G is a schematic diagram of a microfluidic device illustrating fluidic paths through the microfluidic chip shown in FIGS. 6A-6F;

FIGS. 7A and 7B are, respectively, top and bottom views of a planar substrate for a microfluidic chip that contains therein first and second networks of channels in accordance with yet another embodiment of the present invention;

FIGS. 7C-7F are cross-sectional views corresponding to the microfluidic chip incorporating the planar substrate shown in FIGS. 7A and 7B;

FIG. 7G is a schematic diagram of a microfluidic device illustrating fluidic paths through the microfluidic chip shown in FIGS. 7A-7F;

FIGS. 8A and 8B are, respectively, top and bottom views of a planar substrate for a microfluidic chip that contains therein first and second networks of channels in accordance with still another embodiment of the present invention;

FIGS. 8C-8F are cross-sectional views corresponding to the microfluidic chip incorporating the planar substrate shown in FIGS. 8A and 8B;

FIG. 8G is a schematic diagram of a microfluidic device illustrating fluidic paths through the microfluidic chip shown in FIGS. 8A-8F;

FIG. 9A is a top view of a microfluidic chip having a barbell shape; and

FIGS. 9B and 9C are side views corresponding to the microfluidic chip of FIG. 9A with one lid and two lids, respectively.

For purposes of clarity and brevity, like elements and components will bear the same designations and numbering throughout the Figures, which are not necessarily drawn to scale.

DETAILED DESCRIPTION

Figure 2A:
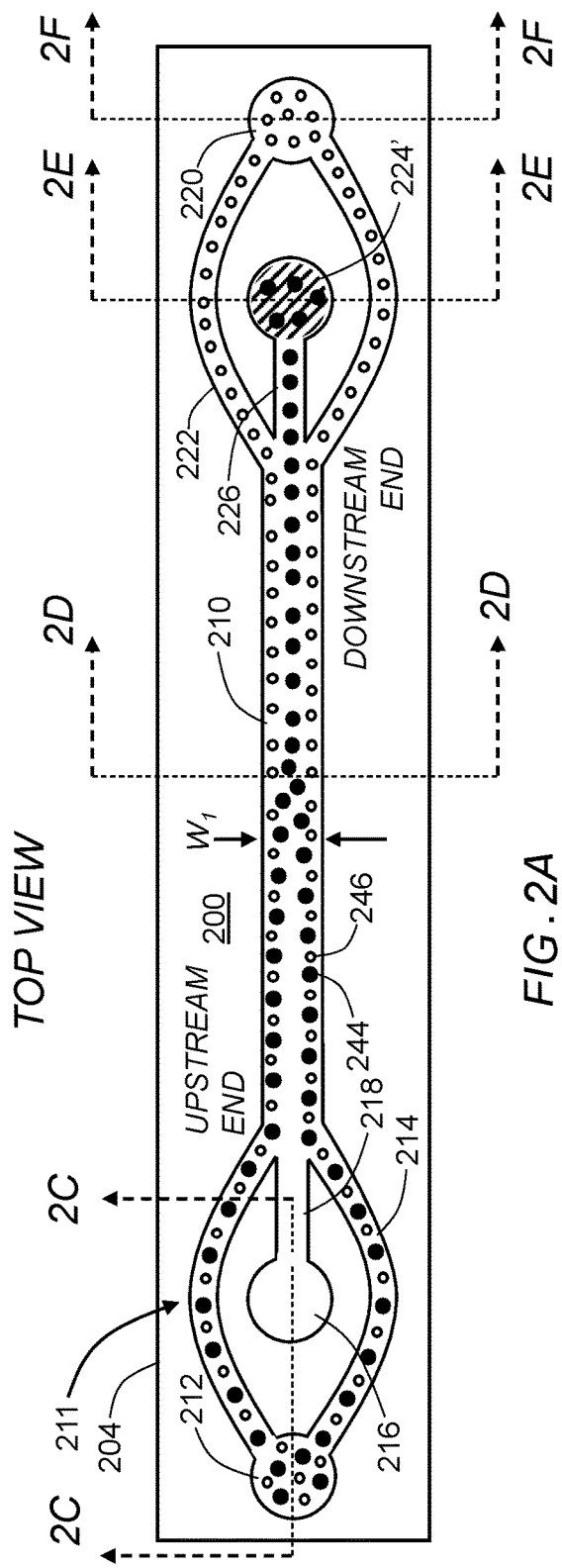
FIGS. 2A and 2B are, respectively, top and bottom views of a planar substrate for a microfluidic chip that contains therein first and second networks of channels in accordance with an embodiment of the present invention.

In the Summary above and in the Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously, except where the context excludes that possibility, and the method can include one or more other steps which are carried out before any of the defined steps, between two of the defined steps, or after all the defined steps, except where the context excludes that possibility.

The term "at least" followed by a number is used herein to denote the start of a range beginning with that number, which may be a range having an upper limit or no upper limit, depending on the variable being defined. For example, "at least 1" means 1 or more than 1. The term "at most" followed by a number is used herein to denote the end of a range ending with that number, which may be a range having 1 or 0 as its lower limit, or a range having no lower limit, depending upon the variable being defined. For example, "at most 4" means 4 or less than 4, and "at most 40%" means 40% or less than 40%. When, in this specification, a range is given as "a first number to a second number" or "a first number-a second number," this means a range whose lower limit is the first number and whose upper limit is the second number. For example, "25 to 100 nm" means a range whose lower limit is 25 nm and whose upper limit is 100 nm.

Directional terms, such as "front," "back," "top," "bottom," and the like, may be used with reference to the orientation of the illustrated figure. Spatially relative terms, such as "beneath," "below," "under," "lower," "upper," "above," etc., may be used herein to describe one element's relationship to another element(s) as illustrated in the figure. Since articles and elements can be positioned in a number of different orientations, these terms are intended for illustration purposes and in no way limit the invention, except where the context excludes that possibility.

The term "biological objects" may be used herein to include cells, bacteria, viruses, molecules, particles including RNA and DNA, cell cluster, bacteria cluster, molecule cluster, and particle cluster.

The term "biological sample" may be used herein to include blood, body fluid, tissue extracted from any part of the body, bone marrow, hair, nail, bone, tooth, liquid and solid from bodily discharge, or surface swab from any part of body. "Fluid sample," or "sample fluid," or "liquid sample," or "sample solution" may include a biological sample in its original liquid form, biological objects being dissolved or dispersed in a buffer liquid, or a biological sample dissociated from its original non-liquid form and dispersed in a buffer fluid. A buffer fluid is a liquid into which biological objects may be dissolved or dispersed without introducing contaminants or unwanted biological objects. Biological objects and biological sample may be obtained from human or animal. Biological objects may also be obtained from plants and environment including air, water, and soil. A fluid sample may contain various types of magnetic or optical labels, or one or more chemical reagents that may be added during various process steps.

The term "sample flow rate" or "flow rate" may be used herein to represent the volume amount of a fluid sample flowing through a cross section of a channel, or a fluidic part, or a fluidic path, in a unit time.

The term "relative fraction" may be used herein to represent the ratio of a given quantity of biological objects or particles to the total quantity of all biological objects or particles present in a fluid sample.

The term "acoustic contrast" is used herein to describe the relative difference in the density/compressibility ratio between an object and the host medium with regard to the ability to manipulate its position with acoustic radiation pressure. Objects having higher density/compressibility ratios than the host medium may have positive acoustic contrast, which tends to move the objects towards pressure nodes. Conversely, objects having lower density/compressibility ratios than the host medium may have negative acoustic contrast, which tends to move the objects towards pressure antinodes.

In the art of cell sorting or enrichment, the target population of biological objects is referred to as the "specific" objects of interest and those biological objects that are isolated, but are not desired, are termed "non-specific." The term "purity" describes the concentration or relative fraction of target or specific biological objects of interest and is quantified by the number of target biological objects divided by the total number of biological objects expressed in percentage. The term "recovery ratio" describes the sorting efficiency of biological objects and is quantified by the number of target biological objects recovered after sorting divided by the number of target biological objects present in the initial sample expressed in percentage.

FIG. 1A and FIGS. 1B-1D are a top view and corresponding cross-sectional views of a microfluidic chip 100, respectively. The microfluidic chip 100 includes a planar substrate 102, which has a first planar surface 104 and a second planar surface 106 opposite the first planar surface 104, and a lid 108 attached to the planar substrate 102 at the first planar surface 104. The planar substrate 102 includes a network of channels 111 recessed from the first planar surface 104 and substantially covered by the lid 108. The network of channels 111 includes a separation channel 110 having an upstream end and a downstream end, a side inlet port 112 for introducing a first fluid into the separation channel 110, a pair of side inlet channels 114 connecting the side inlet port 112 to the separation channel 110 at or near the upstream end thereof, a center inlet port 116 for introducing a second fluid into the separation channel 110, a center inlet channel 118 connecting the center inlet port 116 to the separation channel 110 at or near the upstream end thereof, a side outlet port 120 for extracting a third fluid from the separation channel 110, a pair of side outlet channels 122 connecting the side outlet port 120 to the separation channel 110 at or near the downstream end thereof, a center outlet port 124 for extracting a fourth fluid from the separation channel 110, a center outlet channel 126 connecting the center outlet port 124 to the separation channel 110 at or near the downstream end thereof.

The side and center inlet ports 112, 116 in FIG. 1B and the center outlet port 124 in FIG. 1D are opened to the exterior of the microfluidic chip 100 at the second planar surface 106 of the planar substrate 102. However, any of the ports 112, 116, 120, 124 may alternatively be opened to the exterior of the microfluidic chip 100 through the lid 108, which may include through-holes aligned with the respective port positions in the planar substrate 102.

Referring back to FIG. 1A, the separation channel 110 may have a linear shape with a nominal width, W, between two sidewalls thereof. W may be in the range of approximately 100 μm to 1 mm. One or more of the side inlet channels 114, the center inlet channel 118, the side outlet channels 122, and the center outlet channel 126 may be narrower than the nominal width of the separation channel 110. Referring to FIG. 1C, the separation channel 110 may have a nominal depth, D, as measured from the first planar surface 104. D may be in the range of approximately 50 μm to 500 μm. One or more of the side inlet channels 114, the center inlet channel 118, the side outlet channels 122, and the center outlet channel 126 may be shallower than the nominal depth of the separation channel 110.

The pair of side inlet channels 114 connect to the separation channel 110 at the two sidewalls thereof, near or at the upstream end. Therefore, the first fluid, which flows through the pair of side inlet channels 114, is introduced into the separation channel 110 as two streams flowing adjacent to the two sidewalls of the separation channel 110. The center inlet channel 118 connects to the separation channel 110 at or near the center thereof. The second fluid, which flows through the center inlet channels 118, is introduced into the center of the separation channel 110 and is interposed between the two streams of the first fluid at or near the upstream end of the separation channel 110.

The pair of side outlet channels 122 connect to the separation channel 110 at the two sidewalls thereof, at or near the downstream end. Therefore, the fluid flowing adjacent to the two sidewalls at or near the downstream end of the separation channel 110 is diverted by the pair of side outlet channels 122 to become the third fluid and exits the microfluidic chip 100 through the side outlet port 120. The remaining fluid at or near the center of the separation channel 110 not diverted by the pair of side outlet channels 122 becomes the fourth fluid and proceeds to flow through the center outlet channel 126 and exit the microfluidic chip 100 through the center outlet port 124.

FIG. 1E shows the fluidic paths through the microfluidic chip 100 in accordance with the port positions described above. The first and second fluids are introduced into the microfluidic chip 100 through the side and center inlet ports 112 and 116, respectively. The third and fourth fluids are extracted from the microfluidic chip 100 through the side and center outlet ports 120 and 124, respectively. The first fluid introduced through the side inlet port 112 may be a sample fluid that includes particles or biological objects with different sizes or acoustic contrasts for separation by acoustic radiation pressure, while the second fluid introduced through the center inlet port 116 may be a buffer fluid that does not contain any particles or biological objects. After passing through the separation channel 110, the third fluid extracted from the side outlet port 120 may include the particles or biological objects with relatively smaller sizes or smaller acoustic contrasts, while the fourth fluid extracted from the center outlet port 124 may include the particles or biological objects with relatively larger sizes or higher acoustic contrasts.

The microfluidic chip 100 is a part of a microfluidic device 128, which may further include a piezoelectric transducer 130 attached to the microfluidic chip 100 as shown in FIG. 1E. The piezoelectric transducer 130 may be attached to the second planar surface 106 of the planar substrate 102, opposite the separation channel 110. The piezoelectric transducer 130 may alternatively be replaced by a cluster of two or more piezoelectric transducers disposed along the separation channel 110 and operating at the same frequency. The piezoelectric transducer 130 or the cluster of piezoelectric transducers may alternatively be attached to the microfluidic chip 100 at the exterior of the lid 108. Still alternatively, each of the second planar surface 106 of the planar substrate 102 and the exterior of the lid 108 independently has one or more piezoelectric transducers attached thereto.

The piezoelectric transducer 130 or cluster of piezoelectric transducers may receive power in the form of an oscillating voltage with a frequency in the range of 100 kHz to 100 MHz to generate acoustic pressure waves in the separation channel 110 between the two sidewalls thereof when a liquid is present. An acoustic standing wave may form in the separation channel 110 when the channel width, W, is an integer multiple of one-half wavelength of the acoustic pressure waves, which may depend on the excitation frequency of the power applied to the piezoelectric transducer 130 and the compressibility and density of the liquid in the separation channel 110. When W is equal to one-half wavelength of the acoustic waves generated by the piezoelectric transducer 130 or cluster of piezoelectric transducers, a standing wave is formed between the two sidewalls of the separation channel 110 with a single acoustic pressure node positioned along the center of the separation channel 110. Objects having relatively larger sizes and/or higher acoustic contrasts may move towards the pressure node at a faster rate, thereby allowing the separation of objects by size or acoustic contrast.

Operation of the microfluidic device 128 under the condition of single pressure node will now be described with reference to FIGS. 1A-1E. A sample fluid containing a population of first type particles or biological objects 132 and another population of second type particles or biological entities 134 is introduced into the side inlet port 112, while a buffer fluid is introduced into the center inlet port 116. The first and second type particles or biological objects 132 and 134 may have sufficiently different physical sizes and/or acoustic contrasts, such as mass densities and compressibilities, to allow them to be separated by acoustic radiation pressure. For example, the first type particles or biological objects 132 may have a larger physical size and/or a higher acoustic contrast, such as a higher mass density and/or a lower compressibility, thereby allowing the acoustic radiation pressure to push the first type particles or biological objects 132 towards the pressure node located along the center of the separation channel 110 when operating under the single-node condition.

The sample fluid containing the first and second type particles or biological objects 132 and 134 is introduced into the separation channel 110 at or near the upstream end thereof via the pair of side inlet channels 114 as two streams flowing adjacent to the sidewalls. The two streams of the sample fluid in the separation channel 110, which may behave like laminar flow, are interposed by the buffer fluid from the center inlet port 116, which may act as a sheath fluid that retards or prevents the movement of the second type particles or biological objects 134 towards the pressure node positioned along the center of the separation channel 110. As the sample fluid progresses downstream in the separation channel 110, the acoustic radiation pressure pushes the first type particles or biological objects 132 towards the pressure node positioned along the center of the separation channel 110, while the second type particles or biological objects 134 remain mostly close to the sidewalls. At the downstream end of the separation channel 110, the first type particles or biological objects 132 at the center exit the microfluidic device 128 through the center outlet port 124 and the second type particles or biological objects 134 near the sidewalls are diverted to the side outlet port 120 through the pair of side outlet channels 122.

Alternatively, the microfluidic device 128 may operate under the two-node condition, where the width of the separation channel 110, W, corresponds to the wavelength of acoustic waves generated by the piezoelectric transducer 130 or cluster of piezoelectric transducers. Under such condition, the two off-center pressure nodes are located at 4/W away from the two sidewalls of the separation channel 110, respectively. In contrast to the single-node condition, the sample fluid and the buffer fluid may be introduced into the center inlet port 116 and the side inlet port 112, respectively. Accordingly, the second type particles or biological objects 134 may exit the microfluidic device 128 through the center outlet port 124 and the first type particles or biological objects 132 may be diverted to the side outlet port 120 through the pair of side outlet channels 122.

Figure 2B:
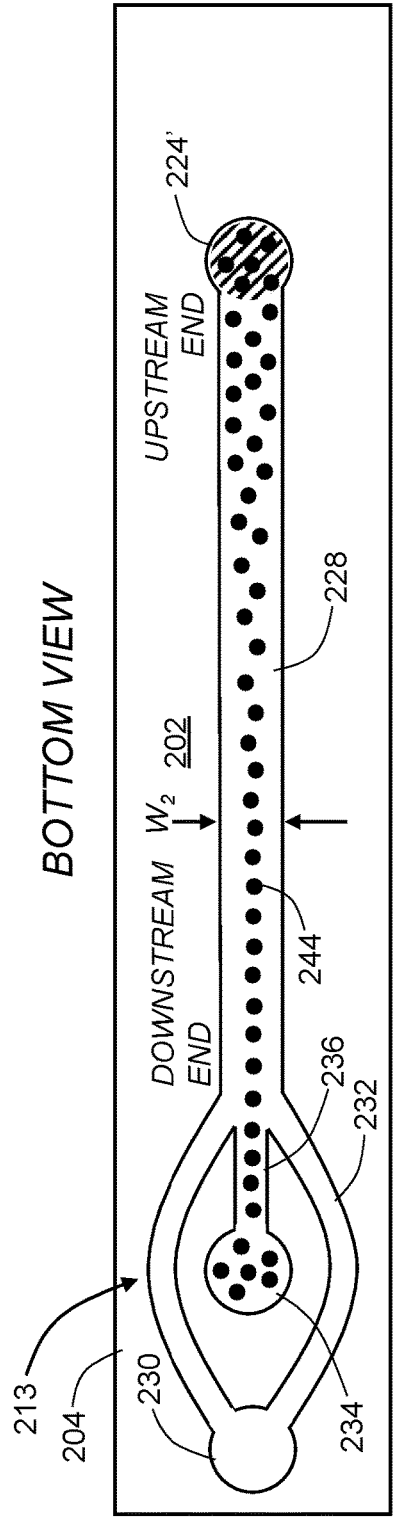

FIGS. 2A and 2B are, respectively, a top view showing a first planar surface 200 and a bottom view showing a second planar surface 202 of a planar substrate 204 for a microfluidic chip in accordance with an embodiment of the present invention. A first lid 206 is attached to the first planar surface 200 and a second lid 208 is attached to the second planar surface 202 to form the microfluidic chip 209, as shown in the cross-sectional views of FIGS. 2C-2F. The first and second lids 206 and 208 are omitted in FIGS. 2A and 2B for reasons of clarity.

Referring to FIG. 2A, the planar substrate 204 includes a first network of channels 211 recessed from the first planar surface 200 and substantially covered by the first lid 206. The first network of channels 211 includes a separation channel 210 having an upstream end and a downstream end, a side inlet port 212 for introducing a first fluid into the separation channel 210, a pair of side inlet channels 214 connecting the side inlet port 212 to the separation channel 210 at or near the upstream end thereof, a center inlet port 216 for introducing a second fluid into the separation channel 210, a center inlet channel 218 connecting the center inlet port 216 to the separation channel 210 at or near the upstream end thereof, a side outlet port 220 for extracting a third fluid from the separation channel 210, a pair of side outlet channels 222 connecting the side outlet port 220 to the separation channel 210 at or near the downstream end thereof, a center connection port 224' for extracting a fourth fluid from the separation channel 210, and an optional center outlet channel 226 connecting the center connection port 224' to the separation channel 210 at or near the downstream end thereof. The center connection port 224' may alternatively be directly connected to the separation channel 210 at the downstream end thereof. The separation channel 210 may have a linear shape with a nominal width, $W_1$, between two sidewalls thereof. $W_1$ may be in the range of approximately 100 µm to 1 mm. One or more of the side inlet channels 214, the center inlet channel 218, the side outlet channels 222, and the center outlet channel 226 may be narrower than the nominal width of the separation channel 210.

The side and center inlet ports 212, 216 and the side outlet port 220 of the first network of channels 211 on the first planar surface 200 are not bored through the planar substrate 204 as shown in FIGS. 2C and 2F. These ports 212, 216, and 220 are opened to the exterior of the microfluidic chip 209 through the first lid 206, which includes through-holes aligned with the respective ports 212, 216, and 220 of the first network of channels 211. FIG. 2E shows that the center connection port 224' is bored through the planar substrate 204 but is not opened to the exterior of the microfluidic chip 209. The center connection port 224', which is in the form of a through-hole in the planar substrate 204 that is opened to the first and second planar surfaces 200 and 202, allows the fluid to flow from the first network of channels 211 to a second network of channels 213 formed on the second planar surface 202, thereby providing a fluidic connection between the first and second networks of channels 211 and 213 as highlighted by the crosshatch pattern in FIGS. 2A and 2B.

Referring to FIG. 2B, the planar substrate 204 includes the second network of channels 213 recessed from the second planar surface 202 and substantially covered by the second lid 208. The second network of channels 213 includes a concentration channel 228 having an upstream end and a downstream end, the center connection port 224' connected to the upstream end of the concentration channel 228 for introducing the fourth fluid into the concentration channel 228, a side outlet port 230 for extracting a fifth fluid from the concentration channel 228, a pair of side outlet channels 232 connecting the side outlet port 230 to the concentration channel 228 at or near the downstream end thereof, a center outlet port 234 for extracting a sixth fluid from the concentration channel 228, and an optional center outlet channel 236 connecting the center outlet port 234 to the concentration channel 228 at or near the downstream end thereof. The center outlet port 234 may alternatively be directly connected to the concentration channel 228 at the downstream end thereof. The concentration channel 228 may have a linear shape with a nominal width, $W_2$, between two sidewalls thereof. $W_2$ may be in the range of approximately 100 µm to 1 mm. One or more of the side outlet channels 232 and the center outlet channel 236 may be narrower than the nominal width of the concentration channel 228.

The side and center outlet ports 230 and 234 of the second network of channels 213 on the second planar surface 202 are not bored through the planar substrate 204 as shown in FIG. 2C. These ports 230 and 234 are opened to the exterior of the microfluidic chip 209 through the second lid 208, which includes through-holes aligned with the respective ports 230 and 234 of the second network of channels 213.

Referring to FIG. 2D, the separation channel 210 may have a nominal depth, $D_1$, as measured from the first planar surface 200. $D_1$ may be in the range of approximately 50 µm to 500 µm. One or more of the side inlet channels 214, the center inlet channel 218, the side outlet channels 222, and the center outlet channel 226 may be shallower than the nominal depth of the separation channel 210. The concentration channel 228 may have a nominal depth, $D_2$, as measured from the second planar surface 202. $D_2$ may be in the range of approximately 50 µm to 500 µm. One or more of the side outlet channels 232 and the center outlet channel 236 may be shallower than the nominal depth of the concentration channel 228.

While the cross-sectional views of FIGS. 2C, 2D, and 2F may appear to show the ports and channels recessed from the first planar surface 200 and the ports and channels recessed from the second planar surface 202 aligning to each other, features of the first and second networks of channels 211 and 213, except for the center connection port 224', do not have to be vertically aligned to practice the present invention.

Referring back to FIG. 2A, the pair of side inlet channels 214 on the first planar surface 200 are connected to the separation channel 210 at the two sidewalls thereof, near or at the upstream end. Therefore, the first fluid, which flows through the pair of side inlet channels 214, is introduced into the separation channel 210 as two streams flowing adjacent to the two sidewalls of the separation channel 210. The center inlet channel 218 is connected to the separation channel 210 at or near the center thereof. The second fluid, which flows through the center inlet channels 218, is introduced into the center of the separation channel 210 and is interposed between the two streams of the first fluid at or near the upstream end of the separation channel 210. The pair of side outlet channels 222 are connected to the separation channel 210 at the two sidewalls thereof, at or near the downstream end. Therefore, the fluid flowing adjacent to the two sidewalls at or near the downstream end of the separation channel 210 is diverted by the pair of side outlet channels 222 to become the third fluid and exits the microfluidic chip 209 through the side outlet port 220. The remaining fluid at or near the center of the separation channel 210 not diverted by the pair of side outlet channels 222 becomes the fourth fluid and proceeds to flow through the center outlet channel 226 and into the center connection port 224', which provides a fluidic connection to the upstream end of the concentration channel 228 on the second planar surface 202.

After exiting the center connection port 224' on the second planar surface 202 as shown in FIG. 2B, the fourth fluid flows through the concentration channel 228 from the upstream end to the downstream end. The pair of side outlet channels 232 are connected to the concentration channel 228 at the two sidewalls thereof, at or near the downstream end. Therefore, the portions of the fourth fluid flowing adjacent to the two sidewalls at or near the downstream end of the concentration channel 228 are diverted by the pair of side outlet channels 232 to become the fifth fluid and exit the microfluidic chip 209 through the side outlet port 230. The remaining fourth fluid near the center of the concentration channel 228 not diverted by the pair of side outlet channels 232 becomes the sixth fluid and proceeds to exit the microfluidic chip 209 through the center outlet port 234.

FIG. 2G shows the fluidic paths through the microfluidic chip 209 in accordance with the port positions described above. The first and second fluids are introduced into the microfluidic chip 209 through the side and center inlet ports 212 and 216 on the first planar surface 200, respectively. The third fluid is extracted from the microfluidic chip 209 through the side outlet port 220 and the fourth fluid flows into the second network of channels 213 on the second planar surface 202 through the center connection port 224'. The fifth and sixth fluids are extracted from the microfluidic chip 209 through the side and center outlet ports 230 and 234 on the second planar surface 202, respectively.

The first fluid introduced through the side inlet port 212, which is opened to the exterior of the first lid 206, may be a sample fluid that includes particles or biological objects with different sizes or acoustic contrasts for separation by acoustic radiation pressure, while the second fluid introduced through the center inlet port 216, which is opened to the exterior of the first lid 206, may be a buffer fluid that does not contain any particles or biological objects. After passing through the separation channel 210, the third fluid extracted from the side outlet port 220, which is opened to the exterior of the first lid 206, may include the particles or biological objects with relatively smaller sizes or lower acoustic contrasts, while the fourth fluid entering the center connection port 224', which is opened to the second planar surface 202, may include the particles or biological objects with relatively larger sizes or higher acoustic contrasts. After passing through the concentration channel 228, the sixth fluid extracted from the center outlet port 234, which is opened to the exterior of the second lid 208, may include most of the particles or biological objects with the relatively larger sizes or higher acoustic contrasts from the fourth fluid, with the excess liquid being removed as the fifth fluid through the side outlet port 230, which is opened to the exterior of the second lid 208. Accordingly, the first and second networks of channels 211 and 213 are fluidically coupled in series.

With continuing reference to FIG. 2G, the microfluidic chip 209 is a part of a microfluidic device 238, which may further include one or more first piezoelectric transducers 240 attached to the exterior of the first lid 206 opposite the first planar surface 200 and/or one or more second piezoelectric transducers 242 attached to the exterior of the second lid 208 opposite the second planar surface 202. The first and second piezoelectric transducers 240 and 242 may be used to generate acoustic pressure waves in the separation channel 210 and the concentration channel 228, respectively. The present invention may be practiced using a single first piezoelectric transducer 240 operating at a first frequency and disposed directly over a portion or the entire length of the separation channel 210. Alternatively, a cluster of two or more first piezoelectric transducers 240 operating at the first frequency may be disposed directly over and along the separation channel 210. Likewise, a single second piezoelectric transducer 242 operating at a second frequency may be disposed directly beneath a portion or the entire length of the concentration channel 228. Alternatively, a cluster of two or more second piezoelectric transducers 242 operating at the second frequency may be disposed directly beneath and along the concentration channel 228.

The first piezoelectric transducers 240 may receive power in the form of an oscillating voltage with a frequency in the range of 100 kHz to 100 MHz to generate acoustic pressure waves in the separation channel 210 between the two sidewalls thereof when a liquid is present. An acoustic standing wave may form in the separation channel 210 when the channel width, $W_1$, is an integer multiple of one-half wavelength of the acoustic pressure waves, which may depend on the excitation frequency of the power applied to the first piezoelectric transducers 240 and the compressibility and density of the liquid in the separation channel 210. When $W_1$ is equal to one-half wavelength of the acoustic waves generated by the first piezoelectric transducers 240, a standing wave is formed between the two sidewalls of the separation channel 210 with a single acoustic pressure node positioned along the center of the separation channel 210. Objects having relatively larger sizes and/or higher acoustic contrasts may move towards the pressure node at a faster rate, thereby allowing the separation of objects by size or acoustic contrast.

The second piezoelectric transducers 242 may receive power in the form of an oscillating voltage with a frequency in the range of 100 kHz to 100 MHz to generate acoustic pressure waves in the concentration channel 228 between the two sidewalls thereof when a liquid is present. An acoustic standing wave may form in the concentration channel 228 when the channel width, $W_2$, is an integer multiple of one-half wavelength of the acoustic pressure waves, which may depend on the excitation frequency of the power applied to the second piezoelectric transducers 242 and the compressibility and density of the liquid in the concentration channel 228. When $W_2$ is equal to one-half wavelength of the acoustic waves generated by the second piezoelectric transducers 242, a standing wave is formed between the two sidewalls of the concentration channel 228 with a single acoustic pressure node positioned along the center of the concentration channel 228. Objects having relatively larger sizes and/or higher acoustic contrasts may move towards the pressure node, thereby allowing the excess liquid to be diverted through the side outlet port 230 as the fifth fluid.

In an embodiment, an acoustic standing wave with single pressure node is formed in each of the separation channel 210 and the concentration channel 228. Accordingly, $W_1$ is equal to one-half of the wavelength of the standing wave in the separation channel 210, and $W_2$ is equal to one-half of the wavelength of the standing wave in the concentration channel 228. The separation channel 210 and the concentration channel 228 may have the same width (i.e., $W_1=W_2$), which would require the first and second piezoelectric transducers 240 and 242 to operate at substantially the same frequency. Moreover, if sufficient vibration power can be generated by the first or second piezoelectric transducers 240, 242, then only the first piezoelectric transducers 240 or the second piezoelectric transducers 242 may be needed to generate both acoustic standing waves in the separation and concentration channels 210 and 228, respectively.

Operation of the microfluidic device 238 under the condition of single pressure node will now be described with reference to FIGS. 2A-2G. A sample fluid containing a population of first type particles or biological objects 244 and another population of second type particles or biological entities 246 is introduced into the side inlet port 212 through the first lid 206 as the first fluid, while a buffer fluid is introduced into the center inlet port 216 through the first lid 206 as the second fluid. The first and second type particles or biological objects 244 and 246 may have sufficiently different physical sizes and/or acoustic contrasts, such as mass densities and compressibilities, to allow them to be separated by acoustic radiation pressure. For example, the first type particles or biological objects 244 may have a larger physical size, and/or a higher acoustic contrast, such as a higher mass density and/or a lower compressibility, thereby allowing the acoustic radiation pressure to push the first type particles or biological objects 244 towards the pressure node located along the center of the separation channel 210 when operating under the single-node condition.

The sample fluid containing the first and second type particles or biological objects 244 and 246 is introduced into the separation channel 210 at or near the upstream end thereof via the pair of side inlet channels 214 as two streams flowing adjacent to the sidewalls of the separation channel 210. The two streams of the sample fluid in the separation channel 210, which may behave like laminar flow, are interposed by the buffer fluid from the center inlet port 216, which may act as a sheath fluid that retards or prevents the movement of the second type particles or biological objects 246 towards the pressure node positioned along the center of the separation channel 210. As the sample fluid progresses downstream in the separation channel 210, the acoustic radiation pressure pushes the first type particles or biological objects 244 towards the pressure node positioned along the center of the separation channel 210, while the second type particles or biological objects 246 remain mostly close to the sidewalls. At the downstream end of the separation channel 210, the second type particles or biological objects 246 at or near the sidewalls are diverted through the pair of side outlet channels 222 and into the side outlet port 220 as a part of the third fluid, and the first type particles or biological objects 244 at or near the channel center flow through the center outlet channel 226 and into the center connection port 224' as a part of the fourth fluid.

After exiting the first network of channels 211 on the first planar surface 200 through the center connection port 224', the fourth fluid containing the first type particles or biological objects 244 enters the upstream end of the concentration channel 228 on the second planar surface 202. As the fourth fluid progresses downstream in the concentration channel 228, the acoustic radiation pressure pushes the first type particles or biological objects 244 towards the pressure node positioned along the center of the concentration channel 228. At the downstream end of the concentration channel 228, excess liquid at or near the sidewalls is diverted through the pair of side outlet channels 232 and into the side outlet port 230 as the fifth fluid, and the first type particles or biological objects 244 at or near the channel center flow through the center outlet channel 236 and into the center outlet port 234 as a part of the sixth fluid, which is a concentrate of the fourth fluid and has a lower liquid content than the fourth fluid prior to the concentration process.

FIGS. 3A and 3B are, respectively, a top view showing a first planar surface 300 and a bottom view showing a second planar surface 302 of a planar substrate 304 for a microfluidic chip in accordance with another embodiment of the present invention. A first lid 306 is attached to the first planar surface 300 and a second lid 308 is attached to the second planar surface 302 to form the microfluidic chip 309, as shown in the cross-sectional views of FIGS. 3C-3F. The first and second lids 306 and 308 are omitted in FIGS. 3A and 3B for reasons of clarity.

Referring to FIG. 3A, the planar substrate 304 includes a first network of channels 311 recessed from the first planar surface 300 and substantially covered by the first lid 306. The first network of channels 311 includes a separation channel 310 having an upstream end and a downstream end, a side inlet port 312 for introducing a first fluid into the separation channel 310, a pair of side inlet channels 314 connecting the side inlet port 312 to the separation channel 310 at or near the upstream end thereof, a center inlet port 316 for introducing a second fluid into the separation channel 310, a center inlet channel 318 connecting the center inlet port 316 to the separation channel 310 at or near the upstream end thereof, a side connection port 320' for extracting a third fluid from the separation channel 310, a pair of side outlet channels 322 connecting the side connection port 320' to the separation channel 310 at or near the downstream end thereof, a center outlet port 324 for extracting a fourth fluid from the separation channel 310, and an optional center outlet channel 326 connecting the center outlet port 324 to the separation channel 310 at or near the downstream end thereof. The center outlet port 324 may alternatively be directly connected to the separation channel 310 at the downstream end thereof. The separation channel 310 may have a linear shape with a nominal width, $W_1$, between two sidewalls thereof. $W_1$ may be in the range of approximately 100 μm to 1 mm. One or more of the side inlet channels 314, the center inlet channel 318, the side outlet channels 322, and the center outlet channel 326 may be narrower than the nominal width of the separation channel 310.

The side and center inlet ports 312, 316 and the center outlet port 324 of the first network of channels 311 on the first planar surface 300 are not bored through the planar substrate 304 as shown in FIGS. 3C and 3E. These ports 312, 316, and 324 are opened to the exterior of the microfluidic chip 309 through the first lid 306, which includes through-holes aligned with the respective ports 312, 316, and 324 of the first network of channels 311. FIG. 3F shows that the side connection port 320' is bored through the planar substrate 304 but is not opened to the exterior of the microfluidic chip 309. The side connection port 320', which is in the form of a through-hole in the planar substrate 304 that is opened to the first and second planar surfaces 300 and 302, allows the fluid to flow from the first network of channels 311 to a second network of channels 313 formed on the second planar surface 302, thereby providing a fluidic connection between the first and second networks of channels 311 and 313 as highlighted by the crosshatch pattern in FIGS. 3A and 3B.

Referring to FIG. 3B, the planar substrate 304 includes the second network of channels 313 recessed from the second planar surface 302 and substantially covered by the second lid 308. The second network of channels 313 includes a concentration channel 328 having an upstream end and a downstream end, the side connection port 320' connected to the upstream end of the concentration channel 328 for introducing the third fluid into the concentration channel 328, a side outlet port 330 for extracting a fifth fluid from the concentration channel 328, a pair of side outlet channels 332 connecting the side outlet port 330 to the concentration channel 328 at or near the downstream end thereof, a center outlet port 334 for extracting a sixth fluid from the concentration channel 328, and an optional center outlet channel 336 connecting the center outlet port 334 to the concentration channel 328 at or near the downstream end thereof. The center outlet port 334 may alternatively be directly connected to the concentration channel 328 at the downstream end thereof. The concentration channel 328 may have a linear shape with a nominal width, $W_2$, between two sidewalls thereof. $W_2$ may be in the range of approximately 100 µm to 1 mm. One or more of the side outlet channels 332 and the center outlet channel 336 may be narrower than the nominal width of the concentration channel 328.

The side and center outlet ports 330 and 334 of the second network of channels 313 on the second planar surface 302 are not bored through the planar substrate 304 as shown in FIG. 2C. These ports 330 and 334 are opened to the exterior of the microfluidic chip 309 through the second lid 308, which includes through-holes aligned with the respective ports 330 and 334 of the second network of channels 313.

Referring to FIG. 3D, the separation channel 310 may have a nominal depth, $D_1$, as measured from the first planar surface 300. $D_1$ may be in the range of approximately 50 µm to 500 µm. One or more of the side inlet channels 314, the center inlet channel 318, the side outlet channels 322, and the center outlet channel 326 may be shallower than the nominal depth of the separation channel 310. The concentration channel 328 may have a nominal depth, $D_2$, as measured from the second planar surface 302. $D_2$ may be in the range of approximately 50 µm to 500 µm. One or more of the side outlet channels 332 and the center outlet channel 336 may be shallower than the nominal depth of the concentration channel 328.

While the cross-sectional views of FIGS. 3C and 3D may appear to show the ports and channels recessed from the first planar surface 300 and the ports and channels recessed from the second planar surface 302 aligning to each other, features of the first and second networks of channels 311 and 313, except for the side connection port 320', do not have to be vertically aligned to practice the present invention.

Referring back to FIG. 3A, the pair of side inlet channels 314 on the first planar surface 300 are connected to the separation channel 310 at the two sidewalls thereof, near or at the upstream end. Therefore, the first fluid, which flows through the pair of side inlet channels 314, is introduced into the separation channel 310 as two streams flowing adjacent to the two sidewalls of the separation channel 310. The center inlet channel 318 is connected to the separation channel 310 at or near the center thereof. The second fluid, which flows through the center inlet channels 318, is introduced into the center of the separation channel 310 and is interposed between the two streams of the first fluid at or near the upstream end of the separation channel 310. The pair of side outlet channels 322 are connected to the separation channel 310 at the two sidewalls thereof, at or near the downstream end. Therefore, the fluid flowing adjacent to the two sidewalls at or near the downstream end of the separation channel 310 is diverted by the pair of side outlet channels 322 to become the third fluid and flows into the side connection port 320', which provides a fluidic connection to the upstream end of the concentration channel 328 on the second planar surface 302. The remaining fluid at or near the center of the separation channel 310 not diverted by the pair of side outlet channels 322 becomes the fourth fluid and proceeds to flow through the center outlet channel 326 and exit the microfluidic chip 309 through the center outlet port 324.

After exiting the side connection port 320' on the second planar surface 302 as shown in FIG. 3B, the third fluid flows through the concentration channel 328 from the upstream end to the downstream end. The pair of side outlet channels 332 are connected to the concentration channel 328 at the two sidewalls thereof, at or near the downstream end. Therefore, the portions of the third fluid flowing adjacent to the two sidewalls at or near the downstream end of the concentration channel 328 are diverted by the pair of side outlet channels 332 to become the fifth fluid and exit the microfluidic chip 309 through the side outlet port 330. The remaining third fluid near the center of the concentration channel 328 not diverted by the pair of side outlet channels 332 becomes the sixth fluid and proceeds to exit the microfluidic chip 309 through the center outlet port 334.

FIG. 3G shows the fluidic paths through the microfluidic chip 309 in accordance with the port positions described above. The first and second fluids are introduced into the microfluidic chip 309 through the side and center inlet ports 312 and 316 on the first planar surface 300, respectively. The fourth fluid is extracted from the microfluidic chip 309 through the center outlet port 324 and the third fluid flows into the second network of channels 313 on the second planar surface 302 through the side connection port 320'. The fifth and sixth fluids are extracted from the microfluidic chip 309 through the side and center outlet ports 330 and 334 on the second planar surface 302, respectively.

The first fluid introduced through the side inlet port 312, which is opened to the exterior of the first lid 306, may be a sample fluid that includes particles or biological objects with different sizes or acoustic contrasts for separation by acoustic radiation pressure, while the second fluid introduced through the center inlet port 316, which is opened to the exterior of the first lid 306, may be a buffer fluid that does not contain any particles or biological objects. After passing through the separation channel 310, the fourth fluid extracted from the center outlet port 324, which is opened to the exterior of the first lid 306, may include the particles or biological objects with relatively larger sizes or higher acoustic contrasts, while the third fluid entering the side connection port 320', which is opened to the second planar surface 302, may include the particles or biological objects with relatively smaller sizes or lower acoustic contrasts. After passing through the concentration channel 328, the sixth fluid extracted from the center outlet port 334, which is opened to the exterior of the second lid 308, may include most of the particles or biological objects with the relatively smaller size or lower acoustic contrast from the third fluid, with the excess liquid being removed as the fifth fluid through the side outlet port 330, which is opened to the exterior of the second lid 308. Accordingly, the first and second networks of channels 311 and 313 are fluidically coupled in series.

With continuing reference to FIG. 3G, the microfluidic chip 309 is a part of a microfluidic device 338, which may further include one or more first piezoelectric transducers 340 attached to the exterior of the first lid 306 opposite the first planar surface 300 and/or one or more second piezoelectric transducers 342 attached to the exterior of the second lid 308 opposite the second planar surface 302. The first and second piezoelectric transducers 340 and 342 may be used to generate acoustic pressure waves in the separation channel 310 and the concentration channel 328, respectively. The present invention may be practiced using a single first piezoelectric transducer 340 operating at a first frequency and disposed directly over a portion or the entire length of the separation channel 310. Alternatively, a cluster of two or more first piezoelectric transducers 340 operating at the first frequency may be disposed directly over and along the separation channel 310. Likewise, a single second piezoelectric transducer 342 operating at a second frequency may be disposed directly beneath a portion or the entire length of the concentration channel 328. Alternatively, a cluster of two or more second piezoelectric transducers 342 operating at the second frequency may be disposed directly beneath and along the concentration channel 328.

The first piezoelectric transducers 340 may receive power in the form of an oscillating voltage with a frequency in the range of 100 kHz to 100 MHz to generate acoustic pressure waves in the separation channel 310 between the two sidewalls thereof when a liquid is present. An acoustic standing wave may form in the separation channel 310 when the channel width, $W_1$, is an integer multiple of one-half wavelength of the acoustic pressure waves, which may depend on the excitation frequency of the power applied to the first piezoelectric transducers 340 and the compressibility and density of the liquid in the separation channel 310. When W is equal to one-half wavelength of the acoustic waves generated by the first piezoelectric transducers 340, a standing wave is formed between the two sidewalls of the separation channel 310 with a single acoustic pressure node positioned along the center of the separation channel 310. Objects having relatively larger sizes and/or higher acoustic contrasts may move towards the pressure node at a faster rate, thereby allowing the separation of objects by size or acoustic contrast.

The second piezoelectric transducers 342 may receive power in the form of an oscillating voltage with a frequency in the range of 100 kHz to 100 MHz to generate acoustic pressure waves in the concentration channel 328 between the two sidewalls thereof when a liquid is present. An acoustic standing wave may form in the concentration channel 328 when the channel width, $W_2$, is an integer multiple of one-half wavelength of the acoustic pressure waves, which may depend on the excitation frequency of the power applied to the second piezoelectric transducers 342 and the compressibility and density of the liquid in the concentration channel 328. When $W_2$ is equal to one-half wavelength of the acoustic waves generated by the second piezoelectric transducers 342, a standing wave is formed between the two sidewalls of the concentration channel 328 with a single acoustic pressure node positioned along the center of the concentration channel 328. Objects having relatively larger sizes and/or higher acoustic contrasts may move towards the pressure node, thereby allowing the excess liquid to be diverted through the side outlet port 330 as the fifth fluid.

In an embodiment, an acoustic standing wave with single pressure node is formed in each of the separation channel 310 and the concentration channel 328. Accordingly, $W_1$ is equal to one-half of the wavelength of the standing wave in the separation channel 310, and $W_2$ is equal to one-half of the wavelength of the standing wave in the concentration channel 328. The separation channel 310 and the concentration channel 328 may have the same width (i.e., $W_1=W_2$), which would require the first and second piezoelectric transducers 340 and 342 to operate at substantially the same frequency. Moreover, if sufficient vibration power can be generated by the first or second piezoelectric transducers 340, 342, then only the first piezoelectric transducers 340 or the second piezoelectric transducers 342 may be needed to generate both acoustic standing waves in the separation and concentration channels 310 and 328, respectively.

Operation of the microfluidic device 338 under the condition of single pressure node will now be described with reference to FIGS. 3A-3G. A sample fluid containing a population of first type particles or biological objects 344 and another population of second type particles or biological entities 346 is introduced into the side inlet port 312 through the first lid 306 as the first fluid, while a buffer fluid is introduced into the center inlet port 316 through the first lid 306 as the second fluid. The first and second type particles or biological objects 344 and 346 may have sufficiently different physical sizes and/or acoustic contrasts, such as mass densities and compressibilities, to allow them to be separated by acoustic radiation pressure. For example, the first type particles or biological objects 344 may have a larger physical size, and/or a higher acoustic contrast, such as a higher mass density and/or a lower compressibility, thereby allowing the acoustic radiation pressure to push the first type particles or biological objects 344 towards the pressure node located along the center of the separation channel 310 when operating under the single-node condition.

The sample fluid containing the first and second type particles or biological objects 344 and 346 is introduced into the separation channel 310 at or near the upstream end thereof via the pair of side inlet channels 314 as two streams flowing adjacent to the sidewalls of the separation channel 310. The two streams of the sample fluid in the separation channel 310, which may behave like laminar flow, are interposed by the buffer fluid from the center inlet port 316, which may act as a sheath fluid that retards or prevents the movement of the second type particles or biological objects 346 towards the pressure node positioned along the center of the separation channel 310. As the sample fluid progresses downstream in the separation channel 310, the acoustic radiation pressure pushes the first type particles or biological objects 344 towards the pressure node positioned along the center of the separation channel 310, while the second type particles or biological objects 346 remain mostly close to the sidewalls. At the downstream end of the separation channel 310, the second type particles or biological objects 346 at or near the sidewalls are diverted through the pair of side outlet channels 322 and into the side connection port 320' as a part of the third fluid, and the first type particles or biological objects 344 at or near the channel center flow through the center outlet channel 326 and into the center outlet port 324 as a part of the fourth fluid.

After exiting the first network of channels 311 on the first planar surface 300 through the side connection port 320', the third fluid containing the second type particles or biological objects 346 enters the upstream end of the concentration channel 328 on the second planar surface 302. As the third fluid progresses downstream in the concentration channel 328, the acoustic radiation pressure gradually pushes the second type particles or biological objects 346 towards the pressure node positioned along the center of the concentration channel 328. At the downstream end of the concentration channel 328, excess liquid at or near the sidewalls is diverted through the pair of side outlet channels 332 and into the side outlet port 330 as the fifth fluid, and the second type particles or biological objects 346 at or near the channel center flow through the center outlet channel 336 and into the center outlet port 334 as a part of the sixth fluid, which is a concentrate of the third fluid and has a lower liquid content than the third fluid prior to the concentration process.

Figure 4A:
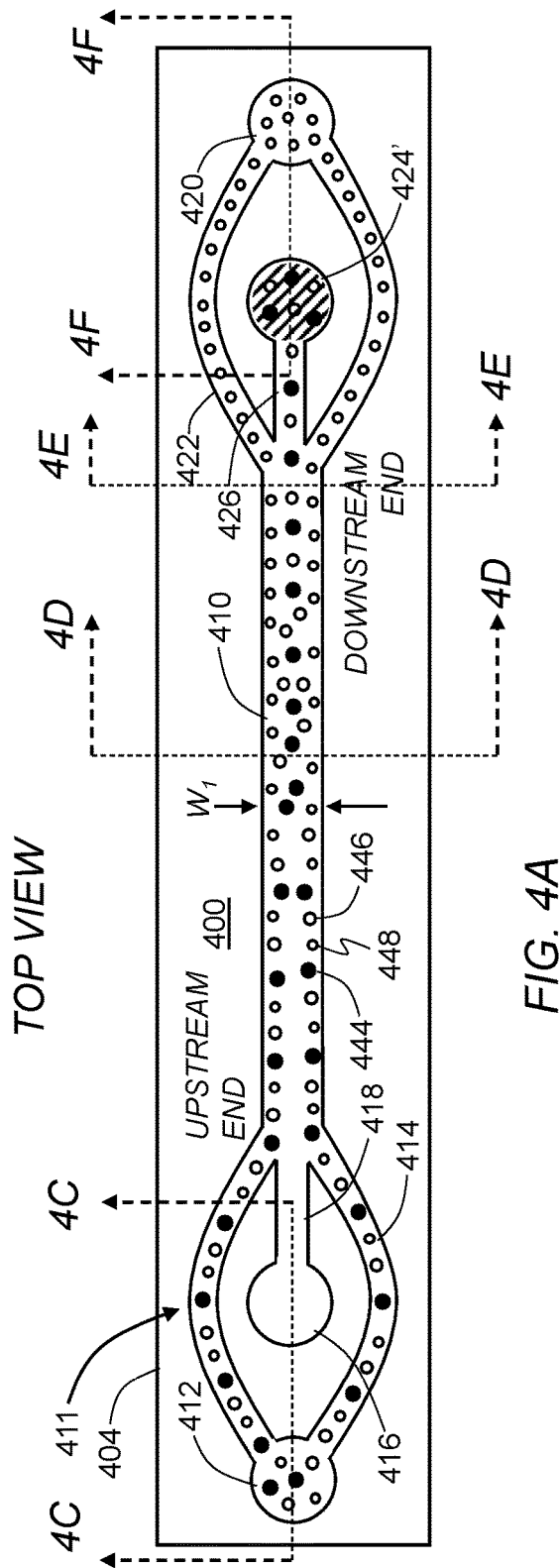
FIGS. 4A and 4B are, respectively, top and bottom views of a planar substrate for a microfluidic chip that contains therein first and second networks of channels in accordance with still another embodiment of the present invention.
Figure 4B:
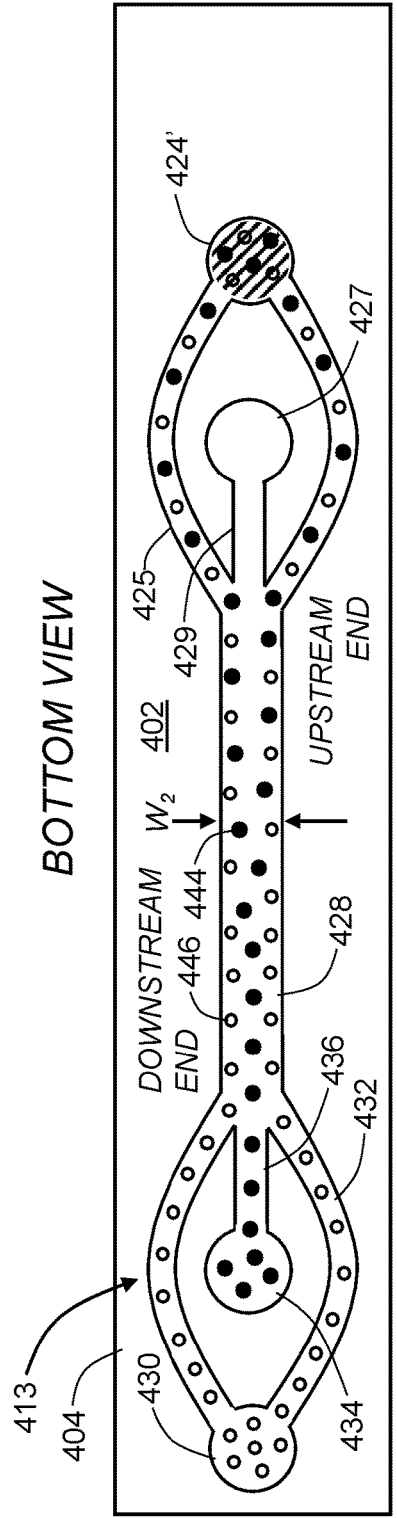

FIGS. 4A and 4B are, respectively, a top view showing a first planar surface 400 and a bottom view showing a second planar surface 402 of a planar substrate 404 for a microfluidic chip in accordance with another embodiment of the present invention. A first lid 406 is attached to the first planar surface 400 and a second lid 408 is attached to the second planar surface 402 to form the microfluidic chip 409, as shown in the cross-sectional views of FIGS. 4C-4F. The first and second lids 406 and 408 are omitted in FIGS. 4A and 4B for reasons of clarity.

Referring to FIG. 4A, the planar substrate 404 includes a first network of channels 411 recessed from the first planar surface 400 and substantially covered by the first lid 406. The first network of channels 411 includes a first separation channel 410 having an upstream end and a downstream end, a side inlet port 412 for introducing a first fluid into the first separation channel 410, a pair of side inlet channels 414 connecting the side inlet port 412 to the first separation channel 410 at or near the upstream end thereof, a center inlet port 416 for introducing a second fluid into the first separation channel 410, a center inlet channel 418 connecting the center inlet port 416 to the first separation channel 410 at or near the upstream end thereof, a side outlet port 420 for extracting a third fluid from the first separation channel 410, a pair of side outlet channels 422 connecting the side outlet port 420 to the first separation channel 410 at or near the downstream end thereof, a center connection port 424' for extracting a fourth fluid from the first separation channel 410, and an optional center outlet channel 426 connecting the center connection port 424' to the first separation channel 410 at or near the downstream end thereof. The center connection port 424' may alternatively be directly connected to the first separation channel 410 at the downstream end thereof. The first separation channel 410 may have a linear shape with a nominal width, $W_1$, between two sidewalls thereof. $W_1$ may be in the range of approximately 100 μm to 1 mm. One or more of the side inlet channels 414, the center inlet channel 418, the side outlet channels 422, and the center outlet channel 426 may be narrower than the nominal width of the first separation channel 410.

The side and center inlet ports 412, 416 and the side outlet port 420 of the first network of channels 411 on the first planar surface 400 are not bored through the planar substrate 404 as shown in FIGS. 4C and 4F. These ports 412, 416, and 420 are opened to the exterior of the microfluidic chip 409 through the first lid 406, which includes through-holes aligned with the respective ports 412, 416, and 420 of the first network of channels 411. FIG. 4F shows that the center connection port 424' is bored through the planar substrate 404 but is not opened to the exterior of the microfluidic chip 409. The center connection port 424', which is in the form of a through-hole in the planar substrate 404 that is opened to the first and second planar surfaces 400 and 402, allows the fluid to flow from the first network of channels 411 to a second network of channels 413 formed on the second planar surface 402, thereby providing a fluidic connection between the first and second networks of channels 411 and 413 as highlighted by the crosshatch pattern in FIGS. 4A and 4B.

Referring to FIG. 4B, the planar substrate 404 includes the second network of channels 413 recessed from the second planar surface 402 and substantially covered by the second lid 408.

The second network of channels 413 includes a second separation channel 428 having an upstream end and a downstream end, the center connection port 424' for introducing the fourth fluid into the second separation channel 428, a pair of side inlet channels 425 connecting the center connection port 424' to the second separation channel 428 at or near the upstream end thereof, a center inlet port 427 for introducing a fifth fluid into the second separation channel 428, a center inlet channel 429 connecting the center inlet port 427 to the second separation channel 428 at or near the upstream end thereof, a side outlet port 430 for extracting a sixth fluid from the second separation channel 428, a pair of side outlet channels 432 connecting the side outlet port 430 to the second separation channel 428 at or near the downstream end thereof, a center outlet port 434 for extracting a seventh fluid from the second separation channel 428, and an optional center outlet channel 436 connecting the center outlet port 434 to the second separation channel 428 at or near the downstream end thereof. The center outlet port 434 may alternatively be directly connected to the second separation channel 428 at the downstream end thereof. The second separation channel 428 may have a linear shape with a nominal width, $W_2$, between two sidewalls thereof. $W_2$ may be in the range of approximately 100 μm to 1 mm. One or more of the side inlet channels 425, the side outlet channels 432, the center inlet channel 429, and the center outlet channel 436 may be narrower than the nominal width of the second separation channel 428.

The center inlet port 427 and the side and center outlet ports 430 and 434 of the second network of channels 413 on the second planar surface 402 are not bored through the planar substrate 404 as shown in FIGS. 4C and 4E. These ports 427, 430, and 434 are opened to the exterior of the microfluidic chip 409 through the second lid 408, which includes through-holes aligned with the respective ports 427, 430, and 434 of the second network of channels 413.

Referring to FIG. 4D, the first separation channel 410 may have a nominal depth, $D_1$, as measured from the first planar surface 400. $D_1$ may be in the range of approximately 50 μm to 500 μm. One or more of the side inlet channels 414, the center inlet channel 418, the side outlet channels 422, and the center outlet channel 426 may be shallower than the nominal depth of the first separation channel 410. The second separation channel 428 may have a nominal depth, $D_2$, as measured from the second planar surface 402. $D_2$ may be in the range of approximately 50 μm to 500 μm. One or more of the side inlet channels 425, the center inlet channel 429, the side outlet channels 432, and the center outlet channel 436 may be shallower than the nominal depth of the second separation channel 428.

While the cross-sectional views of FIGS. 4C and 4D may appear to show the ports and channels recessed from the first planar surface 400 and the ports and channels recessed from the second planar surface 402 aligning to each other, features of the first and second networks of channels 411 and 413, except for the center connection port 424', do not have to be vertically aligned to practice the present invention.

Referring back to FIG. 4A, the pair of side inlet channels 414 on the first planar surface 400 are connected to the first separation channel 410 at the two sidewalls thereof, near or at the upstream end. Therefore, the first fluid, which flows through the pair of side inlet channels 414, is introduced into the first separation channel 410 as two streams flowing adjacent to the two sidewalls of the first separation channel 410. The center inlet channel 418 is connected to the first separation channel 410 at or near the center thereof. The second fluid, which flows through the center inlet channels 418, is introduced into the center of the first separation channel 410 and is interposed between the two streams of the first fluid at or near the upstream end of the first separation channel 410. The pair of side outlet channels 422 are connected to the first separation channel 410 at the two sidewalls thereof, at or near the downstream end. Therefore, the fluid flowing adjacent to the two sidewalls at or near the downstream end of the first separation channel 410 is diverted by the pair of side outlet channels 422 to become the third fluid and exits the microfluidic chip 409 through the side outlet port 420. The remaining fluid at or near the center of the first separation channel 410 not diverted by the pair of side outlet channels 422 becomes the fourth fluid and proceeds to flow through the center outlet channel 426 and into the center connection port 424', which provides a fluidic connection to the upstream end of the second separation channel 428 on the second planar surface 402.

Referring to FIG. 4B, the pair of side inlet channels 425 on the second planar surface 402 are connected to the second separation channel 428 at the two sidewalls thereof, near or at the upstream end. Therefore, after exiting the center connection port 424', the fourth fluid flows through the pair of side inlet channels 425 and is introduced into the second separation channel 428 as two streams flowing adjacent to the two sidewalls of the second separation channel 428. The center inlet channel 429 is connected to the second separation channel 428 at or near the center thereof. The fifth fluid, which flows through the center inlet channels 429, is introduced into the center of the second separation channel 428 and is interposed between the two streams of the fourth fluid at or near the upstream end of the second separation channel 428. The pair of side outlet channels 432 are connected to the second separation channel 428 at the two sidewalls thereof, at or near the downstream end. Therefore, the fluid flowing adjacent to the two sidewalls at or near the downstream end of the second separation channel 428 is diverted by the pair of side outlet channels 432 to become the sixth fluid and exits the microfluidic chip 409 through the side outlet port 430. The remaining fluid at or near the center of the second separation channel 428 not diverted by the pair of side outlet channels 432 becomes the seventh fluid and proceeds to exit the microfluidic chip 409 through the center outlet port 434.

FIG. 4G shows the fluidic paths through the microfluidic chip 409 in accordance with the port positions described above. The first and second fluids are introduced into the microfluidic chip 409 through the side and center inlet ports 412 and 416 on the first planar surface 400, respectively. The third fluid is extracted from the microfluidic chip 409 through the side outlet port 420 and the fourth fluid flows into the second network of channels 413 on the second planar surface 402 through the center connection port 424'. The fifth fluid is introduced into the second network of channels 413 through the center inlet port 427. The sixth and seventh fluids are extracted from the microfluidic chip 409 through the side and center outlet ports 430 and 434 on the second planar surface 402, respectively.

The first fluid introduced through the side inlet port 412, which is opened to the exterior of the first lid 406, may be a sample fluid that includes particles or biological objects with different sizes or acoustic contrasts for separation by acoustic radiation pressure, while the second fluid introduced through the center inlet port 416, which is opened to the exterior of the first lid 406, may be a buffer fluid that does not contain any particles or biological objects. After passing through the first separation channel 410, the third fluid extracted from the side outlet port 420, which is opened to the exterior of the first lid 406, may include the particles or biological objects with relatively smaller sizes or lower acoustic contrasts, while the fourth fluid entering the center connection port 424', which is opened to the second planar surface 402, may include the particles or biological objects with relatively larger sizes or higher acoustic contrasts.

The fourth fluid containing the particles or biological objects with relatively larger sizes or higher acoustic contrasts is introduced into the second separation channel 428 through the center connection port 424'. The fifth fluid introduced through the center inlet port 427, which is opened to the exterior of the second lid 408, may be another buffer fluid that does not contain any particles or biological objects. After passing through the second separation channel 428, the sixth fluid extracted from the side outlet port 430, which is opened to the exterior of the second lid 408, may include particles or biological objects with relatively smaller sizes or lower acoustic contrasts among the particles or biological objects in the fourth fluid, and the seventh fluid extracted from the center outlet port 434, which is opened to the exterior of the second lid 408, may include particles or biological objects with relatively larger sizes or higher acoustic contrasts among the particles or biological objects in the fourth fluid. Accordingly, the first and second networks of channels 411 and 413 are fluidically coupled in series.

With continuing reference to FIG. 4G, the microfluidic chip 409 is a part of a microfluidic device 438, which may further include one or more first piezoelectric transducers 440 attached to the exterior of the first lid 406 opposite the first planar surface 400 and/or one or more second piezoelectric transducers 442 attached to the exterior of the second lid 408 opposite the second planar surface 402. The first and second piezoelectric transducers 440 and 442 may be used to generate acoustic pressure waves in the first and second separation channels 410 and 428, respectively. The present invention may be practiced using a single first piezoelectric transducer 440 operating at a first frequency and disposed directly over a portion or the entire length of the first separation channel 410. Alternatively, a cluster of two or more first piezoelectric transducers 440 operating at the first frequency may be disposed directly over and along the first separation channel 410. Likewise, a single second piezoelectric transducer 442 operating at a second frequency may be disposed directly beneath a portion or the entire length of the second separation channel 428. Alternatively, a cluster of two or more second piezoelectric transducers 442 operating at the second frequency may be disposed directly beneath and along the second separation channel 428.

The first piezoelectric transducers 440 may receive power in the form of an oscillating voltage with a frequency in the range of 100 kHz to 100 MHz to generate acoustic pressure waves in the first separation channel 410 between the two sidewalls thereof when a liquid is present. An acoustic standing wave may form in the first separation channel 410 when the channel width, $W_1$, is an integer multiple of one-half wavelength of the acoustic pressure waves, which may depend on the excitation frequency of the power applied to the first piezoelectric transducers 440 and the compressibility and density of the liquid in the first separation channel 410. When $W_1$ is equal to one-half wavelength of the acoustic waves generated by the first piezoelectric transducers 440, a standing wave is formed between the two sidewalls of the first separation channel 410 with a single acoustic pressure node positioned along the center of the first separation channel 410. Objects having relatively larger sizes and/or higher acoustic contrasts may move towards the pressure node at a faster rate, thereby allowing the separation of objects by size or acoustic contrast.

The second piezoelectric transducers 442 may receive power in the form of an oscillating voltage with a frequency in the range of 100 kHz to 100 MHz to generate acoustic pressure waves in the second separation channel 428 between the two sidewalls thereof when a liquid is present. An acoustic standing wave may form in the second separation channel 428 when the channel width, $W_2$, is an integer multiple of one-half wavelength of the acoustic pressure waves, which may depend on the excitation frequency of the power applied to the second piezoelectric transducers 442 and the compressibility and density of the liquid in the second separation channel 428. When $W_2$ is equal to one-half wavelength of the acoustic waves generated by the second piezoelectric transducers 442, a standing wave is formed between the two sidewalls of the second separation channel 428 with a single acoustic pressure node positioned along the center of the second separation channel 428. Objects having relatively larger sizes and/or higher acoustic contrasts may move towards the pressure node, thereby allowing the separation of objects by size or acoustic contrast.

In an embodiment, an acoustic standing wave with single pressure node is formed in each of the first and second separation channels 410 and 428. Accordingly, $W_1$ is equal to one-half of the wavelength of the standing wave in the first separation channel 410, and $W_2$ is equal to one-half of the wavelength of the standing wave in the second separation channel 428. The first and second separation channels 410 and 428 may have the same width (i.e., $W_1=W_2$), which would require the first and second piezoelectric transducers 440 and 442 to operate at substantially the same frequency. Moreover, if sufficient vibration power can be generated by the first or second piezoelectric transducers 440, 442, then only the first piezoelectric transducers 440 or the second piezoelectric transducers 442 may be needed to generate both acoustic standing waves in the first and second separation channels 410 and 428, respectively.

Operation of the microfluidic device 438 under the condition of single pressure node will now be described with reference to FIGS. 4A-4G. A sample fluid containing a first population of first type particles or biological objects 444, a second population of second type particles or biological entities 446, and a third population of third type particles or biological entities 448 is introduced into the side inlet port 412 through the first lid 406 as the first fluid, while a buffer fluid is introduced into the center inlet port 416 through the first lid 406 as the second fluid. The first, second, and third type particles or biological objects 444-448 may have sufficiently different physical sizes and/or acoustic contrasts, such as mass densities and compressibilities, to allow them to be separated by acoustic radiation pressure. For example, the first, second, and third type particles or biological objects 444-448 may have, respectively, large, intermediate, and small physical sizes and/or acoustic contrasts, thereby allowing the acoustic radiation pressure to push the first and second type particles or biological objects 444 and 446 towards the pressure node located along the center of the first separation channel 410 when operating under the single-node condition.

The sample fluid containing the first, second, and third type particles or biological objects 444-448 is introduced into the first separation channel 410 at or near the upstream end thereof via the pair of side inlet channels 414 as two streams flowing adjacent to the sidewalls of the first separation channel 410. The two streams of the sample fluid in the first separation channel 410, which may behave like laminar flow, are interposed by the buffer fluid from the center inlet port 416, which may act as a sheath fluid that retards or prevents the movement of the third type particles or biological objects 448 towards the pressure node positioned along the center of the first separation channel 410. As the sample fluid progresses downstream in the first separation channel 410, the acoustic radiation pressure pushes the first and second type particles or biological objects 444 and 446 towards the pressure node positioned along the center of the first separation channel 410, while the third type particles or biological objects 448 remain mostly close to the sidewalls. At the downstream end of the first separation channel 410, the third type particles or biological objects 448 at or near the sidewalls are diverted through the pair of side outlet channels 422 and into the side outlet port 420 as a part of the third fluid, and the first and second type particles or biological objects 444 and 446 at or near the channel center flow through the center outlet channel 426 and into the center connection port 424' as a part of the fourth fluid.

After exiting the first network of channels 411 on the first planar surface 400 through the center connection port 424', the fourth fluid containing the first and second type particles or biological objects 444 and 446 enters into the second separation channel 428 at or near the upstream end thereof via the pair of side inlet channels 425 as two streams flowing adjacent to the sidewalls of the second separation channel 428. The two streams of the fourth fluid in the second separation channel 428, which may behave like laminar flow, are interposed by the buffer fluid from the center inlet port 427, which may act as a sheath fluid that retards or prevents the movement of the second type particles or biological objects 446 towards the pressure node positioned along the center of the second separation channel 428. As the fourth fluid progresses downstream in the second separation channel 428, the acoustic radiation pressure pushes the first type particles or biological objects 444 towards the pressure node positioned along the center of the second separation channel 428, while the second type particles or biological objects 446 remain mostly close to the sidewalls. At the downstream end of the second separation channel 428, the second type particles or biological objects 446 at or near the sidewalls are diverted through the pair of side outlet channels 432 and into the side outlet port 430 as a part of the sixth fluid, and the first type particles or biological objects 444 at or near the channel center flow through the center outlet channel 436 and into the center outlet port 434 as a part of the seventh fluid.

FIGS. 5A and 5B are, respectively, a top view showing a first planar surface 500 and a bottom view showing a second planar surface 502 of a planar substrate 504 for a microfluidic chip in accordance with another embodiment of the present invention. A first lid 506 is attached to the first planar surface 500 and a second lid 508 is attached to the second planar surface 502 to form the microfluidic chip 509, as shown in the cross-sectional views of FIGS. 5C-5F. The first and second lids 506 and 508 are omitted in FIGS. 5A and 5B for reasons of clarity.

Referring to FIG. 5A, the planar substrate 504 includes a first network of channels 511 recessed from the first planar surface 500 and substantially covered by the first lid 506. The first network of channels 511 includes a first separation channel 510 having an upstream end and a downstream end, a side inlet port 512 for introducing a first fluid into the first separation channel 510, a pair of side inlet channels 514 connecting the side inlet port 512 to the first separation channel 510 at or near the upstream end thereof, a center inlet port 516 for introducing a second fluid into the first separation channel 510, a center inlet channel 518 connecting the center inlet port 516 to the first separation channel 510 at or near the upstream end thereof, a side outlet port 520 for extracting a third fluid from the first separation channel 510, a pair of side outlet channels 522 connecting the side outlet port 520 to the first separation channel 510 at or near the downstream end thereof, a center connection port 524' for extracting a fourth fluid from the first separation channel 510, and an optional center outlet channel 526 connecting the center connection port 524' to the first separation channel 510 at or near the downstream end thereof. The center connection port 524' may alternatively be directly connected to the first separation channel 510 at the downstream end thereof. The first separation channel 510 may have a linear shape with a nominal width, $W_1$, between two sidewalls thereof. $W_1$ may be in the range of approximately 100 µm to 1 mm. One or more of the side inlet channels 514, the center inlet channel 518, the side outlet channels 522, and the center outlet channel 526 may be narrower than the nominal width of the first separation channel 510.

The side and center inlet ports 512, 516 and the side outlet port 520 of the first network of channels 511 on the first planar surface 500 are not bored through the planar substrate 504 as shown in FIGS. 5C and 5F. These ports 512, 516, and 520 are opened to the exterior of the microfluidic chip 509 through the first lid 506, which includes through-holes aligned with the respective ports 512, 516, and 520 of the first network of channels 511. FIG. 5E shows that the center connection port 524' is bored through the planar substrate 504 but is not opened to the exterior of the microfluidic chip 509. The center connection port 524', which is in the form of a through-hole in the planar substrate 504 that is opened to the first and second planar surfaces 500 and 502, allows the fluid to flow from the first network of channels 511 to a second network of channels 513 formed on the second planar surface 502, thereby providing a fluidic connection between the first and second networks of channels 511 and 513 as highlighted by the crosshatch pattern in FIGS. 5A and 5B.

Referring to FIG. 5B, the planar substrate 504 includes the second network of channels 513 recessed from the second planar surface 502 and substantially covered by the second lid 508. The second network of channels 513 includes a second separation channel 528 having an upstream end and a downstream end, a side inlet port 523 for introducing a fifth fluid into the second separation channel 528, a pair of side inlet channels 525 connecting the side inlet port 523 to the second separation channel 528 at or near the upstream end thereof, the center connection port 524' for introducing the fourth fluid into the second separation channel 528, a center inlet channel 529 connecting the center connection port 524' to the second separation channel 528 at or near the upstream end thereof, a side outlet port 530 for extracting a sixth fluid from the second separation channel 528, a pair of side outlet channels 532 connecting the side outlet port 530 to the second separation channel 528 at or near the downstream end thereof, a center outlet port 534 for extracting a seventh fluid from the second separation channel 528, and an optional center outlet channel 536 connecting the center outlet port 534 to the second separation channel 528 at or near the downstream end thereof. The center outlet port 534 may alternatively be directly connected to the second separation channel 528 at the downstream end thereof. The second separation channel 528 may have a linear shape with a nominal width, $W_2$, between two sidewalls thereof. $W_2$ may be in the range of approximately 200 µm to 2 mm. One or more of the side inlet channels 525, the side outlet channels 532, the center inlet channel 529, and the center outlet channel 536 may be narrower than the nominal width of the second separation channel 528.

The side inlet port 523 and the side and center outlet ports 530 and 534 of the second network of channels 513 on the second planar surface 502 are not bored through the planar substrate 504 as shown in FIGS. 5C and 5F. These ports 523, 530, and 534 are opened to the exterior of the microfluidic chip 509 through the second lid 508, which includes through-holes aligned with the respective ports 527, 530, and 534 of the second network of channels 513.

Referring to FIG. 5D, the first separation channel 510 may have a nominal depth, $D_1$, as measured from the first planar surface 500. $D_1$ may be in the range of approximately 50 µm to 500 µm. One or more of the side inlet channels 514, the center inlet channel 518, the side outlet channels 522, and the center outlet channel 526 may be shallower than the nominal depth of the first separation channel 510. The second separation channel 528 may have a nominal depth, $D_2$, as measured from the second planar surface 502. $D_2$ may be in the range of approximately 50 µm to 500 µm. One or more of the side inlet channels 525, the center inlet channel 529, the side outlet channels 532, and the center outlet channel 536 may be shallower than the nominal depth of the second separation channel 528.

While the cross-sectional views of FIGS. 5C-5F may appear to show the ports and channels recessed from the first planar surface 500 and the ports and channels recessed from the second planar surface 502 aligning to each other, features of the first and second networks of channels 513, except for the center connection port 524', do not have to be vertically aligned to practice the present invention.

Referring back to FIG. 5A, the pair of side inlet channels 514 on the first planar surface 500 are connected to the first separation channel 510 at the two sidewalls thereof, near or at the upstream end. Therefore, the first fluid, which flows through the pair of side inlet channels 514, is introduced into the first separation channel 510 as two streams flowing adjacent to the two sidewalls of the first separation channel 510. The center inlet channel 518 is connected to the first separation channel 510 at or near the center thereof. The second fluid, which flows through the center inlet channels 518, is introduced into the center of the first separation channel 510 and is interposed between the two streams of the first fluid at or near the upstream end of the first separation channel 510. The pair of side outlet channels 522 are connected to the first separation channel 510 at the two sidewalls thereof, at or near the downstream end. Therefore, the fluid flowing adjacent to the two sidewalls at or near the downstream end of the first separation channel 510 is diverted by the pair of side outlet channels 522 to become the third fluid and exits the microfluidic chip 509 through the side outlet port 520. The remaining fluid at or near the center of the first separation channel 510 not diverted by the pair of side outlet channels 522 becomes the fourth fluid and proceeds to flow through the center outlet channel 526 and into the center connection port 524', which provides a fluidic connection to the upstream end of the second separation channel 528 on the second planar surface 502.

Referring to FIG. 5B, the pair of side inlet channels 525 on the second planar surface 502 are connected to the second separation channel 528 at the two sidewalls thereof, near or at the upstream end. Therefore, the fifth fluid, which flows through the pair of side inlet channels 525, is introduced into the second separation channel 528 as two streams flowing adjacent to the two sidewalls of the second separation channel 528. The center inlet channel 529 is connected to the second separation channel 528 at or near the center thereof. After exiting the center connection port 524', the fourth fluid, which flows through the center inlet channels 529, is introduced into the center of the second separation channel 528 and is interposed between the two streams of the fifth fluid at or near the upstream end of the second separation channel 528. The pair of side outlet channels 532 are connected to the second separation channel 528 at the two sidewalls thereof, at or near the downstream end. Therefore, the fluid flowing adjacent to the two sidewalls at or near the downstream end of the second separation channel 528 is diverted by the pair of side outlet channels 532 to become the sixth fluid and exits the microfluidic chip 509 through the side outlet port 530. The remaining fluid at or near the center of the second separation channel 528 not diverted by the pair of side outlet channels 532 becomes the seventh fluid and proceeds to exit the microfluidic chip 509 through the center outlet port 534.

FIG. 5G shows the fluidic paths through the microfluidic chip 509 in accordance with the port positions described above. The first and second fluids are introduced into the microfluidic chip 509 through the side and center inlet ports 512 and 516 on the first planar surface 500, respectively. The third fluid is extracted from the microfluidic chip 509 through the side outlet port 520 and the fourth fluid flows into the second network of channels 513 on the second planar surface 502 through the center connection port 524'. The fifth fluid is introduced into the second network of channels 513 through the side inlet port 523. The sixth and seventh fluids are extracted from the microfluidic chip 509 through the side and center outlet ports 530 and 534 on the second planar surface 502, respectively.

The first fluid introduced through the side inlet port 512, which is opened to the exterior of the first lid 506, may be a sample fluid that includes particles or biological objects with different sizes or acoustic contrasts for separation by acoustic radiation pressure, while the second fluid introduced through the center inlet port 516, which is opened to the exterior of the first lid 506, may be a buffer fluid that does not contain any particles or biological objects. After passing through the first separation channel 510, the third fluid extracted from the side outlet port 520, which is opened to the exterior of the first lid 506, may include the particles or biological objects with relatively smaller sizes or lower acoustic contrasts, while the fourth fluid entering the center connection port 524', which is opened to the second planar surface 502, may include the particles or biological objects with relatively larger sizes or higher acoustic contrasts.

The fourth fluid containing the particles or biological objects with relatively larger sizes or higher acoustic contrasts is introduced into the second separation channel 528 through the center connection port 524'. The fifth fluid introduced through the side inlet port 523, which is opened to the exterior of the second lid 508, may be another buffer fluid that does not contain any particles or biological objects. After passing through the second separation channel 528, the sixth fluid extracted from the side outlet port 530, which is opened to the exterior of the second lid 508, may include particles or biological objects with relatively larger sizes or higher acoustic contrasts among the particles or biological objects in the fourth fluid, and the seventh fluid extracted from the center outlet port 534, which is opened to the exterior of the second lid 508, may include particles or biological objects with relatively smaller sizes or lower acoustic contrasts among the particles or biological objects in the fourth fluid. Accordingly, the first and second networks of channels 511 and 513 are fluidically coupled in series.

With continuing reference to FIG. 5G, the microfluidic chip 509 is a part of a microfluidic device 538, which may further include one or more first piezoelectric transducers 540 attached to the exterior of the first lid 506 opposite the first planar surface 500 and/or one or more second piezoelectric transducers 542 attached to the exterior of the second lid 508 opposite the second planar surface 502. The first and second piezoelectric transducers 540 and 542 may be used to generate acoustic pressure waves in the first and second separation channels 510 and 528, respectively. The present invention may be practiced using a single first piezoelectric transducer 540 operating at a first frequency and disposed directly over a portion or the entire length of the first separation channel 510. Alternatively, a cluster of two or more first piezoelectric transducers 540 operating at the first frequency may be disposed directly over and along the first separation channel 510. Likewise, a single second piezoelectric transducer 542 operating at a second frequency may be disposed directly beneath a portion or the entire length of the second separation channel 528. Alternatively, a cluster of two or more second piezoelectric transducers 542 operating at the second frequency may be disposed directly beneath and along the second separation channel 528.

The first piezoelectric transducers 540 may receive power in the form of an oscillating voltage with a frequency in the range of 100 kHz to 100 MHz to generate acoustic pressure waves in the first separation channel 510 between the two sidewalls thereof when a liquid is present. An acoustic standing wave may form in the first separation channel 510 when the channel width, $W_1$, is an integer multiple of one-half wavelength of the acoustic pressure waves, which may depend on the excitation frequency of the power applied to the first piezoelectric transducers 540 and the compressibility and density of the liquid in the first separation channel 510. When $W_1$ is equal to one-half wavelength of the acoustic waves generated by the first piezoelectric transducers 540, a standing wave is formed between the two sidewalls of the first separation channel 510 with a single acoustic pressure node positioned along the center of the first separation channel 510. Objects having relatively larger sizes and/or higher acoustic contrasts may move towards the pressure node at a faster rate, thereby allowing the separation of objects by size or acoustic contrast.

The second piezoelectric transducers 542 may receive power in the form of an oscillating voltage with a frequency in the range of 100 kHz to 100 MHz to generate acoustic pressure waves in the second separation channel 528 between the two sidewalls thereof when a liquid is present. An acoustic standing wave may form in the second separation channel 528 when the channel width, $W_2$, is an integer multiple of one-half wavelength of the acoustic pressure waves, which may depend on the excitation frequency of the power applied to the second piezoelectric transducers 542 and the compressibility and density of the liquid in the second separation channel 528. When $W_2$ is equal to one wavelength of the acoustic waves generated by the second piezoelectric transducers 542, a standing wave is formed between the two sidewalls of the second separation channel 528 with two acoustic pressure nodes positioned, respectively, at a distance of $W_2/4$ from the two sidewalls of the second separation channel 528. Objects having relatively larger sizes and/or higher acoustic contrasts may move towards the two pressure nodes, thereby allowing the separation of objects by size or acoustic contrast.

In an embodiment, an acoustic standing wave with single pressure node is formed in the first separation channel 510, and another acoustic standing wave with two pressure nodes is formed in the second separation channel 528. Accordingly, $W_1$ is equal to one-half of the wavelength of the standing wave in the first separation channel 510, and $W_2$ is equal to one wavelength of the standing wave in the second separation channel 528. The second separation channel 528 may be twice as wide as the first separation channel 510 (i.e., $2W_1=W_2$), which would require the first and second piezoelectric transducers 540 and 542 to operate at substantially the same frequency. Moreover, if sufficient vibration power can be generated by the first or second piezoelectric transducers 540, 542, then only the first piezoelectric transducers 540 or the second piezoelectric transducers 542 may be needed to generate both acoustic standing waves in the first and second separation channels 510 and 528, respectively.

Operation of the microfluidic device 538 under the condition of single and two pressure nodes in the first and second separation channels 510 and 528, respectively, will now be described with reference to FIGS. 5A-5G. A sample fluid containing a first population of first type particles or biological objects 544, a second population of second type particles or biological entities 546, and a third population of third type particles or biological entities 548 is introduced into the side inlet port 512 through the first lid 506 as the first fluid, while a buffer fluid is introduced into the center inlet port 516 through the first lid 506 as the second fluid. The first, second, and third type particles or biological objects 544-548 may have sufficiently different physical sizes and/or acoustic contrasts, such as mass densities and compressibilities, to allow them to be separated by acoustic radiation pressure. For example, the first, second, and third type particles or biological objects 544-548 may have, respectively, large, intermediate, and small physical sizes and/or acoustic contrasts, thereby allowing the acoustic radiation pressure to push the first and second type particles or biological objects 544 and 546 towards the pressure node located along the center of the first separation channel 510 when operating under the single-node condition.

The sample fluid containing the first, second, and third type particles or biological objects 544-548 is introduced into the first separation channel 510 at or near the upstream end thereof via the pair of side inlet channels 514 as two streams flowing adjacent to the sidewalls of the first separation channel 510. The two streams of the sample fluid in the first separation channel 510, which may behave like laminar flow, are interposed by the buffer fluid from the center inlet port 516, which may act as a sheath fluid that retards or prevents the movement of the third type particles or biological objects 548 towards the pressure node positioned along the center of the first separation channel 510. As the sample fluid progresses downstream in the first separation channel 510, the acoustic radiation pressure pushes the first and second type particles or biological objects 544 and 546 towards the pressure node positioned along the center of the first separation channel 510, while the third type particles or biological objects 548 remain mostly close to the sidewalls. At the downstream end of the first separation channel 510, the third type particles or biological objects 548 at or near the sidewalls are diverted through the pair of side outlet channels 522 and into the side outlet port 520 as a part of the third fluid, and the first and second type particles or biological objects 544 and 546 at or near the channel center flow through the center outlet channel 526 and into the center connection port 524' as a part of the fourth fluid.

After exiting the first network of channels 511 on the first planar surface 500 through the center connection port 524', the fourth fluid containing the first and second type particles or biological objects 544 and 546 enters into the second separation channel 528 at or near the upstream end thereof via the center inlet channels 529 as a stream flowing along the center of the second separation channel 528. The buffer fluid, or the fifth fluid, is introduced into the second separation channel 528 at or near the upstream end thereof via the pair of side inlet channels 525 as two streams flowing adjacent to the sidewalls of the second separation channel 528. At or near the upstream end of the second separation channel 528, the stream of the fourth fluid, which may behave like laminar flow, is interposed between the two streams of the buffer fluid, which may act as a sheath fluid that retards or prevents the movement of the second type particles or biological objects 546 towards the two off-center pressure nodes positioned $W_2/4$ from the two sidewalls of the second separation channel 528, respectively. As the fourth fluid progresses downstream in the second separation channel 528, the acoustic radiation pressure pushes the first type particles or biological objects 544 towards the two off-center pressure nodes positioned $W_2/4$ from the two sidewalls of the second separation channel 528, while the second type particles or biological objects 546 remain mostly along the center of the second separation channel 528. At the downstream end of the second separation channel 528, the first type particles or biological objects 544 at or near the sidewalls are diverted through the pair of side outlet channels 532 and into the side outlet port 530 as a part of the sixth fluid, and the second type particles or biological objects 546 at or near the channel center flow through the center outlet channel 536 and into the center outlet port 534 as a part of the seventh fluid.

FIGS. 6A and 6B are, respectively, a top view showing a first planar surface 600 and a bottom view showing a second planar surface 602 of a planar substrate 604 for a microfluidic chip in accordance with another embodiment of the present invention. A first lid 606 is attached to the first planar surface 600 and a second lid 608 is attached to the second planar surface 602 to form the microfluidic chip 609, as shown in the cross-sectional views of FIGS. 6C-6F. The first and second lids 606 and 608 are omitted in FIGS. 6A and 6B for reasons of clarity.

Referring to FIG. 6A, the planar substrate 604 includes a first network of channels 611 recessed from the first planar surface 600 and substantially covered by the first lid 206. The first network of channels 611 includes a first separation channel 610 having an upstream end and a downstream end, a side inlet port 612 for introducing a first fluid into the first separation channel 610, a pair of side inlet channels 614 connecting the side inlet port 612 to the first separation channel 610 at or near the upstream end thereof, a center inlet port 616 for introducing a second fluid into the first separation channel 610, a center inlet channel 618 connecting the center inlet port 616 to the first separation channel 610 at or near the upstream end thereof, a side connection port 620' for extracting a third fluid from the first separation channel 610, a pair of side outlet channels 622 connecting the side connection port 620' to the first separation channel 610 at or near the downstream end thereof, a center outlet port 624 for extracting a fourth fluid from the first separation channel 610, and an optional center outlet channel 626 connecting the center outlet port 624 to the first separation channel 610 at or near the downstream end thereof. The center outlet port 624 may alternatively be directly connected to the first separation channel 610 at the downstream end thereof. The first separation channel 610 may have a linear shape with a nominal width, $W_1$, between two sidewalls thereof. $W_1$ may be in the range of approximately 100 µm to 1 mm. One or more of the side inlet channels 614, the center inlet channel 618, the side outlet channels 622, and the center outlet channel 626 may be narrower than the nominal width of the first separation channel 610.

The side and center inlet ports 612, 616 and the center outlet port 624 of the first network of channels 611 on the first planar surface 600 are not bored through the planar substrate 604 as shown in FIGS. 6C and 6E. These ports 612, 616, and 624 are opened to the exterior of the microfluidic chip 609 through the first lid 606, which includes through-holes aligned with the respective ports 612, 616, and 624 of the first network of channels 611. FIG. 6F shows that the side connection port 620' is bored through the planar substrate 604 but is not opened to the exterior of the microfluidic chip 609. The side connection port 620', which is in the form of a through-hole in the planar substrate 604 that is opened to the first and second planar surfaces 600 and 602, allows the fluid to flow from the first network of channels 611 to a second network of channels 613 formed on the second planar surface 602, thereby providing a fluidic connection between the first and second networks of channels 611 and 613 as highlighted by the crosshatch pattern in FIGS. 6A and 6B.

Referring to FIG. 6B, the planar substrate 604 includes the second network of channels 613 recessed from the second planar surface 602 and substantially covered by the second lid 608. The second network of channels 613 includes a second separation channel 628 having an upstream end and a downstream end, the side connection port 620' for introducing the third fluid into the second separation channel 628, a pair of side inlet channels 625 connecting the side connection port 620' to the second separation channel 628 at or near the upstream end thereof, a center inlet port 627 for introducing a fifth fluid into the second separation channel 628, a center inlet channel 629 connecting the center inlet port 627 to the second separation channel 628 at or near the upstream end thereof, a side outlet port 630 for extracting a sixth fluid from the second separation channel 628, a pair of side outlet channels 632 connecting the side outlet port 630 to the second separation channel 628 at or near the downstream end thereof, a center outlet port 634 for extracting a seventh fluid from the second separation channel 628, and an optional center outlet channel 636 connecting the center outlet port 634 to the second separation channel 628 at or near the downstream end thereof. The center outlet port 634 may alternatively be directly connected to the second separation channel 628 at the downstream end thereof. The second separation channel 628 may have a linear shape with a nominal width, $W_2$, between two sidewalls thereof. $W_2$ may be in the range of approximately 100 µm to 1 mm. One or more of the side inlet channels 625, the side outlet channels 632, the center inlet channel 629, and the center outlet channel 636 may be narrower than the nominal width of the second separation channel 628.

The center inlet port 627 and the side and center outlet ports 630 and 634 of the second network of channels 613 on the second planar surface 602 are not bored through the planar substrate 604 as shown in FIGS. 6C and 6E. These ports 627, 630, and 634 are opened to the exterior of the microfluidic chip 609 through the second lid 608, which includes through-holes aligned with the respective ports 627, 630, and 634 of the second network of channels 613.

Referring to FIG. 6D, the first separation channel 610 may have a nominal depth, $D_1$, as measured from the first planar surface 600. $D_1$ may be in the range of approximately 50 µm to 500 µm. One or more of the side inlet channels 614, the center inlet channel 618, the side outlet channels 622, and the center outlet channel 626 may be shallower than the nominal depth of the first separation channel 610. The second separation channel 628 may have a nominal depth, $D_2$, as measured from the second planar surface 602. $D_2$ may be in the range of approximately 50 µm to 500 µm. One or more of the side inlet channels 625, the center inlet channel 629, the side outlet channels 632, and the center outlet channel 636 may be shallower than the nominal depth of the second separation channel 628.

While the cross-sectional views of FIGS. 6C and 6D may appear to show the ports and channels recessed from the first planar surface 600 and the ports and channels recessed from the second planar surface 602 aligning to each other, features of the first and second networks of channels 611 and 613, except for the side connection port 620', do not have to be vertically aligned to practice the present invention.

Referring back to FIG. 6A, the pair of side inlet channels 614 on the first planar surface 600 are connected to the first separation channel 610 at the two sidewalls thereof, near or at the upstream end. Therefore, the first fluid, which flows through the pair of side inlet channels 614, is introduced into the first separation channel 610 as two streams flowing adjacent to the two sidewalls of the first separation channel 610. The center inlet channel 618 is connected to the first separation channel 610 at or near the center thereof. The second fluid, which flows through the center inlet channels 618, is introduced into the center of the first separation channel 610 and is interposed between the two streams of the first fluid at or near the upstream end of the first separation channel 610. The pair of side outlet channels 622 are connected to the first separation channel 610 at the two sidewalls thereof, at or near the downstream end. Therefore, the fluid flowing adjacent to the two sidewalls at or near the downstream end of the first separation channel 610 is diverted by the pair of side outlet channels 622 to become the third fluid and flows into the side connection port 620', which provides a fluidic connection to the upstream end of the second separation channel 628 on the second planar surface 602. The remaining fluid at or near the center of the first separation channel 610 not diverted by the pair of side outlet channels 622 becomes the fourth fluid and proceeds to flow through the center outlet channel 626 and exit the microfluidic chip 609 through the center outlet port 624.

Referring to FIG. 6B, the pair of side inlet channels 625 on the second planar surface 602 are connected to the second separation channel 628 at the two sidewalls thereof, near or at the upstream end. Therefore, after exiting the side connection port 620', the third fluid flows through the pair of side inlet channels 625 and is introduced into the second separation channel 628 as two streams flowing adjacent to the two sidewalls of the second separation channel 628. The center inlet channel 629 is connected to the second separation channel 628 at or near the center thereof. The fifth fluid, which flows through the center inlet channels 629, is introduced into the center of the second separation channel 628 and is interposed between the two streams of the third fluid at or near the upstream end of the second separation channel 628. The pair of side outlet channels 632 are connected to the second separation channel 628 at the two sidewalls thereof, at or near the downstream end. Therefore, the fluid flowing adjacent to the two sidewalls at or near the downstream end of the second separation channel 628 is diverted by the pair of side outlet channels 632 to become the sixth fluid and exits the microfluidic chip 609 through the side outlet port 630. The remaining fluid at or near the center of the second separation channel 628 not diverted by the pair of side outlet channels 632 becomes the seventh fluid and proceeds to exit the microfluidic chip 609 through the center outlet port 634.

FIG. 6G shows the fluidic paths through the microfluidic chip 609 in accordance with the port positions described above. The first and second fluids are introduced into the microfluidic chip 609 through the side and center inlet ports 612 and 616 on the first planar surface 600, respectively. The third fluid flows into the second network of channels 613 on the second planar surface 602 through the side connection port 620'. The fourth fluid is extracted from the microfluidic chip 609 through the center outlet port 624. The fifth fluid is introduced into the second network of channels 613 through the center inlet port 627. The sixth and seventh fluids are extracted from the microfluidic chip 609 through the side and center outlet ports 630 and 634 on the second planar surface 602, respectively.

The first fluid introduced through the side inlet port 612, which is opened to the exterior of the first lid 606, may be a sample fluid that includes particles or biological objects with different sizes or acoustic contrasts for separation by acoustic radiation pressure, while the second fluid introduced through the center inlet port 616, which is opened to the exterior of the first lid 606, may be a buffer fluid that does not contain any particles or biological objects. After passing through the first separation channel 610, the fourth fluid extracted from the center outlet port 624, which is opened to the exterior of the first lid 606, may include the particles or biological objects with relatively larger sizes or higher acoustic contrasts, while the third fluid entering the side connection port 620', which is opened to the second planar surface 602, may include the particles or biological objects with relatively smaller sizes or lower acoustic contrasts.

The third fluid containing the particles or biological objects with relatively smaller sizes or lower acoustic contrasts is introduced into the second separation channel 628 through the side connection port 620'. The fifth fluid introduced through the center inlet port 627, which is opened to the exterior of the second lid 608, may be another buffer fluid that does not contain any particles or biological objects. After passing through the second separation channel 628, the sixth fluid extracted from the side outlet port 630, which is opened to the exterior of the second lid 608, may include particles or biological objects with relatively smaller sizes or lower acoustic contrasts among the particles or biological objects in the third fluid, and the seventh fluid extracted from the center outlet port 634, which is opened to the exterior of the second lid 608, may include particles or biological objects with relatively larger sizes or higher acoustic contrasts among the particles or biological objects in the third fluid. Accordingly, the first and second networks of channels 611 and 613 are fluidically coupled in series.

With continuing reference to FIG. 6G, the microfluidic chip 609 is a part of a microfluidic device 638, which may further include one or more first piezoelectric transducers 640 attached to the exterior of the first lid 606 opposite the first planar surface 600 and/or one or more second piezoelectric transducers 642 attached to the exterior of the second lid 608 opposite the second planar surface 602. The first and second piezoelectric transducers 640 and 642 may be used to generate acoustic pressure waves in the first and second separation channels 610 and 628, respectively. The present invention may be practiced using a single first piezoelectric transducer 640 operating at a first frequency and disposed directly over a portion or the entire length of the first separation channel 610. Alternatively, a cluster of two or more first piezoelectric transducers 640 operating at the first frequency may be disposed directly over and along the first separation channel 610. Likewise, a single second piezoelectric transducer 642 operating at a second frequency may be disposed directly beneath a portion or the entire length of the second separation channel 628. Alternatively, a cluster of two or more second piezoelectric transducers 642 operating at the second frequency may be disposed directly beneath and along the second separation channel 628.

The first piezoelectric transducers 640 may receive power in the form of an oscillating voltage with a frequency in the range of 100 kHz to 100 MHz to generate acoustic pressure waves in the first separation channel 610 between the two sidewalls thereof when a liquid is present. An acoustic standing wave may form in the first separation channel 610 when the channel width, $W_1$, is an integer multiple of one-half wavelength of the acoustic pressure waves, which may depend on the excitation frequency of the power applied to the first piezoelectric transducers 640 and the compressibility and density of the liquid in the first separation channel 610. When $W_1$ is equal to one-half wavelength of the acoustic waves generated by the first piezoelectric transducers 640, a standing wave is formed between the two sidewalls of the first separation channel 610 with a single acoustic pressure node positioned along the center of the first separation channel 610. Objects having relatively larger sizes and/or higher acoustic contrasts may move towards the pressure node at a faster rate, thereby allowing the separation of objects by size or acoustic contrast.

The second piezoelectric transducers 642 may receive power in the form of an oscillating voltage with a frequency in the range of 100 kHz to 100 MHz to generate acoustic pressure waves in the second separation channel 628 between the two sidewalls thereof when a liquid is present. An acoustic standing wave may form in the second separation channel 628 when the channel width, $W_2$, is an integer multiple of one-half wavelength of the acoustic pressure waves, which may depend on the excitation frequency of the power applied to the second piezoelectric transducers 642 and the compressibility and density of the liquid in the second separation channel 628. When $W_2$ is equal to one-half wavelength of the acoustic waves generated by the second piezoelectric transducers 642, a standing wave is formed between the two sidewalls of the second separation channel 628 with a single acoustic pressure node positioned along the center of the second separation channel 628.

Objects having relatively larger sizes and/or higher acoustic contrasts may move towards the pressure node, thereby allowing the separation of objects by size or acoustic contrast.

In an embodiment, an acoustic standing wave with single pressure node is formed in each of the first and second separation channels 610 and 628. Accordingly, $W_1$ is equal to one-half of the wavelength of the standing wave in the first separation channel 610, and $W_2$ is equal to one-half of the wavelength of the standing wave in the second separation channel 628. The first and second separation channels 610 and 628 may have the same width (i.e., $W_1=W_2$), which would require the first and second piezoelectric transducers 640 and 642 to operate at substantially the same frequency. Moreover, if sufficient vibration power can be generated by the first or second piezoelectric transducers 640, 642, then only the first piezoelectric transducers 640 or the second piezoelectric transducers 642 may be needed to generate both acoustic standing waves in the first and second separation channels 610 and 628, respectively.

Operation of the microfluidic device 638 under the condition of single pressure node will now be described with reference to FIGS. 6A-6G. A sample fluid containing a first population of first type particles or biological objects 644, a second population of second type particles or biological entities 646, and a third population of third type particles or biological entities 648 is introduced into the side inlet port 612 through the first lid 606 as the first fluid, while a buffer fluid is introduced into the center inlet port 616 through the first lid 606 as the second fluid. The first, second, and third type particles or biological objects 644-648 may have sufficiently different physical sizes and/or acoustic contrasts, such as mass densities and compressibilities, to allow them to be separated by acoustic radiation pressure. For example, the first, second, and third type particles or biological objects 644-648 may have, respectively, large, intermediate, and small physical sizes and/or acoustic contrasts, thereby allowing the acoustic radiation pressure to push the first type particles or biological objects 644 towards the pressure node located along the center of the first separation channel 610 when operating under the single-node condition.

The sample fluid containing the first, second, and third type particles or biological objects 644-648 is introduced into the first separation channel 610 at or near the upstream end thereof via the pair of side inlet channels 614 as two streams flowing adjacent to the sidewalls of the first separation channel 610. The two streams of the sample fluid in the first separation channel 610, which may behave like laminar flow, are interposed by the buffer fluid from the center inlet port 616, which may act as a sheath fluid that retards or prevents the movement of the second and third type particles or biological objects 646 and 648 towards the pressure node positioned along the center of the first separation channel 610. As the sample fluid progresses downstream in the first separation channel 610, the acoustic radiation pressure pushes the first type particles or biological objects 644 towards the pressure node positioned along the center of the first separation channel 610, while the second and third type particles or biological objects 646 and 648 remain mostly close to the sidewalls. At the downstream end of the first separation channel 610, the second and third type particles or biological objects 646 and 648 at or near the sidewalls are diverted through the pair of side outlet channels 622 and into the side connection port 620' as a part of the third fluid, and the first type particles or biological objects 644 at or near the channel center flow through the center outlet channel 626 and into the center outlet port 624 as a part of the fourth fluid.

After exiting the first network of channels 611 on the first planar surface 600 through the side connection port 620', the third fluid containing the second and third type particles or biological objects 646 and 648 enters into the second separation channel 628 at or near the upstream end thereof via the pair of side inlet channels 625 as two streams flowing adjacent to the sidewalls of the second separation channel 628. The two streams of the third fluid in the second separation channel 628, which may behave like laminar flow, are interposed by the buffer fluid from the center inlet port 627, which may act as a sheath fluid that retards or prevents the movement of the third type particles or biological objects 648 towards the pressure node positioned along the center of the second separation channel 628. As the third fluid progresses downstream in the second separation channel 628, the acoustic radiation pressure pushes the second type particles or biological objects 646 towards the pressure node positioned along the center of the second separation channel 628, while the third type particles or biological objects 648 remain mostly close to the sidewalls. At the downstream end of the second separation channel 628, the third type particles or biological objects 648 at or near the sidewalls are diverted through the pair of side outlet channels 632 and into the side outlet port 630 as a part of the sixth fluid, and the second type particles or biological objects 646 at or near the channel center flow through the center outlet channel 636 and into the center outlet port 634 as a part of the seventh fluid.

FIGS. 7A and 7B are, respectively, a top view showing a first planar surface 700 and a bottom view showing a second planar surface 702 of a planar substrate 704 for a microfluidic chip in accordance with another embodiment of the present invention. A first lid 706 is attached to the first planar surface 700 and a second lid 708 is attached to the second planar surface 702 to form the microfluidic chip 709, as shown in the cross-sectional views of FIGS. 6C-6F. The first and second lids 706 and 708 are omitted in FIGS. 7A and 7B for reasons of clarity.

Referring to FIG. 7A, the planar substrate 704 includes a first network of channels 711 recessed from the first planar surface 700 and substantially covered by the first lid 706. The first network of channels 711 includes a first separation channel 710 having an upstream end and a downstream end, a side-inlet connection port 712' for introducing a first portion of a first fluid into the first separation channel 710, a pair of side inlet channels 714 connecting the side-inlet connection port 712' to the first separation channel 710 at or near the upstream end thereof, a center-inlet connection port 716' for introducing a first portion of a second fluid into the first separation channel 710, a center inlet channel 718 connecting the center-inlet connection port 716' to the first separation channel 710 at or near the upstream end thereof, a side-outlet connection port 720' for extracting a first portion of a third fluid from the first separation channel 710, a pair of side outlet channels 722 connecting the side-outlet connection port 720' to the first separation channel 710 at or near the downstream end thereof, a center-outlet connection port 724' for extracting a first portion of a fourth fluid from the first separation channel 710, and an optional center outlet channel 726 connecting the center-outlet connection port 724' to the first separation channel 710 at or near the downstream end thereof. The center-outlet connection port 724' may alternatively be directly connected to the first separation channel 710 at the downstream end thereof. The first separation channel 710 may have a linear shape with a nominal width, $W_1$, between two sidewalls thereof. $W_1$ may be in the range of approximately 100 μm to 1 mm. One or more of the side inlet channels 714, the center inlet channel 718, the side outlet channels 722, and the center outlet channel 726 may be narrower than the nominal width of the first separation channel 710.

The side-inlet and center-inlet connection ports 712', 716' and the side-outlet and center-outlet connection ports 720', 724' are bored through the planar substrate 704 and may be opened to the exterior of the microfluidic chip 709 through the first lid 706, which includes through-holes aligned with the respective ports 712', 716', 720', and 724', as shown in FIGS. 7C, 7E, and 7F. These ports 712', 716', 720', and 724', which are in the form of through-holes in the planar substrate 704 that are opened to the first and second planar surfaces 700 and 702, allows the fluid to flow from the first network of channels 711 to a second network of channels 713 formed on the second planar surface 702, thereby providing fluidic connections between the first and second networks of channels 711 and 713 as highlighted by the crosshatch pattern in FIGS. 7A and 7B.

Referring to FIG. 7B, the planar substrate 704 includes the second network of channels 713 recessed from the second planar surface 702 and substantially covered by the second lid 708. The second network of channels 713 includes a second separation channel 728 having an upstream end and a downstream end, the side-inlet connection port 712' for introducing a second portion of the first fluid into the second separation channel 728, a pair of side inlet channels 732 connecting the side-inlet connection port 712' to the second separation channel 728 at or near the upstream end thereof, the center-inlet connection port 716' for introducing a second portion of the second fluid into the second separation channel 728, a center inlet channel 736 connecting the center-inlet connection port 716' to the second separation channel 728 at or near the upstream end thereof, the side-outlet connection port 720' for extracting a second portion of the third fluid from the second separation channel 728, a pair of side outlet channels 725 connecting the side-outlet connection port 720' to the second separation channel 728 at or near the downstream end thereof, a center-outlet connection port 724' for extracting a second portion of the fourth fluid from the second separation channel 728, and an optional center outlet channel 729 connecting the center-outlet connection port 724' to the second separation channel 728 at or near the downstream end thereof. The center-outlet connection port 724' may alternatively be directly connected to the second separation channel 728 at the downstream end thereof. The second separation channel 728 may have a linear shape with a nominal width, $W_2$, between two sidewalls thereof. $W_2$ may be in the range of approximately 100 μm to 1 mm. One or more of the side inlet channels 732, the center inlet channel 736, the side outlet channels 725, and the center outlet channel 729 may be narrower than the nominal width of the second separation channel 728.

Referring to FIG. 7D, the first separation channel 710 may have a nominal depth, $D_1$, as measured from the first planar surface 700. $D_1$ may be in the range of approximately 50 μm to 500 μm. One or more of the side inlet channels 714, the center inlet channel 718, the side outlet channels 722, and the center outlet channel 726 may be shallower than the nominal depth of the first separation channel 710. The second separation channel 728 may have a nominal depth, $D_2$, as measured from the second planar surface 702. $D_2$ may be in the range of approximately 50 μm to 500 μm. One or more of the side inlet channels 725, the center inlet channel 729, the side outlet channels 732, and the center outlet channel 736 may be shallower than the nominal depth of the second separation channel 728.

It is worth noting that while FIGS. 7C, 7E, and 7F show all the ports 712', 716', 720', and 724' are opened to the exterior of the microfluidic chip 709 through the first lid 706, each of the ports 712', 716', 720', and 724' may be independently opened to the exterior of the microfluidic chip 709 through the first lid 706 or the second lid 708. For example, the side-inlet and center-inlet connection ports 712' and 716' may be opened to the exterior of the first lid 706, while the side-outlet and center-outlet connection ports 720' and 724' may be opened to the exterior of the second lid 708.

The first fluid flows through the side-inlet connection port 712' and into the first and second separation channels 710 and 728 via the side inlet channels 714 and 732, respectively. The second fluid flows through the center-inlet connection port 716' and into the first and second separation channels 710 and 728 via the center inlet channels 718 and 736, respectively. The third fluid, which exits the microfluidic chip by way of the side-outlet connection port 720', is collected from the first and second separation channels 710 and 728 via the side outlet channels 722 and 725, respectively. The fourth fluid, which exits the microfluidic chip by way of the center-outlet connection port 724', is collected from the first and second separation channels 710 and 728 via the center outlet channels 726 and 729, respectively.

Referring back to FIG. 7A, the pair of side inlet channels 714 on the first planar surface 700 are connected to the first separation channel 710 at the two sidewalls thereof, near or at the upstream end. Therefore, the first portion of the first fluid, which flows through the pair of side inlet channels 714, is introduced into the first separation channel 710 as two streams flowing adjacent to the two sidewalls of the first separation channel 710. The center inlet channel 718 is connected to the first separation channel 710 at or near the center thereof. The first portion of the second fluid, which flows through the center inlet channels 718, is introduced into the center of the first separation channel 710 and is interposed between the two streams of the first portion of the first fluid at or near the upstream end of the first separation channel 710. The pair of side outlet channels 722 are connected to the first separation channel 710 at the two sidewalls thereof, at or near the downstream end. Therefore, the fluid flowing adjacent to the two sidewalls at or near the downstream end of the first separation channel 710 is diverted by the pair of side outlet channels 722 to become the first portion of the third fluid and exits the microfluidic chip 709 through the side-outlet connection port 720'. The remaining fluid at or near the center of the first separation channel 710 not diverted by the pair of side outlet channels 722 becomes the first portion of the fourth fluid and proceeds to flow through the center outlet channel 726 and exit the microfluidic chip 709 through the center-outlet connection port 724'.

Referring to FIG. 7B, the pair of side inlet channels 732 on the second planar surface 702 are connected to the second separation channel 728 at the two sidewalls thereof, near or at the upstream end. Therefore, the second portion of the first fluid, which flows through the pair of side inlet channels 732, is introduced into the second separation channel 728 as two streams flowing adjacent to the two sidewalls of the second separation channel 728. The center inlet channel 736 is connected to the second separation channel 728 at or near the center thereof. The second portion of the second fluid, which flows through the center inlet channels 736, is introduced into the center of the second separation channel 728 and is interposed between the two streams of the second portion of the first fluid at or near the upstream end of the second separation channel 728. The pair of side outlet channels 725 are connected to the second separation channel 728 at the two sidewalls thereof, at or near the downstream end. Therefore, the fluid flowing adjacent to the two sidewalls at or near the downstream end of the second separation channel 728 is diverted by the pair of side outlet channels 725 to become the second portion of the third fluid and exits the microfluidic chip 709 through the side-outlet connection port 720'. The remaining fluid at or near the center of the first separation channel 728 not diverted by the pair of side outlet channels 725 becomes the second portion of the fourth fluid and proceeds to flow through the center outlet channel 729 and exit the microfluidic chip 709 through the center-outlet connection port 724'.

FIG. 7G shows the fluidic paths through the microfluidic chip 709 in accordance with the port positions described above. The first and second fluids are introduced into the microfluidic chip 709 through the side-inlet and center-inlet connection ports 712' and 716' on the first planar surface 700, respectively. The third and fourth fluids are extracted from the side-outlet and center-outlet connection ports 720' and 724' on the first planar surface 700, respectively.

The first fluid introduced through the side-inlet connection port 712', which is opened to the exterior of the first lid 706, may be a sample fluid that includes particles or biological objects with different sizes or acoustic contrasts for separation by acoustic radiation pressure, while the second fluid introduced through the center-inlet connection port 716, which is opened to the exterior of the first lid 706, may be a buffer fluid that does not contain any particles or biological objects. After passing through the first and second separation channels 710 and 728, the third fluid extracted from the side-outlet connection port 720', which is opened to the exterior of the first lid 706, may include the particles or biological objects with relatively smaller sizes or lower acoustic contrasts, while the fourth fluid extracted from the center-outlet connection port 724', which is opened to the exterior of the first lid 706, may include the particles or biological objects with relatively larger sizes or higher acoustic contrasts. Accordingly, the first and second networks of channels 711 and 713 are fluidically coupled in parallel.

With continuing reference to FIG. 7G, the microfluidic chip 709 is a part of a microfluidic device 738, which may further include one or more first piezoelectric transducers 740 attached to the exterior of the first lid 706 opposite the first planar surface 700 and/or one or more second piezoelectric transducers 742 attached to the exterior of the second lid 708 opposite the second planar surface 702. The first and second piezoelectric transducers 740 and 742 may be used to generate acoustic pressure waves in the first and second separation channels 710 and 728, respectively. The present invention may be practiced using a single first piezoelectric transducer 740 operating at a first frequency and disposed directly over a portion or the entire length of the first separation channel 710. Alternatively, a cluster of two or more first piezoelectric transducers 740 operating at the first frequency may be disposed directly over and along the first separation channel 710. Likewise, a single second piezoelectric transducer 742 operating at a second frequency may be disposed directly beneath a portion or the entire length of the second separation channel 728. Alternatively, a cluster of two or more second piezoelectric transducers 742 operating at the second frequency may be disposed directly beneath and along the second separation channel 728.

The first piezoelectric transducers 740 may receive power in the form of an oscillating voltage with a frequency in the range of 100 kHz to 100 MHz to generate acoustic pressure waves in the first separation channel 710 between the two sidewalls thereof when a liquid is present. An acoustic standing wave may form in the first separation channel 710 when the channel width, $W_1$, is an integer multiple of one-half wavelength of the acoustic pressure waves, which may depend on the excitation frequency of the power applied to the first piezoelectric transducers 740 and the compressibility and density of the liquid in the first separation channel 710. When $W_1$ is equal to one-half wavelength of the acoustic waves generated by the first piezoelectric transducers 740, a standing wave is formed between the two sidewalls of the first separation channel 710 with a single acoustic pressure node positioned along the center of the first separation channel 710. Objects having relatively larger sizes and/or higher acoustic contrasts may move towards the pressure node at a faster rate, thereby allowing the separation of objects by size or acoustic contrast.

The second piezoelectric transducers 742 may receive power in the form of an oscillating voltage with a frequency in the range of 100 kHz to 100 MHz to generate acoustic pressure waves in the second separation channel 728 between the two sidewalls thereof when a liquid is present. An acoustic standing wave may form in the second separation channel 728 when the channel width, $W_2$, is an integer multiple of one-half wavelength of the acoustic pressure waves, which may depend on the excitation frequency of the power applied to the second piezoelectric transducers 742 and the compressibility and density of the liquid in the second separation channel 728. When $W_2$ is equal to one-half wavelength of the acoustic waves generated by the second piezoelectric transducers 742, a standing wave is formed between the two sidewalls of the second separation channel 728 with a single acoustic pressure node positioned along the center of the second separation channel 728. Objects having relatively larger sizes and/or higher acoustic contrasts may move towards the pressure node, thereby allowing the separation of objects by size or acoustic contrast.

In an embodiment, an acoustic standing wave with single pressure node is formed in each of the first and second separation channels 710 and 728. Accordingly, $W_1$ is equal to one-half of the wavelength of the standing wave in the first separation channel 710, and $W_2$ is equal to one-half of the wavelength of the standing wave in the second separation channel 728. The first and second separation channels 710 and 728 may have the same width (i.e., $W_1=W_2$), which would require the first and second piezoelectric transducers 740 and 742 to operate at substantially the same frequency. Moreover, if sufficient vibration power can be generated by the first or second piezoelectric transducers 740, 742, then only the first piezoelectric transducers 740 or the second piezoelectric transducers 742 may be needed to generate both acoustic standing waves in the first and second separation channels 710 and 728, respectively.

Operation of the microfluidic device 738 under the condition of single pressure node will now be described with reference to FIGS. 7A-7G. A sample fluid containing a first population of first type particles or biological objects 744 and a second population of second type particles or biological entities 746 is introduced into the side-inlet connection port 712' through the first lid 706 as the first fluid, while a buffer fluid is introduced into the center-inlet connection port 716' through the first lid 706 as the second fluid. The first and second type particles or biological objects 744 and 746 may have sufficiently different physical sizes and/or acoustic contrasts, such as mass densities and compressibilities, to allow them to be separated by acoustic radiation pressure. For example, the first and second type particles or biological objects 744 and 746 may have, respectively, large and small physical sizes and/or acoustic contrasts, thereby allowing the acoustic radiation pressure to push the first type particles or biological objects 744 towards the pressure node located along the center of each of the first and second separation channels 710 and 728 when operating under the single-node condition.

The sample fluid containing the first and second type particles or biological objects 744 and 746 is introduced into the side-inlet connection port 712' and is divided into first and second portions that flow through the first and second networks of channels 711 and 713, respectively. Likewise, the buffer fluid is introduced into the center-inlet connection port 716' and is divided into first and second portions that flow through the first and second networks of channels 711 and 713, respectively. The first portion of the sample fluid enters the first separation channel 710 at or near the upstream end thereof via the pair of side inlet channels 714 as two streams flowing adjacent to the sidewalls of the first separation channel 710. The two streams of the first portion of the sample fluid in the first separation channel 710, which may behave like laminar flow, are interposed by the first portion of the buffer fluid from the center-inlet connection port 716', which may act as a sheath fluid that retards or prevents the movement of the second type particles or biological objects 746 towards the pressure node positioned along the center of the first separation channel 710. As the first portion of the sample fluid progresses downstream in the first separation channel 710, the acoustic radiation pressure pushes the first type particles or biological objects 744 towards the pressure node positioned along the center of the first separation channel 710, while the second type particles or biological objects 746 remain mostly close to the sidewalls. At the downstream end of the first separation channel 710, the second type particles or biological objects 746 at or near the sidewalls are diverted through the pair of side outlet channels 722 and into the side-outlet connection port 720' as a part of the first portion of the third fluid, and the first type particles or biological objects 744 at or near the channel center flow through the center outlet channel 726 and into the center-outlet connection port 724' as a part of the first portion of the fourth fluid.

The second portion of the sample fluid enters the second separation channel 728 at or near the upstream end thereof via the pair of side inlet channels 732 as two streams flowing adjacent to the sidewalls of the second separation channel 728. The two streams of the second portion of the sample fluid in the second separation channel 728, which may behave like laminar flow, are interposed by the second portion of the buffer fluid from the center-inlet connection port 716', which may act as a sheath fluid that retards or prevents the movement of the second type particles or biological objects 746 towards the pressure node positioned along the center of the second separation channel 728. As the second portion of the sample fluid progresses downstream in the second separation channel 728, the acoustic radiation pressure pushes the first type particles or biological objects 744 towards the pressure node positioned along the center of the second separation channel 728, while the second type particles or biological objects 746 remain mostly close to the sidewalls. At the downstream end of the second separation channel 728, the second type particles or biological objects 746 at or near the sidewalls are diverted through the pair of side outlet channels 725 and into the side-outlet connection port 720' as a part of the second portion of the third fluid, and the first type particles or biological objects 744 at or near the channel center flow through the center outlet channel 729 and into the center-outlet connection port 724' as a part of the second portion of the fourth fluid.

FIGS. 8A and 8B are, respectively, a top view showing a first planar surface 800 and a bottom view showing a second planar surface 802 of a planar substrate 804 for a microfluidic chip in accordance with another embodiment of the present invention. A first lid 806 is attached to the first planar surface 800 and a second lid 808 is attached to the second planar surface 802 to form the microfluidic chip 809, as shown in the cross-sectional views of FIGS. 8C-8F. The first and second lids 806 and 808 are omitted in FIGS. 8A and 8B for reasons of clarity.

Referring to FIG. 8A, the planar substrate 804 includes a first network of channels 811 recessed from the first planar surface 800 and substantially covered by the first lid 806. The first network of channels 811 includes a first separation channel 810 having an upstream end and a downstream end, a side inlet port 812 for introducing a first fluid into the first separation channel 810, a pair of side inlet channels 814 connecting the side inlet port 812 to the first separation channel 810 at or near the upstream end thereof, a center inlet port 816 for introducing a second fluid into the first separation channel 810, a center inlet channel 818 connecting the center inlet port 816 to the first separation channel 810 at or near the upstream end thereof, a side outlet port 820 for extracting a third fluid from the first separation channel 810, a pair of side outlet channels 822 connecting the side outlet port 820 to the first separation channel 810 at or near the downstream end thereof, a center outlet port 824 for extracting a fourth fluid from the first separation channel 810, and an optional center outlet channel 826 connecting the center outlet port 824 to the first separation channel 810 at or near the downstream end thereof. The center outlet port 824 may alternatively be directly connected to the first separation channel 810 at the downstream end thereof. The first separation channel 810 may have a linear shape with a nominal width, $W_1$, between two sidewalls thereof. $W_1$ may be in the range of approximately 100 μm to 1 mm. One or more of the side inlet channels 814, the center inlet channel 818, the side outlet channels 822, and the center outlet channel 826 may be narrower than the nominal width of the first separation channel 810.

Referring to FIG. 8B, the planar substrate 804 includes a second network of channels 813 recessed from the second planar surface 802 and substantially covered by the second lid 808. The second network of channels 813 includes a second separation channel 828 having an upstream end and a downstream end, a side inlet port 830 for introducing a fifth fluid into the second separation channel 828, a pair of side inlet channels 832 connecting the side inlet port 830 to the second separation channel 828 at or near the upstream end thereof, a center inlet port 834 for introducing a sixth fluid into the second separation channel 828, a center inlet channel 836 connecting the center inlet port 834 to the second separation channel 828 at or near the upstream end thereof, a side outlet port 823 for extracting a seventh fluid from the second separation channel 828, a pair of side outlet channels 825 connecting the side outlet port 823 to the second separation channel 828 at or near the downstream end thereof, a center outlet port 827 for extracting an eighth fluid from the second separation channel 828, and an optional center outlet channel 829 connecting the center outlet port 827 to the second separation channel 828 at or near the downstream end thereof. The center outlet port 827 may alternatively be directly connected to the second separation channel 828 at the downstream end thereof. The second separation channel 828 may have a linear shape with a nominal width, $W_2$, between two sidewalls thereof. $W_2$ may be in the range of approximately 100 µm to 1 mm. One or more of the side inlet channels 832, the center inlet channel 836, the side outlet channels 825, and the center outlet channel 829 may be narrower than the nominal width of the second separation channel 828.

None of the ports 812, 816, 820, 823, 824, 827, 830, and 834 is bored through the planar substrate 804 as shown in FIGS. 8C, 8E, and 8F. The ports 812, 816, 820, and 824 of the first network of channels 811 are opened to the exterior of the microfluidic chip 809 through the first lid 806, which includes through-holes aligned with the respective ports 812, 816, 820, and 824. The ports 823, 827, 830, and 834 of the second network of channels 813 are opened to the exterior of the microfluidic chip 809 through the second lid 808, which includes through-holes aligned with the respective ports 823, 827, 830, and 834. Accordingly, the first and second networks of channels 811 and 813 are not fluidically coupled and may operate independent of each other.

Referring to FIG. 8D, the first separation channel 810 may have a nominal depth, $D_1$, as measured from the first planar surface 800. $D_1$ may be in the range of approximately 50 µm to 500 µm. One or more of the side inlet channels 814, the center inlet channel 818, the side outlet channels 822, and the center outlet channel 826 may be shallower than the nominal depth of the first separation channel 810. The second separation channel 828 may have a nominal depth, $D_2$, as measured from the second planar surface 802. $D_2$ may be in the range of approximately 50 µm to 500 µm. One or more of the side inlet channels 832, the center inlet channel 836, the side outlet channels 825, and the center outlet channel 829 may be shallower than the nominal depth of the second separation channel 828.

While the cross-sectional views of FIGS. 8C-8F may appear to show the ports and channels recessed from the first planar surface 800 and the ports and channels recessed from the second planar surface 802 aligning to each other, features of the first and second networks of channels 811 and 813 do not have to be vertically aligned to practice the present invention.

Referring back to FIG. 8A, the pair of side inlet channels 814 on the first planar surface 800 are connected to the first separation channel 810 at the two sidewalls thereof, near or at the upstream end. Therefore, the first fluid, which flows through the pair of side inlet channels 814, is introduced into the first separation channel 810 as two streams flowing adjacent to the two sidewalls of the first separation channel 810. The center inlet channel 818 is connected to the first separation channel 810 at or near the center thereof. The second fluid, which flows through the center inlet channels 818, is introduced into the center of the first separation channel 810 and is interposed between the two streams of the first fluid at or near the upstream end of the first separation channel 810. The pair of side outlet channels 822 are connected to the first separation channel 810 at the two sidewalls thereof, at or near the downstream end. Therefore, the fluid flowing adjacent to the two sidewalls at or near the downstream end of the first separation channel 810 is diverted by the pair of side outlet channels 822 to become the third fluid and exits the microfluidic chip 809 through the side outlet port 820. The remaining fluid at or near the center of the first separation channel 810 not diverted by the pair of side outlet channels 822 becomes the fourth fluid and proceeds to flow through the center outlet channel 826 and exit the microfluidic chip 809 through the center outlet port 824.

Referring to FIG. 8B, the pair of side inlet channels 832 on the second planar surface 802 are connected to the second separation channel 828 at the two sidewalls thereof, near or at the upstream end. Therefore, the fifth fluid, which flows through the pair of side inlet channels 832, is introduced into the second separation channel 828 as two streams flowing adjacent to the two sidewalls of the second separation channel 828. The center inlet channel 836 is connected to the second separation channel 828 at or near the center thereof. The sixth fluid, which flows through the center inlet channels 836, is introduced into the center of the second separation channel 828 and is interposed between the two streams of the fifth fluid at or near the upstream end of the second separation channel 828. The pair of side outlet channels 825 are connected to the second separation channel 828 at the two sidewalls thereof, at or near the downstream end. Therefore, the fluid flowing adjacent to the two sidewalls at or near the downstream end of the second separation channel 828 is diverted by the pair of side outlet channels 825 to become the seventh fluid and exits the microfluidic chip 809 through the side outlet port 823. The remaining fluid at or near the center of the second separation channel 828 not diverted by the pair of side outlet channels 825 becomes the eighth fluid and proceeds to flow through the center outlet channel 829 and exit the microfluidic chip 809 through the center outlet port 827.

FIG. 8G shows the fluidic paths through the microfluidic chip 809 in accordance with the port positions described above. The first and second fluids are introduced into the microfluidic chip 809 through the side and center inlet ports 812 and 816 on the first planar surface 800, respectively. The third and fourth fluids are extracted from the microfluidic chip 809 through the side and center outlet ports 820 and 824 on the first planar surface 800, respectively. The fifth and sixth fluids are introduced into the microfluidic chip 809 through the side and center inlet ports 830 and 834 on the second planar surface 802, respectively. The seventh and eighth fluids are extracted from the microfluidic chip 809 through the side and center outlet ports 823 and 827 on the second planar surface 802, respectively. There is no intermixing of the fluids between the first and second networks of channels 811 and 813.

The first fluid introduced through the side inlet port 812, which is opened to the exterior of the first lid 806, may be a sample fluid that includes particles or biological objects with different sizes or acoustic contrasts for separation by acoustic radiation pressure, while the second fluid introduced through the center inlet port 816, which is opened to the exterior of the first lid 806, may be a buffer fluid that does not contain any particles or biological objects. After passing through the first separation channel 810, the third fluid extracted from the side outlet port 820, which is opened to the exterior of the first lid 806, may include the particles or biological objects with relatively smaller sizes or lower acoustic contrasts, while the fourth fluid extracted from the center outlet port 824, which is opened to the exterior of the first lid 806, may include the particles or biological objects with relatively larger sizes or higher acoustic contrasts.

The fifth fluid introduced through the side inlet port 830, which is opened to the exterior of the second lid 808, may be a sample fluid that includes particles or biological objects with different sizes or acoustic contrasts for separation by acoustic radiation pressure, while the sixth fluid introduced through the center inlet port 834, which is opened to the exterior of the second lid 808, may be a buffer fluid that does not contain any particles or biological objects. After passing through the second separation channel 828, the seventh fluid extracted from the side outlet port 823, which is opened to the exterior of the second lid 808, may include the particles or biological objects with relatively smaller sizes or lower acoustic contrasts, while the eighth fluid extracted from the center outlet port 827, which is opened to the exterior of the second lid 808, may include the particles or biological objects with relatively larger sizes or higher acoustic contrasts With continuing reference to FIG. 8G, the microfluidic chip 809 is a part of a microfluidic device 838, which may further include one or more first piezoelectric transducers 840 attached to the exterior of the first lid 806 opposite the first planar surface 800 and/or one or more second piezoelectric transducers 842 attached to the exterior of the second lid 808 opposite the second planar surface 802. The first and second piezoelectric transducers 840 and 842 may be used to generate acoustic pressure waves in the first and second separation channels 810 and 828, respectively. The present invention may be practiced using a single first piezoelectric transducer 840 operating at a first frequency and disposed directly over a portion or the entire length of the first separation channel 810. Alternatively, a cluster of two or more first piezoelectric transducers 840 operating at the first frequency may be disposed directly over and along the first separation channel 810. Likewise, a single second piezoelectric transducer 842 operating at a second frequency may be disposed directly beneath a portion or the entire length of the second separation channel 828. Alternatively, a cluster of two or more second piezoelectric transducers 842 operating at the second frequency may be disposed directly beneath and along the second separation channel 828.

The first piezoelectric transducers 840 may receive power in the form of an oscillating voltage with a frequency in the range of 100 kHz to 100 MHz to generate acoustic pressure waves in the first separation channel 810 between the two sidewalls thereof when a liquid is present. An acoustic standing wave may form in the first separation channel 810 when the channel width, $W_1$, is an integer multiple of one-half wavelength of the acoustic pressure waves, which may depend on the excitation frequency of the power applied to the first piezoelectric transducers 840 and the compressibility and density of the liquid in the first separation channel 810. When $W_1$ is equal to one-half wavelength of the acoustic waves generated by the first piezoelectric transducers 840, a standing wave is formed between the two sidewalls of the first separation channel 810 with a single acoustic pressure node positioned along the center of the first separation channel 810. Objects having relatively larger sizes and/or higher acoustic contrasts may move towards the pressure node at a faster rate, thereby allowing the separation of objects by size or acoustic contrast.

The second piezoelectric transducers 842 may receive power in the form of an oscillating voltage with a frequency in the range of 100 kHz to 100 MHz to generate acoustic pressure waves in the second separation channel 828 between the two sidewalls thereof when a liquid is present. An acoustic standing wave may form in the second separation channel 828 when the channel width, $W_2$, is an integer multiple of one-half wavelength of the acoustic pressure waves, which may depend on the excitation frequency of the power applied to the second piezoelectric transducers 842 and the compressibility and density of the liquid in the second separation channel 828. When $W_2$ is equal to one-half wavelength of the acoustic waves generated by the second piezoelectric transducers 842, a standing wave is formed between the two sidewalls of the second separation channel 828 with a single acoustic pressure node positioned along the center of the second separation channel 828. Objects having relatively larger sizes and/or higher acoustic contrasts may move towards the pressure node, thereby allowing the separation of objects by size or acoustic contrast.

In an embodiment, an acoustic standing wave with single pressure node is formed in each of the first and second separation channels 810 and 828. Accordingly, $W_1$ is equal to one-half of the wavelength of the standing wave in the first separation channel 810, and $W_2$ is equal to one-half of the wavelength of the standing wave in the second separation channel 828. The first and second separation channels 810 and 828 may have the same width (i.e., $W_1=W_2$), which would require the first and second piezoelectric transducers 840 and 842 to operate at substantially the same frequency. Moreover, if sufficient vibration power can be generated by the first or second piezoelectric transducers 840, 842, then only the first piezoelectric transducers 840 or the second piezoelectric transducers 842 may be needed to generate both acoustic standing waves in the first and second separation channels 810 and 828, respectively.

Operation of the microfluidic device 838 under the condition of single pressure node will now be described with reference to FIGS. 8A-8G. A sample fluid containing a first population of first type particles or biological objects 844 and a second population of second type particles or biological entities 846 is introduced into the side inlet port 812 through the first lid 806 as the first fluid, while a buffer fluid is introduced into the center inlet port 816 through the first lid 806 as the second fluid. The first and second type particles or biological objects 844 and 846 may have sufficiently different physical sizes and/or acoustic contrasts, such as mass densities and compressibilities, to allow them to be separated by acoustic radiation pressure. For example, the first and second type particles or biological objects 844 and 846 may have, respectively, large and small physical sizes and/or acoustic contrasts, thereby allowing the acoustic radiation pressure to push the first type particles or biological objects 844 towards the pressure node located along the center of the first separation channel 810 when operating under the single-node condition.

The sample fluid containing the first and second type particles or biological objects 844 and 846 is introduced into the first separation channel 810 at or near the upstream end thereof via the pair of side inlet channels 814 as two streams flowing adjacent to the sidewalls of the first separation channel 810. The two streams of the sample fluid in the first separation channel 810, which may behave like laminar flow, are interposed by the buffer fluid from the center inlet port 816, which may act as a sheath fluid that retards or prevents the movement of the second type particles or biological objects 846 towards the pressure node positioned along the center of the first separation channel 810. As the sample fluid progresses downstream in the first separation channel 810, the acoustic radiation pressure pushes the first type particles or biological objects 844 towards the pressure node positioned along the center of the first separation channel 810, while the second type particles or biological objects 846 remain mostly close to the sidewalls. At the downstream end of the first separation channel 810, the second type particles or biological objects 846 at or near the sidewalls are diverted through the pair of side outlet channels 822 and into the side outlet port 820 as a part of the third fluid, and the first type particles or biological objects 844 at or near the channel center flow through the center outlet channel 826 and into the center outlet port 824 as a part of the fourth fluid.

Another sample fluid containing a third population of third type particles or biological objects 848 and a fourth population of fourth type particles or biological entities 850 is introduced into the side inlet port 830 through the second lid 808 as the fifth fluid, while another buffer fluid is introduced into the center inlet port 834 through the second lid 808 as the sixth fluid. The third and fourth type particles or biological objects 848 and 850 may have sufficiently different physical sizes and/or acoustic contrasts, such as mass densities and compressibilities, to allow them to be separated by acoustic radiation pressure. For example, the third and fourth type particles or biological objects 848 and 850 may have, respectively, large and small physical sizes and/or acoustic contrasts, thereby allowing the acoustic radiation pressure to push the third type particles or biological objects 848 towards the pressure node located along the center of the second separation channel 828 when operating under the single-node condition.

The sample fluid containing the third and fourth type particles or biological objects 848 and 850 is introduced into the second separation channel 828 at or near the upstream end thereof via the pair of side inlet channels 832 as two streams flowing adjacent to the sidewalls of the second separation channel 828. The two streams of the sample fluid in the second separation channel 828, which may behave like laminar flow, are interposed by the buffer fluid from the center inlet port 834, which may act as a sheath fluid that retards or prevents the movement of the fourth type particles or biological objects 850 towards the pressure node positioned along the center of the second separation channel 828. As the sample fluid progresses downstream in the second separation channel 828, the acoustic radiation pressure pushes the third type particles or biological objects 848 towards the pressure node positioned along the center of the second separation channel 828, while the fourth type particles or biological objects 850 remain mostly close to the sidewalls. At the downstream end of the second separation channel 828, the fourth type particles or biological objects 850 at or near the sidewalls are diverted through the pair of side outlet channels 825 and into the side outlet port 823 as a part of the seventh fluid, and the third type particles or biological objects 848 at or near the channel center flow through the center outlet channel 829 and into the center outlet port 827 as a part of the eighth fluid.

The presence of the second lid 208/308/408/508/608/708/808 in the microfluidic chip 209/309/409/509/609/709/809 increases the mass thereof compared with the microfluidic chip 100 having only one lid 108, and may require both the first piezoelectric transducers 240/340/440/540/640/740/840 and the second piezoelectric transducers 242/342/442/542/642/742/842 to drive the microfluidic chip 209/309/409/509/609/709/809, which may cause excessive heating. One approach to reduce this undesirable heating effect is to reduce the power applied to the microfluidic chip 209/309/409/509/609/709/809 by using only the first piezoelectric transducers 240/340/440/540/640/740/840 or the second piezoelectric transducers 242/342/442/542/642/742/842, which may necessitate the reduction in the chip mass.

Conventional microfluidic chips, like all semiconductor chips, generally have rectangular planar shapes because they are uniformly diced from wafers at the end of fabrication process. In the present invention, the space surrounding the separation channel 110/210/310/410/510/610/710/810 or the concentration/separation channel 228/328/428/528/628/728/828 has no microfluidic feature and thus can be eliminated to reduce the chip mass.

FIG. 9A is a top view showing a microfluidic chip 900 with reduced mass in accordance with another embodiment of the present invention. The microfluidic chip 900 has a barbell planar shape and can accommodate the first network of channels 111/211/311/411/511/611/711/811, or the second network of channels 213/313/413/513/613/713/813, or both networks of channels for any embodiment shown in FIGS. 1-8. Any one of the microfluidic chips 100/209/309/409/509/609/709/809 shown in FIGS. 1-8 may alternatively have the barbell planar shape of the microfluidic chip 900 instead of the conventional rectangular planar shape.

The microfluidic chip 900 may comprise three sections according to the width profile: first and second end sections 902 and 904 having a first width, $WD_1$, and a center section 906 interposed between the two end sections 902 and 904 and having a second width, $WD_2$. The microfluidic chip 900 may further include an optional first tapered section 908 between the first end section 902 and the center section 906 and/or an optional second tapered section 910 between the second end section 904 and the center section 906. The first tapered section 908 has one end with the width $WD_1$ abutting the first end section 902 and another end with the width $WD_2$ abutting the center section 906. The second tapered section 910 has one end with the width $WD_1$ abutting the second end section 904 and another end with the width $WD_2$ abutting the center section 906. The first end section 902 and the first tapered section 908 may collectively include the ports and channels (e.g., 212-218) connected to the upstream end of the separation channel 110/210/310/410/510/610/710/810, and the second end section 904 and the second tapered section 910 may collectively include the ports and channels (e.g., 220, 222, 224', 226) connected to the downstream end of the separation channel 110/210/310/410/510/610/710/810. The center section 906 may include most of the separation channel 110/210/310/410/510/610/710/810, or most of the concentration/separation channel 228/328/428/528/628/728/828, or both. In an embodiment, the width of the center section is less than half of the width of the end sections 902 and 904 (i.e., $WD_2<WD_1/2$). In another embodiment, the width of the center section is less than one-quarter of the width of the end sections 902 and 904 (i.e., $WD_2<WD_1/4$).

FIG. 9B is a side view of the microfluidic chip 900 comprising the planar substrate 102 and the lid 108, analogous to the chip stack structure shown in FIG. 1E. The planar substrate 102 and the lid 108 each have the barbell planar shape described above.

FIG. 9C is a side view of the microfluidic chip 900 comprising the planar substrate 204/304/404/504/604/704/804, the first lid 206/306/406/506/606/706/806, and the second lid 208/308/408/508/608/708/808, analogous to the chip stack structure shown in FIGS. 2E-8E. The planar substrate 204/304/404/504/604/704/804, the first lid 206/306/406/506/606/706/806, and the second lid 208/308/408/508/608/708/808 each have the barbell planar shape described above.

The barbell planar shape of the microfluidic chip 900 may require the use of a laser dicing technique for wafer dicing instead of the conventional mechanical sawing, which is limited to making substantially straight cuts on wafers.

The planar substrate 102/204/304/404/504/604/704/804 may comprise any suitable material, such as but not limited to glass, metal, quartz, fused silica, silicon, silicon carbide, aluminum nitride, titanium carbide, aluminum oxide, zirconium oxide, lithium niobate, magnesium oxide, or any combination thereof. Microfluidic features, such as channels and ports, may be formed in the planar substrate 102/204/304/404/504/604/704/804 by removing material therefrom via any suitable method, such as but not limited to water jet machining, mechanical machining or drilling, laser machining, wet etching, plasma etching, or any combination thereof. The first lid 108/206/306/406/506/606/706/806 and the second lid 208/308/408/508/608/708/808 may each independently comprise any suitable material, such as but not limited to glass, quartz, fused silica, metal, polymeric material, ceramic material, silicon, silicon carbide, aluminum nitride, titanium carbide, aluminum oxide, zirconium oxide, lithium niobate, magnesium oxide, or any combination thereof. In an embodiment, the planar substrate 102/204/304/404/504/604/704/804, the first lid 108/206/306/406/506/606/706/806, and the second lid 208/308/408/508/608/708/808 are made of silicon. In another embodiment, the planar substrate 102/204/304/404/504/604/704/804 is made of silicon, while at least one of the first lid 108/206/306/406/506/606/706/806 and the second lid 208/308/408/508/608/708/808 is made of glass. The first lid 108/206/306/406/506/606/706/806 and the second lid 208/308/408/508/608/708/808 may be permanently or irreversibly attached to the planar substrate 102/204/304/404/504/604/704/804 by any suitable bonding method, such as but not limited to fusion bonding, anodic bonding, bonding by adhesive, or any combination thereof.

The first piezoelectric transducers 130/240/340/440/540/640/740/840 and the second piezoelectric transducers 242/342/442/542/642/742/842 may be fabricated from lead zirconate titanate (PZT). The first piezoelectric transducers 130/240/340/440/540/640/740/840 and the second piezoelectric transducers 242/342/442/542/642/742/842 may alternatively comprise any suitable piezoelectric material, such as but not limited to potassium niobate, sodium niobate, sodium tungstate, zinc oxide, bismuth ferrite, bismuth titanate, polyvinylidene fluoride, polyvinylidene chloride, polyimide, or any combination thereof. The first piezoelectric transducers 130/240/340/440/540/640/740/840 and the second piezoelectric transducers 242/342/442/542/642/742/842 may be permanently or irreversibly attached to the microfluidic chips 100/209/309/409/509/609/709/809 by soldering or an adhesive, such as but not limited to epoxy, cyanoacrylate, methacrylate, or any combination thereof.

While the present invention has been shown and described with reference to certain preferred embodiments, it is to be understood that those skilled in the art will no doubt devise certain alterations and modifications thereto which nevertheless include the true spirit and scope of the present invention. Thus the scope of the invention should be determined by the appended claims and their legal equivalents, rather than by examples given.

Any element in a claim that does not explicitly state "means for" performing a specified function, or "step for" performing a specific function, is not to be interpreted as a "means" or "step" clause as specified in 35 U.S.C. § 112, ¶16. In particular, the use of "step of" in the claims herein is not intended to invoke the provisions of 35 U.S.C. § 112, ¶16.

What is claimed is:

1. A microfluidic device for sorting biological objects comprising:
    a microfluidic chip including:
        a planar substrate having first and second planar surfaces, the planar substrate including first and second networks of channels recessed respectively from the first and second planar surfaces and directly connected by a through-hole in the planar substrate;
        a first lid attached to the first planar surface of the planar substrate and covering the first network of channels; and
        a second lid attached to the second planar surface of the planar substrate and covering the second network of channels; and
    one or more first piezoelectric transducers attached to an exterior surface of the first lid, opposite to an interior surface of the first lid facing the first network of channels, and configured to generate a first acoustic standing wave having a first wavelength in a first linear channel of the first network of channels.

2. The microfluidic device of claim 1 further comprising one or more second piezoelectric transducers attached to an exterior surface of the second lid, opposite to an interior surface of the second lid facing the second network of channels, and configured to generate a second acoustic standing wave having a second wavelength in a second linear channel of the second network of channels.

3. The microfluidic device of claim 1, wherein the one or more first piezoelectric transducers are configured to further generate a second acoustic standing wave having a second wavelength in a second linear channel of the second network of channels.

4. The microfluidic device of claim 3, wherein the first and second wavelengths are the same.

5. The microfluidic device of claim 1, wherein the planar substrate, the first lid, and the second lid have a barbell planar shape that is characterized by two wide end sections and a narrow center section interposed therebetween.

6. The microfluidic device of claim 5, wherein a width of the narrow center section is less than half of a width of the two wide end sections.

7. The microfluidic device of claim 1, wherein the planar substrate, the first lid, and the second lid each comprise silicon.

8. The microfluidic device of claim 1, wherein the first network of channels includes:
    the first linear channel having upstream and downstream ends and a first width;
    a first port opened to the exterior surface of the first lid;
    a pair of side channels connecting the first port to the first linear channel at the upstream end thereof;
    a second port opened to the exterior surface of the first lid and fluidically connected to the first linear channel at the upstream end thereof; and
    a third port opened to the second planar surface by way of the through-hole and fluidically connected to the first linear channel at the downstream end thereof.

9. The microfluidic device of claim 1, wherein the second network of channels includes:
    a second linear channel having upstream and downstream ends and a second width;
    a first port opened to the first planar surface by way of the through-hole and fluidically connected to the second linear channel at the upstream end thereof;
    a second port opened to an exterior surface of the second lid, opposite to an interior surface of the second lid facing the second network of channels;

a pair of side channels connecting the second port to the second linear channel at the downstream end thereof; and a third port opened to the exterior surface of the second lid and fluidically connected to the second linear channel at the downstream end thereof.

10. The microfluidic device of claim 1, wherein the first network of channels includes:
the first linear channel having upstream and downstream ends and a first width;
a first port opened to the exterior surface of the first lid;
a first pair of side channels connecting the first port to the first linear channel at the upstream end thereof;
a second port opened to the exterior surface of the first lid;
a center channel connecting the second port to the first linear channel at the upstream end thereof;
a third port opened to the exterior surface of the first lid;
a second pair of side channels connecting the third port to the first linear channel at the downstream end thereof; and
a fourth port opened to the second planar surface by way of the through-hole and fluidically connected to the first linear channel at the downstream end thereof, and
wherein the second network of channels includes:
a second linear channel having upstream and downstream ends and a second width;
a fifth port opened to the first planar surface by way of the through-hole and connected to the second linear channel at the upstream end thereof;
a sixth port opened to an exterior surface of the second lid, opposite to an interior surface of the second lid facing the second network of channels;
a third pair of side channels connecting the sixth port to the second linear channel at the downstream end thereof; and
a seventh port opened to the exterior surface of the second lid and fluidically connected to the second linear channel at the downstream end thereof.

11. The microfluidic device of claim 1, wherein the first network of channels includes:
the first linear channel having upstream and downstream ends and a first width;
a first port opened to the exterior surface of the first lid;
a first pair of side channels connecting the first port to the first linear channel at the upstream end thereof;
a second port opened to the exterior surface of the first lid;
a center channel connecting the second port to the first linear channel at the upstream end thereof;
a third port opened to the second planar surface by way of the through-hole;
a second pair of side channels connecting the third port to the first linear channel at the downstream end thereof; and
a fourth port opened to the exterior surface of the first lid and fluidically connected to the first linear channel at the downstream end thereof, and
wherein the second network of channels includes:
a second linear channel having upstream and downstream ends and a second width;
a fifth port opened to the first planar surface by way of the through-hole and connected to the second linear channel at the upstream end thereof;
a sixth port opened to an exterior surface of the second lid, opposite to an interior surface of the second lid facing the second network of channels;
a third pair of side channels connecting the sixth port to the second linear channel at the downstream end thereof; and
a seventh port opened to the exterior surface of the second lid and fluidically connected to the second linear channel at the downstream end thereof.

12. The microfluidic device of claim 1, wherein the first network of channels includes:
the first linear channel having upstream and downstream ends and a first width;
a first port opened to the exterior surface of the first lid;
a first pair of side channels connecting the first port to the first linear channel at the upstream end thereof;
a second port opened to the exterior surface of the first lid;
a center channel connecting the second port to the first linear channel at the upstream end thereof;
a third port opened to the exterior surface of the first lid;
a second pair of side channels connecting the third port to the first linear channel at the downstream end thereof; and
a fourth port opened to the second planar surface by way of the through-hole and fluidically connected to the first linear channel at the downstream end thereof, and
wherein the second network of channels includes:
a second linear channel having upstream and downstream ends and a second width;
a fifth port opened to the first planar surface by way of the through-hole;
a third pair of side channels connecting the fifth port to the second linear channel at the upstream end thereof;
a sixth port opened to an exterior surface of the second lid, opposite to an interior surface of the second lid facing the second network of channels, and fluidically connected to the second linear channel at the upstream end thereof
a seventh port opened to the exterior surface of the second lid;
a fourth pair of side channels connecting the seventh port to the second linear channel at the downstream end thereof; and
an eighth port opened to the exterior surface of the second lid and fluidically connected to the second linear channel at the downstream end thereof.

13. The microfluidic device of claim 1, wherein the first network of channels includes:
the first linear channel having upstream and downstream ends and a first width;
a first port opened to the exterior surface of the first lid;
a first pair of side channels connecting the first port to the first linear channel at the upstream end thereof;
a second port opened to the exterior surface of the first lid;
a center channel connecting the second port to the first linear channel at the upstream end thereof;
a third port opened to the exterior surface of the first lid;
a second pair of side channels connecting the third port to the first linear channel at the downstream end thereof; and
a fourth port opened to the second planar surface by way of the through-hole and fluidically connected to the first linear channel at the downstream end thereof, and
wherein the second network of channels includes:
a second linear channel having upstream and downstream ends and a second width;
a fifth port opened to an exterior surface of the second lid, opposite to an interior surface of the second lid facing the second network of channels;

a third pair of side channels connecting the fifth port to the second linear channel at the upstream end thereof;
a sixth port opened to the first planar surface by way of the through-hole and fluidically connected to the second linear channel at the upstream end thereof
a seventh port opened to the exterior surface of the second lid;
a fourth pair of side channels connecting the seventh port to the second linear channel at the downstream end thereof; and
an eighth port opened to the exterior surface of the second lid and fluidically connected to the second linear channel at the downstream end thereof.

14. The microfluidic device of claim 13, wherein the second width is twice the first width.

15. The microfluidic device of claim 1, wherein the first network of channels includes:
the first linear channel having upstream and downstream ends and a first width;
a first port opened to the exterior surface of the first lid;
a first pair of side channels connecting the first port to the first linear channel at the upstream end thereof;
a second port opened to the exterior surface of the first lid;
a center channel connecting the second port to the first linear channel at the upstream end thereof;
a third port opened to the second planar surface by way of the through-hole;
a second pair of side channels connecting the third port to the first linear channel at the downstream end thereof; and
a fourth port opened to the exterior surface of the first lid and fluidically connected to the first linear channel at the downstream end thereof, and
wherein the second network of channels includes:
a second linear channel having upstream and downstream ends and a second width;
a fifth port opened to the first planar surface by way of the through-hole;
a third pair of side channels connecting the fifth port to the second linear channel at the upstream end thereof;
a sixth port opened to an exterior surface of the second lid, opposite to an interior surface of the second lid facing the second network of channels, and fluidically connected to the second linear channel at the upstream end thereof
a seventh port opened to the exterior surface of the second lid;
a fourth pair of side channels connecting the seventh port to the second linear channel at the downstream end thereof; and
an eighth port opened to the exterior surface of the second lid and fluidically connected to the second linear channel at the downstream end thereof.

16. A microfluidic device for sorting biological objects comprising:
a microfluidic chip including:
a planar substrate having first and second planar surfaces, the planar substrate including first and second networks of channels recessed respectively from the first and second planar surfaces and directly connected by first, second, third, and fourth through-holes in the planar substrate;
a first lid attached to the first planar surface of the planar substrate and covering the first network of channels; and
a second lid attached to the second planar surface of the planar substrate and covering the second network of channels; and
one or more first piezoelectric transducers attached to an exterior surface of the first lid, opposite to an interior surface of the first lid facing the first network of channels, and configured to generate a first acoustic standing wave having a first wavelength in a first linear channel of the first network of channels,
wherein the first network of channels includes:
the first linear channel having upstream and downstream ends and a first width;
a first port opened to the second planar surface by way of the first through-hole;
a first pair of side channels connecting the first port to the first linear channel at the upstream end thereof;
a second port opened to the second planar surface by way of the second through-hole;
a first center channel connecting the second port to the first linear channel at the upstream end thereof;
a third port opened to the second planar surface by way of the third through-hole;
a second pair of side channels connecting the third port to the first linear channel at the downstream end thereof; and
a fourth port opened to the second planar surface by way of the fourth through-hole and fluidically connected to the first linear channel at the downstream end thereof,
wherein the second network of channels includes:
a second linear channel having upstream and downstream ends and a second width;
a fifth port opened to the first planar surface by way of the first through-hole;
a third pair of side channels connecting the fifth port to the second linear channel at the upstream end thereof;
a sixth port opened to the first planar surface by way of the second through-hole;
a second center channel connecting the sixth port to the second linear channel at the upstream end thereof;
a seventh port opened to the first planar surface by way of the third through-hole;
a fourth pair of side channels connecting the seventh port to the second linear channel at the downstream end thereof; and
an eighth port opened to the first planar surface by way of the fourth through-hole and fluidically connected to the second linear channel at the downstream end thereof, and
wherein each of the first, second, third, and fourth through-holes is independently opened to the exterior surface of the first lid or an exterior surface of the second lid, opposite to an interior surface of the second lid facing the second network of channels.

17. A microfluidic device for sorting biological objects comprising:
a microfluidic chip including:
a planar substrate having first and second planar surfaces, the planar substrate including first and second networks of channels recessed respectively from the first and second planar surfaces and directly connected by a through-hole in the planar substrate;
a first lid attached to the first planar surface of the planar substrate and covering the first network of channels; and a second lid attached to the second planar surface of the planar substrate and covering the second network of channels, wherein the first network of channels includes:
- a first linear channel having upstream and downstream ends and a first width;
- a first port opened to an exterior surface of the first lid, opposite to an interior surface of the first lid facing the first network of channels;
- a first pair of side channels connecting the first port to the first linear channel at the upstream end thereof;
- a second port opened to the exterior surface of the first lid and fluidically connected to the first linear channel at the upstream end thereof; and
- a third port opened to the second planar surface by way of the through-hole and fluidically connected to the first linear channel at the downstream end thereof, and wherein the second network of channels includes:
- a second linear channel having upstream and downstream ends and a second width;
- a fourth port opened to the first planar surface by way of the through-hole and fluidically connected to the second linear channel at the upstream end thereof;
- a fifth port opened to an exterior surface of the second lid, opposite to an interior surface of the second lid facing the second network of channels;
- a second pair of side channels connecting the fifth port to the second linear channel at the downstream end thereof; and
- a sixth port opened to the exterior surface of the second lid and fluidically connected to the second linear channel at the downstream end thereof; and one or more first piezoelectric transducers attached to the exterior surface of the first lid and configured to generate a first acoustic standing wave having a first wavelength in the first linear channel, wherein the planar substrate, the first lid, and the second lid have a barbell planar shape that is characterized by two wide end sections and a narrow center section interposed therebetween.

18. The microfluidic device of claim 17 further comprising one or more second piezoelectric transducers attached to the exterior surface of the second lid and configured to generate a second acoustic standing wave having a second wavelength in the second linear channel of the second network of channels.

19. The microfluidic device of claim 17, wherein the one or more first piezoelectric transducers are configured to further generate a second acoustic standing wave having a second wavelength in the second linear channel.

20. The microfluidic device of claim 19, wherein the first and second wavelengths are the same.

\* \* \* \* \*